(12) United States Patent
Sundermann et al.

(10) Patent No.: US 8,088,763 B2
(45) Date of Patent: Jan. 3, 2012

(54) CYCLOHEXYL-1, 4-DIAMINE COMPOUNDS

(75) Inventors: Corinna Sundermann, Aachen (DE); Bernd Sundermann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 1455 days.

(21) Appl. No.: 11/594,963

(22) Filed: Nov. 9, 2006

(65) Prior Publication Data

US 2007/0112007 A1 May 17, 2007

Related U.S. Application Data

(63) Continuation of application No. PCT/EP2005/004913, filed on May 6, 2005.

(30) Foreign Application Priority Data

May 10, 2004 (DE) .......... 10 2004 023 522

(51) Int. Cl.
```
C07D 279/10    (2006.01)
C07D 295/22    (2006.01)
C07D 295/185   (2006.01)
C07D 211/06    (2006.01)
C07D 295/12    (2006.01)
C07C 237/40    (2006.01)
C07C 237/38    (2006.01)
C07C 235/84    (2006.01)
C07C 235/78    (2006.01)
A61K 31/54     (2006.01)
A61K 31/535    (2006.01)
A61K 31/4965   (2006.01)
A61K 31/495    (2006.01)
A61K 31/40     (2006.01)
A61K 31/16     (2006.01)
```
(52) U.S. Cl. ............ 514/227.5; 544/58.4; 544/164; 544/391; 546/226; 548/540; 564/158; 564/155; 564/152; 514/237.5; 514/255.01; 514/330; 514/423; 514/616

(58) Field of Classification Search ........... 544/58.4, 544/164, 391; 546/226; 548/540; 564/158, 564/155, 152; 514/227.5, 237.5, 255.01, 514/330, 423, 616
See application file for complete search history.

(56) References Cited

U.S. PATENT DOCUMENTS
2003/0229119 A1  12/2003  Kym et al.
2004/0229872 A1  11/2004  Friderichs et al.

FOREIGN PATENT DOCUMENTS
WO    WO 02/090317 A1    11/2002

*Primary Examiner* — Peter O'Sullivan
(74) *Attorney, Agent, or Firm* — Crowell & Moring LLP

(57) ABSTRACT

Novel cyclohexyl-1,4-diamine compounds corresponding to formula I,

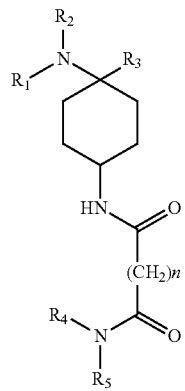

processes for the production thereof, pharmaceutical compositions containing these compounds, methods of producing pharmaceutical compositions including these compounds and related methods of treating or inhibiting certain diseases or conditions.

28 Claims, No Drawings

CYCLOHEXYL-1, 4-DIAMINE COMPOUNDS

CROSS-REFERENCE TO RELATED APPLICATIONS

This application is a continuation of International patent application Serial No. PCT/EP2005/004913 filed May 6, 2005 which claims benefit to German patent application Serial No. 10 2004 023 522.8 filed May 10, 2004, the entire disclosures of which are hereby incorporated in their entirety.

FIELD OF THE INVENTION

The present invention relates to cyclohexyl-1,4-diamine compounds, processes for the production thereof, pharmaceutical compositions containing these compounds, methods of producing pharmaceutical compositions including these compounds and related methods of treating or inhibiting certain diseases or conditions.

BACKGROUND OF THE INVENTION

The treatment of chronic and non-chronic pain conditions has great importance in medicine. There is a worldwide need for effective methods of treating pain. The urgent need for action for patient-oriented and purposeful treatment of chronic and non-chronic pain conditions, this being taken to mean the successful and satisfactory treatment of pain for the patient, is documented in the large number of scientific papers which have recently appeared in the field of applied analgesics and fundamental research work on nociception.

Conventional μ-opioids such as morphine are very effective in the treatment of strong to very strong pain and are of great importance for the treatment of pain. However, it may be advantageous if, in addition to the μ-opioid receptor, further opioid receptors, in particular the ORL1 receptor, are affected, since pure μ-opioids also have undesirable side effects, such as obstipation and respiratory depression, and may also lead to addiction. The opioid receptors δ, κ and ORL1 are also involved in the state of pain (Opioids: Introduction, pp. 127-150, Further Opioid Receptors, 455-476 in: Analgesics—From Chemistry and Pharmacology to Clinical Application, Wiley VCH, 2002).

It is also known that influencing of serotonin and/or noradrenalin re-uptake can be beneficial to the effects and side effects of opioids (Example: Tramadol, see Opioids with Clinical Relevance: Tramadol, 228-230 in: Analgesics—From Chemistry and Pharmacology to Clinical Application, Wiley VCH, 2002).

The ORL1 receptor is also involved in the regulation of further physiological and pathophysiological processes. These include inter alia learning and memory formation (Manabe et al, Nature, 394, 1997, pp. 577-581), Hörvermögen [Hearing capacity] (Nishi et al, EMBO J., 16, 1997, pp. 1858-1864) and numerous further processes. In a synopsis by Calo et al (Br. J. Pharmacol., 129, 2000, 1261-1283) there is an overview of the indications or biological procedures, in which the ORL1 receptor plays a part or could highly probably play a part. Mentioned inter alia are: analgesics, stimulation and regulation of nutrient absorption, effect on μ-agonists such as morphine, treatment of withdrawal symptoms, reduction of the addiction potential of opioids, anxiolysis, modulation of motor activity, memory disorders, epilepsy; modulation of neurotransmitter release, in particular of glutamate, serotonin and dopamine, and therefore neurodegenerative diseases; influencing the cardiovascular system, triggering an erection, diuresis, anti-natriuresis, electrolyte balance, arterial blood pressure, water-retention disorders, intestinal motility (diarrhoea), relaxation of the respiratory tract, micturation reflex (urinary incontinence). The use of agonists and antagonists such as anoretics, analgesics (also when administered with opioids) or nootropics will also be discussed.

Structurally related compounds which have an affinity with the ORL1 receptor are known from the prior art (WO 02090317). The effect on noradrenalin and serotonin re-uptake has not previously been described for this structural class.

SUMMARY OF THE INVENTION

An object of the present invention was to provide pharmaceutical compositions which act on the opioid receptor system and are thus suitable for pharmaceutical compositions, in particular for the treatment of the various diseases associated with this system according to the prior art and for use in the indications mentioned therein. The compounds are also intended to influence noradrenalin and serotonin re-uptake The invention therefore relates to substituted cyclohexyl-1,4-diamine derivatives of general formula I,

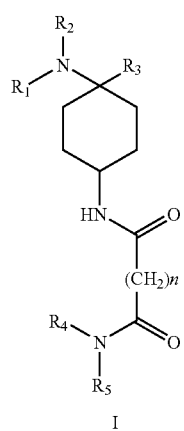

wherein n represents 1, 2, 3, 4 or 5

$R^1$ and $R^2$ independently of one another represent H; respectively saturated or unsaturated, branched or unbranched, singly or multiply substituted or unsubstituted $C_{1-5}$ alkyl; respectively singly or multiply substituted or unsubstituted $C_{3-8}$-cycloalkyl; or respectively singly or multiply substituted or unsubstituted aryl, $C_{3-8}$ cycloalkyl or heteroaryl bound by $C_{1-3}$ alkyl;

or the radicals R1 and R2 together represent CH2CH2OCH2CH2, CH2CH2NR10CH2CH2 or (CH2)3-6, wherein $R^{10}$ represents H; respectively saturated or unsaturated, branched or unbranched, singly or multiply substituted or unsubstituted $C_{1-5}$ alkyl respectively singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl; respectively substituted or unsubstituted C(O)phenyl, C(O)heteroaryl, $C(O)C_{1-5}$ alkyl;

$R^3$ represents respectively saturated or unsaturated, branched or unbranched, singly or multiply substituted or unsubstituted $C_{1-5}$ alkyl; respectively singly or multiply substituted or unsubstituted $C_{3-8}$ cycloalkyl; respectively unsubstituted or singly or multiply substituted aryl or heteroaryl; respectively unsubstituted or singly or multiply substituted aryl, heteroaryl or $C_{3-8}$ cycloalkyl bound by a $C_{1-3}$ alkyl group;

$R^4$ represents —$(CR^6R^7)_pR^8$, wherein p represents 0, 1, 2, 3 or 4

$R^6$ represents H or respectively saturated or unsaturated, branched or unbranched, unsubstituted or singly or multiply substituted $C_{1-5}$ alkyl, $R^7$ represents H, respectively saturated or unsaturated, branched or unbranched, unsubstituted or singly or multiply substituted $C_{1-5}$ alkyl or $COOR^9$, or $R^6$ and $R^7$ form a ring $(CH_2)_kCHR^8(CH_2)m$, where k=1, 2, 3 and m=1, 2

$R^8$ represents respectively saturated or unsaturated, branched or unbranched, unsubstituted or singly or multiply substituted $C_{1-6}$ alkyl, respectively unsubstituted or singly or multiply substituted $C_{3-8}$ cycloalkyl, aryl or heteroaryl, $R^9$ represents H or $C_{1-5}$ alkyl $R^5$ represents H or —$(CH_2)_lR^8$, wherein l represents 1, 2 or 3, or together with $R^4$ represents $CH_2CHR^{14}OCHR^{14}CH_2$, $CH_2CH_2SCH_2CH_2$ $CH_2CH_2NR^{11}CH_2CH_2$, $(CR^{12}R^{13})_{3-6}$ or

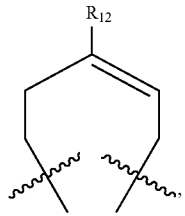

wherein $R^{11}$ represents H; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively singly or multiply substituted or unsubstituted aryl or heteroaryl; or respectively singly or multiply substituted or unsubstituted aryl, C3-8 cycloalkyl or heteroaryl bound by $C_{1-3}$ alkyl;

$R^{12}$ represents H; respectively saturated or unsaturated, branched or unbranched, singly or multiply substituted or unsubstituted $C_{1-5}$ alkyl; OH; unsubstituted or singly or multiply substituted C(O)phenyl; respectively singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl;

and $R^{13}$ represents H or OH or together with $R^{12}$ via the same C atom (spiro compound) or an adjacent C atom forms a five-membered or six-membered ring which may contain heteroatoms, be saturated or unsaturated, substituted or unsubstituted and/or be part of a polycyclic system;

$R^{14}$ represents H or respectively saturated or unsaturated, branched or unbranched, singly or multiply substituted or unsubstituted $C_{1-3}$ alkyl;

in the form of the racemate; the enantiomers, diastereomers, mixtures of the enantiomers or diastereomers or an individual enantiomer or diastereomer; the bases and/or salts of physiologically acceptable acids or cations.

The compounds according to the invention exhibit good binding to the µ receptor and the ORL1 receptor, but also to other opioid receptors. Surprisingly it has been found that the compounds are also good inhibitors of noradrenalin and serotonin re-uptake. They are therefore also suitable for treating depression and/or bulimia and/or anorexia and/or catalepsy and/or anxiolysis and/or increasing alertness and/or libido.

The terms "$C_{1-6}$ alkyl", "$C_{1-5}$ alkyl" and "$C_{1-3}$ alkyl" comprise, in the context of this invention, acyclic saturated or unsaturated hydrocarbon radicals, which may be branched or straight-chained and unsubstituted or singly or multiply substituted, with 1, 2, 3, 4, 5 or 6 C atoms or 1, 2, 3, 4 or 5 C atoms or 1, 2 or 3 C atoms, i.e. $C_{1-6}$ alkanyls, $C_{2-6}$ alkenyls and $C_{2-6}$ alkynyls or $C_{1-5}$ alkanyls, $C_{2-5}$ alkenyls and $C_{2-5}$ alkynyls or $C_{1-3}$ alkanyls, $C_{2-3}$ alkenyls and $C_{2-3}$ alkynyl. Alkenyls have at least one C—C double bond and alkynyls at least one C—C treble bond. Alkyl is advantageously selected from the group comprising methyl, ethyl, n-propyl, 2-propyl, n-butyl, iso-butyl, sec.-butyl, tert.-butyl, n-pentyl, iso-pentyl, neo-pentyl, n-hexyl, 2-hexyl, 2,3-dimethylbutyl; ethylenyl (vinyl), ethynyl, propenyl (—$CH_2CH=CH_2$, —$CH=CH-CH_3$, —$C(=CH_2)$—$CH_3$), propynyl (—$CH-C\equiv CH$, —$C\equiv C$—$CH_3$), 1,1-dimethylethyl, 1,1-dimethylpropyl, butenyl, butynyl, pentenyl and pentynyl, hexenyl and hexynyl.

For the purposes of this invention, the term "cycloalkyl" or "$C_{3-8}$ cycloalkyl" denotes cyclic hydrocarbons with 3, 4, 5, 6, 7 or 8 carbon atoms, wherein the hydrocarbons may be saturated or unsaturated (but not aromatic), unsubstituted or singly or multiply substituted. With respect to cycloalkyl, the term also comprises saturated or unsaturated (but not aromatic) cycloalkyls, in which one or two carbon atoms are replaced by an S, N or O heteroatom. $C_{3-8}$ cycloalkyl is advantageously selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

The term "$(CH_2)_{3-6}$" denotes —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$—.

The term "aryl", according to this invention, denotes carbocyclic ring systems comprising at least one aromatic ring, but without a heteroatom in only one of the rings, inter alia phenyls, naphthyls and phenanthrenyls, fluoranthenyls, fluorenyls, indanyls and tetralinyls. The aryl radicals can also be condensed with further saturated, (partially) unsaturated or aromatic ring systems. Each aryl radical can be present unsubstituted or singly or multiply substituted, wherein the aryl substituents may be the same or different and in any desired and possible position of the aryl. Phenyl or naphthyl radicals are particularly advantageous.

The term "heteroaryl" represents a 5-, 6- or 7-membered cyclic aromatic radical, which contains at least 1 heteroatom, optionally also 2, 3, 4 or 5 heteroatoms, wherein the heteroatoms may be the same or different and the heterocycle may be unsubstituted or singly or multiply substituted; in the case of substitution on the heterocycle, the substituents may be the same or different and in any desired and possible position of the heteroaryl. The heterocycle may also be part of a bi- or polycyclic system. Preferred heteroatoms are nitrogen, oxygen and sulphur. It is preferred for the heteroaryl radical to be selected from the group comprising pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the binding with the compounds of general structure I can be made via any desired and possible ring member of the heteroaryl radical.

In conjunction with "alkyl", the term "substituted", according to this invention, denotes substitution of one or more hydrogen radicals by F, Cl, Br, I, —CN, =O, =S, $NH_2$, NH-alkyl, NH-aryl, NH-heteroaryl, NH-cycloalkyl, NH-alkyl-aryl, NH-alkyl-heteroaryl, NH-alkyl-OH, $N(alkyl)_2$, $N(alkyl-aryl)_2$, $N(alkyl-heteroaryl)_2$, $N(cycloalkyl)_2$, $N(alkyl-OH)_2$, NH(C=O)alkyl, NH(C=O)aryl, $NO_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, C(=O)$C_{1-6}$ alkyl, C(=S)$C_{1-6}$ alkyl, C(=O)aryl, C(=S)aryl, C(=O)$C_{1-6}$ alkyl-aryl, C(=S)$C_{1-6}$-alkyl aryl, C(=O)-heteroaryl, C(=S)-heteroaryl, C(=O)-cycloalkyl, C(=S)-cycloalkyl, $CO_2H$, $CO_2$-alkyl, $CO_2$-alkyl-aryl, C(=O)$NH_2$, C(=O)NH-alkyl, C(=O)NH-aryl, C(=O)NH-cycloalkyl, C(=O)N$(alkyl)_2$, C(=O)N$(alkyl-aryl)_2$, C(=O)N$(alkyl-heteroaryl)_2$, C(=O)N$(cycloalkyl)_2$, SO-alkyl, $SO_2$-alkyl, $SO_2NH_2$, $SO_3H$, PO(O—$C_{1-6}$ alkyl$)_2$, cycloalkyl, aryl or heteroaryl, wherein the term "multiply substituted radicals" denotes radicals that have been multiply substituted, for example twice or three times, either on different or on the same atoms, for example three times on the same C atom, as in the case of $CF_3$ or —$CH_2CF_3$, or in various positions, as in the case of —CH(OH)—CH=CH—$CHCl_2$. Multiple substitution can take place with the same substituent or with different substituents. A substituent may optionally also be substituted for its part; thus —O-alkyl also includes inter alia —O—$CH_2$—$CH_2$—O—$CH_2$—$CH_2$—OH.

With respect to "aryl", "heteroaryl" and "cycloalkyl", according to this invention, "singly or multiply substituted" denotes the single or multiple, for example double, treble, quadruple or quintuple, substitution of one or more hydrogen atoms of the ring system by F, Cl, Br, I, CN, $NH_2$, NH-alkyl, NH-aryl, NH-heteroaryl, NH-alkyl-aryl, NH-alkyl-heteroaryl, NH-cycloalkyl, NH-alkyl-OH, $N(alkyl)_2$, $N(alkyl-aryl)_2$, $N(alkyl-heteroaryl)_2$, $N(cycloalkyl)_2$, $N(alkyl-OH)_2$, $NO_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, C(=O)$C_{1-6}$ alkyl, C(=S)$C_{1-6}$ alkyl, C(=O)aryl, C(=S)aryl, C(=O)—$C_{1-6}$ alkyl-aryl, C(=S)$C_{1-6}$ alkyl-aryl, C(=O)-heteroaryl, C(=S)-heteroaryl, C(=O)-cycloalkyl, C(=S)-cycloalkyl, $CO_2H$, $CO_2$-alkyl, $CO_2$-alkyl-aryl, C(=O)$NH_2$, C(=O)NH-alkyl, C(=O)NH-aryl, C(=O)NH-cycloalkyl, C(=O)N$(alkyl)_2$, C(=O)N$(alkyl-aryl)_2$, C(=O)N$(alkyl-heteroaryl)_2$, C(=O)N$(cycloalkyl)_2$, S(O)-alkyl, S(O)-aryl, $SO_2$-alkyl, $SO_2$-aryl, $SO_2NH_2$, $SO_3H$, $CF_3$, =O, =S;

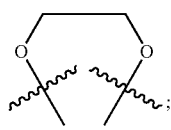

alkyl, cycloalkyl, aryl and/or heteroaryl; on one atom or optionally on different atoms (wherein a substituent can, in turn, optionally be substituted). Multiple substitution takes place here using the same or different substituents.

The term "salt" denotes any form of the active ingredient according to this invention in which it assumes or is charged with an ionic form and is coupled to a counter ion (a cation or anion) or is in solution. This also includes complexes of the active ingredient with other molecules and ions, in particular complexes complexed by ionic interactions. In particular this denotes (and this is also a preferred embodiment of this invention) physiologically acceptable salts, in particular physiologically acceptable salts with cations or bases and physiologically acceptable salts with anions or acids or else a salt formed with a physiologically acceptable acid or physiologically acceptable cation.

The term "physiologically acceptable salt with anions or acids" denotes, in the context of this invention, salts of at least one of the compounds according to this invention—usually protonated, for example on nitrogen—as a cation with at least one anion which are physiologically acceptable—in particular when applied to humans and/or mammals. In the context of this invention this denotes, in particular, the salt formed with a physiologically acceptable acid, namely salts of the respective active ingredient with inorganic or organic acids which are physiologically acceptable—in particular when applied to humans and/or mammals. Examples of physiologically acceptable salts of specific acids include salts of: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, saccharic acid, monomethyl sebacic acid, 5-oxo-proline, hexane-1-sulphonic acid, nicotinic acid, 2-, 3- or 4-amino benzoic acid, 2,4,6-trimethyl-benzoic acid, α-lipoic acid, acetyl glycine, phosphoric acid, maleic acid, malonic acid, hippuric acid and/or aspartic acid. The hydrochloride salt, the citrate and the hemicitrate are particularly preferred.

The term "salt formed with a physiologically acceptable acid", according to this invention, denotes salts of the respective active ingredient with inorganic or organic acids which are physiologically acceptable—in particular when applied to humans and/or mammals. The hydrochloride and the citrate are particularly preferred. Examples of physiologically acceptable acids include: hydrochloric acid, hydrobromic acid, sulphuric acid, methane sulphonic acid, formic acid, acetic acid, oxalic acid, succinic acid, tartaric acid, mandelic acid, fumaric acid, lactic acid, citric acid, glutamic acid, saccharic acid, monomethyl sebacic acid, 5-oxo-proline, hexane-1-sulphonic acid, nicotinic acid, 2-, 3- or 4-amino benzoic acid, 2,4,6-trimethyl-benzoic acid, α-lipoic acid, acetyl glycine, hippuric acid and/or aspartic acid.

The term "physiologically acceptable salt with cations or bases" denotes, in the context of this invention, salts of at least one of the compounds according to this invention—usually a (deprotonated) acid—as an anion with at least one, preferably inorganic, cation, which are physiologically acceptable, in particular when applied to humans and/or mammals. The salts of the alkali and alkaline-earth metals are particularly preferred, but also ammonium salts, in particular (mono-) or (di-) sodium, (mono-) or (di-)potassium, magnesium or calcium salts.

The term "salt formed with a physiologically acceptable cation" denotes, according to this invention, salts of at least one of the respective compounds as an anion with at least one inorganic cation, which are physiologically acceptable, in particular when applied to humans and/or mammals. The salts of the alkali and alkaline-earth metals are particularly preferred, but also ammonium salts, in particular (mono-) or (di-) sodium, (mono-) or (di-)potassium, magnesium or calcium salts.

For a preferred embodiment of the substituted cyclohexyl-1,4-diamine derivatives according to the invention $R^1$ and $R^2$ independently of one another represent H; saturated or unsaturated, branched or unbranched, singly or multiply substituted or unsubstituted $C_{1-5}$ alkyl;

or the radicals $R^1$ and $R^2$ together form a ring and represent $CH_2CH_2OCH_2CH_2$, $CH_2CH_2NR^{10}CH_2CH_2$ or $(CH_2)_{3-6}$, wherein $R^{10}$ represents H; saturated or unsaturated, branched or unbranched, singly or multiply substituted or unsubstituted $C_{1-5}$ alkyl.

Particularly preferred are substituted cyclohexyl-1,4-diamine derivatives, wherein $R^1$ and $R^2$ independently of one another represent $CH_3$ or H, wherein $R^1$ and $R^2$ do not simultaneously represent H, or $R^1$ and $R^2$ represent $CH_2CH_2OCH_2CH_2$ or $(CH_2)_6$.

Also preferred are substituted cyclohexyl-1,4-diamine derivatives, wherein $R^3$ represents respectively unsubstituted or singly or multiply substituted cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl; respectively unsubstituted or singly or multiply substituted $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bound by a saturated, unbranched $C_{1-2}$ alkyl group;
  in particular
$R^3$ represents respectively unsubstituted or singly or multiply substituted phenyl, furyl, thiophenyl, naphthyl, benzyl, benzofuranyl, indolyl, indanyl, benzodioxanyl, benzodioxanyl, pyridyl, pyrimidyl, pyrazinyl or benzothiophenyl; respectively unsubstituted or singly or multiply substituted phenyl, furyl or thiophenyl bound by a saturated, unbranched $C_{1-2}$ alkyl group.

Particularly preferred are substituted cyclohexyl-1,4-diamine derivatives, wherein $R^3$ represents respectively substituted or unsubstituted phenyl, thiophenyl, pyridyl or benzyl, particularly preferably 4-methylbenzyl, 3-chlorobenzyl, 4-chlorobenzyl, 3-methylbenzyl, benzyl, phenyl, thiophenyl and 3-fluorophenyl.

Substituted cyclohexyl-1,4-diamine derivatives wherein n represents 2 or 3 are preferred.

Substituted cyclohexyl-1,4-diamine derivatives wherein $R^4$ represents
—$(CR^6R^7)_pR^8$ and $R^5$ represents H are also preferred.

Substituted cyclohexyl-1,4-diamine derivatives wherein $R^4$ represents $(CH_2)_pR^8$ and $R^5$ represents —$(CH_2)_rR^8$ are additionally preferred.

Substituted cyclohexyl-1,4-diamine derivatives wherein $R^4$ and $R^5$ together represent $CH_2CHR^{14}OCHR^{14}CH_2$, $CH_2CH_2SCH_2CH_2$, $CH_2CH_2NR^{11}CH_2CH_2$ $(CR^{12}R^{13})_{3-6}$ or

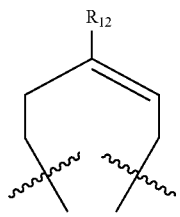

are also preferred.

Substituted cyclohexyl-1,4-diamine derivatives wherein $R^6$ represents H and $R^7$ represents H, $CH_3$, unsubstituted or singly or multiply substituted benzyl, or $COOR^9$ or $R^6$ and $R^7$ form a ring $(CH_2)_kCHR^8(CH_2)_m$ are also preferred.

Substituted cyclohexyl-1,4-diamine derivatives wherein $R^8$ represents respectively saturated or unsaturated, branched or unbranched, unsubstituted or singly or multiply substituted $C_{1-6}$ alkyl; respectively unsubstituted or singly or multiply substituted cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyrrolidinyl, tetrahydrofuryl, piperazinyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl are also preferred.

Substituted cyclohexyl-1,4-diamine derivatives wherein $R^8$ represents respectively saturated or unsaturated, branched or unbranched, unsubstituted or singly or multiply substituted $C_{1-6}$ alkyl; respectively unsubstituted or singly or multiply substituted pyrrolidinyl, morpholinyl, tetrahydrofuryl, tetrahydronaphthyl, dihydroindolyl, pyridyl, thienyl, piperazinyl, naphthyl, indanyl, quinolinyl, cyclopropyl, cyclopentyl, cyclohexyl, cycloheptyl, cyclooctyl, adamantyl, furyl, benzofuryl, phenyl or indolyl are particularly preferred.

Most preferred are substituted cyclohexyl-1,4-diamine derivatives from the group comprising
N-[1-(2,6-dichloro-benzyl)-pyrrolidin-3-yl]-N'-[4-dimethylamino-4-(4-methyl-benzyl)-cyclohexyl]-succinamide
N-[4-(3-chloro-benzyl)-4-dimethylamino-cyclohexyl]-N'-(2-oxo-tetrahydro-furan-3-yl)-succinamide
N-[4-(4-chloro-benzyl)-4-dimethylamino-cyclohexyl]-N'-(3,3-diphenyl-propyl)-succinamide
N-[4-dimethylamino-4-(4-methyl-benzyl)-cyclohexyl]-4-[4-(7-methoxy-benzo[1,3]dioxol-5-ylmethyl)-piperazin-1-yl]-4-oxo-butyramide
N-[4-(4-chloro-benzyl)-4-dimethylamino-cyclohexyl]-4-(3,6-dihydro-2H-pyridin-1-yl)-4-oxo-butyramide
N-[4-dimethylamino-4-(4-methyl-benzyl)-cyclohexyl]-4-oxo-4-(4-m-tolyl-piperazin-1-yl)-butyramide
2-{3-[4-(4-chloro-benzyl)-4-dimethylamino-cyclohexylcarbamoyl]-propionylamino}-propanoic acid ethylester
N-[4-(3-chloro-benzyl)-4-dimethylamino-cyclohexyl]-4-(8-fluoro-1,3,4,5-tetrahydro-pyrido[4,3-b]indol-2-yl)-4-oxo-butyramide
3-{3-[4-dimethylamino-4-(4-methyl-benzyl)-cyclohexylcarbamoyl]-propionylamino}-propanoic acid ethylester
N-[4-dimethylamino-4-(4-methyl-benzyl)-cyclohexyl]-4-[4-(5-methyl-pyrazin-2-carbonyl)-piperazin-1-yl]-4-oxo-butyramide
N-[4-dimethylamino-4-(4-methyl-benzyl)-cyclohexyl]-N'-methyl-N'-[2-(2,2,2-trifluoro-acetylamino)-ethyl]-succinamide
N-[4-(3-chloro-benzyl)-4-dimethylamino-cyclohexyl]-N'-(2-pyridin-2-yl-ethyl)-succinamide
N-[4-(4-chloro-benzyl)-4-dimethylamino-cyclohexyl]-4-oxo-4-thiomorpholin-4-yl-butyramide
N-[4-(4-chloro-benzyl)-4-dimethylamino-cyclohexyl]-4-[4-(5-methyl-pyrazin-2-carbonyl)-piperazin-1-yl]-4-oxo-butyramide
N-[4-dimethylamino-4-(3-methyl-benzyl)-cyclohexyl]-N'-(2-thiophen-2-yl-ethyl)-succinamide
N-[4-(4-chloro-benzyl)-4-dimethylamino-cyclohexyl]-4-[4-(4-ethoxy-phenyl)-piperazin-1-yl]-4-oxo-butyramide
N-allyl-N'-[4-(4-chloro-benzyl)-4-dimethylamino-cyclohexyl]-N-methyl-succinamide 5-[4-(2,5-dimethoxy-benzyl)-piperazin-1-yl]-5-oxo-valeric acid (4-benzyl-4-dimethylamino-cyclohexyl)-amide
4-(3,6-dihydro-2H-pyridin-1-yl)-N-[4-dimethylamino-4-(4-methyl-benzyl)-cyclohexyl]-4-oxo-butyramide
N-[4-dimethylamino-4-(3-methyl-benzyl)-cyclohexyl]-4-(4-methyl-piperidin-1-yl)-4-oxo-butyramide
N-[4-dimethylamino-4-(4-methyl-benzyl)-cyclohexyl]-4-oxo-4-(4-pyridin-2-yl-piperazin-1-yl)-butyramide
({3-[4-dimethylamino -4-(3-methyl-benzyl)-cyclohexylcarbamoyl]-propionyl}-methyl-amino)-acetic acid benzyl ester
4-[4-(2,6-dichloro-benzyl)-piperazin-1-yl]-N-[4-dimethylamino-4-(3-methyl-benzyl)-cyclohexyl]-4-oxo-butyramide
{[4-(4-benzyl-4-dimethylamino-cyclohexylcarbamoyl)-butyryl]-methyl-amino}-acetic acid tert butyl ester
5-[4-(2-fluoro-5-methoxy-benzyl)-piperazin-1-yl]-5-oxo-valeric acid (4-benzyl-4-dimethylamino-cyclohexyl)-amide
N-[4-(4-chloro-benzyl)-4-dimethylamino-cyclohexyl]-N'-(3-methoxy-propyl)-succinamide
4-[4-(4-acetyl-phenyl)-piperazin-1-yl]-N-[4-dimethylamino-4-(4-methyl-benzyl)-cyclohexyl]-4-oxo-butyramide
4-{3-[4-dimethylamino-4-(4-methyl-benzyl)-cyclohexylcarbamoyl]-propionyl}-piperazin-1-carboxylic acid-tert-butylester
N-[4-(3-chloro-benzyl)-4-dimethylamino-cyclohexyl]-N'-(tetrahydro-furan-2-ylmethyl)-succinamide
2-{3-[4-(3-chloro-benzyl)-4-dimethylamino-cyclohexylcarbamoyl]-propionylamino}-propanoic acid ethylester
N-(3-bromo-benzyl)-N'-[4-dimethylamino-4-(3-methyl-benzyl)-cyclohexyl]-succinamide
3-(4-chloro-phenyl)-2-{3-[4-dimethylamino-4-(4-methyl-benzyl)-cyclohexylcarbamoyl]-propionylamino}-propanoic acid methylester
N-[4-(3-chloro-benzyl)-4-dimethylamino-cyclohexyl]-4-[4-(5-methyl-pyrazin-2-carbonyl)-piperazin-1-yl]-4-oxo-butyramide
N-[4-(4-chloro-benzyl)-4-dimethylamino-cyclohexyl]-N'-naphthalen-1-ylmethyl-succinamide
N-[4-dimethylamino-4-(3-methyl-benzyl)-cyclohexyl]-4-[4-(3-fluoro-4-methoxy-benzyl)-piperazin-1-yl]-4-oxo-butyramide
N-[4-dimethylamino-4-(4-methyl-benzyl)-cyclohexyl]-N'-[2-(1H-indol-3-yl)-ethyl]-N'-methyl-succinamide
(4-{3-[4-(3-chloro-benzyl)-4-dimethylamino-cyclohexylcarbamoyl]-propionylamino}-benzyl)-phosphonic acid diethylester
N-[4-dimethylamino-4-(4-methyl-benzyl)-cyclohexyl]-N'-methyl-N'-(2-pyridin-2-yl-ethyl)-succinamide
N-[4-(3-chloro-benzyl)-4-dimethylamino-cyclohexyl]-4-(3,6-dihydro-2H-pyridin-1-yl)-4-oxo-butyramide
N-[4-dimethylamino-4-(3-methyl-benzyl)-cyclohexyl]-N'-(1-methyl-3-phenyl-propyl)-succinamide
5-[4-(5-methyl-pyrazin-2-carbonyl)-piperazin-1-yl]-5-oxo-valeric acid (4-benzyl-4-dimethylamino-cyclohexyl)-amide
N-[4-(3-chloro-benzyl)-4-dimethylamino-cyclohexyl]-N'-(2-chloro-6-methyl-benzyl)-succinamide
N-allyl-N'-[4-(3-chloro-benzyl)-4-dimethylamino-cyclohexyl]-N-methyl-succinamide
N-[4-(4-chloro-benzyl)-4-dimethylamino-cyclohexyl]-N'-cyclopentyl-succinamide
N-[4-dimethylamino-4-(4-methyl-benzyl)-cyclohexyl]-N'-(tetrahydro-furan-2-ylmethyl)-succinamide
(4-{3-[4-dimethylamino-4-(3-methyl-benzyl)-cyclohexylcarbamoyl]-propionylamino}-benzyl)-phosphonic acid diethylester
N-[4-(4-chloro-benzyl)-4-dimethylamino-cyclohexyl]-4-[4-(2-methoxy-phenyl)-piperazin-1-yl]-4-oxo-butyramide
N-[4-dimethylamino-4-(3-methyl-benzyl)-cyclohexyl]-4-[4-(3-methoxy-phenyl)-piperazin-1-yl]-4-oxo-butyramide
N-[4-(4-chloro-benzyl)-4-dimethylamino-cyclohexyl]-N'-(3,5-difluoro-benzyl)-succinamide
N-[4-(4-chloro-benzyl)-4-dimethylamino-cyclohexyl]-N'-(2-methyl-benzyl)-succinamide
N-[4-dimethylamino-4-(4-methyl-benzyl)-cyclohexyl]-4-oxo-4-{4-[(2,2,2-trifluoro-acetylamino)-methyl]-piperidin-1-yl}-butyramide
N-[4-(4-chloro-benzyl)-4-dimethylamino-cyclohexyl]-N'-[2-(1H-indol-3-yl)-ethyl]-succinamide
N-[4-(3-chloro-benzyl)-4-dimethylamino-cyclohexyl]-N'-[2-(1H-indol-3-yl)-ethyl]-N'-methyl-succinamide
5-[4-(7-methoxy-benzo[1,3]dioxol-5-ylmethyl)-piperazin-1-yl]-5-oxo-valeric acid (4-benzyl-4-dimethylamino-cyclohex)/l)-amide
N-benzyl-N'-[4-dimethylamino-4-(3-methyl-benzyl)-cyclohexyl]-N-(2-hydroxy-ethyl)-succinamide
5-[4-(2,3-dimethyl-phenyl)-piperazin-1-yl]-5-oxo-valeric acid (4-benzyl-4-dimethylamino-cyclohexyl)-amide
N-[4-(4-chloro-benzyl)-4-dimethylamino-cyclohexyl]-N'-[2-(1H-indol-3-yl)-ethyl]-N'-methyl-succinamide
N-[4-dimethylamino-4-(4-methyl-benzyl)-cyclohexyl]-4-[4-(2,3-dimethyl-phenyl)-piperazin-1-yl]-4-oxo-butyramide
Glutaric acid-(4-benzyl-4-dimethylamino-cyclohexyl)-amide (1,2,3,4-tetrahydro-naphthalen-1-yl)-amide
N-[4-(4-chloro-benzyl)-4-dimethylamino-cyclohexyl]-4-(4-methyl-piperidin-1-yl)-4-oxobutyramide
2-{3-[4-dimethylamino-4-(4-methyl-benzyl)-cyclohexylcarbamoyl]-propionylamino}-propanoic acid-tert-butylester
5-(4-cycloheptyl-piperazin-1-yl)-5-oxo-valeric acid (4-benzyl-4-dimethylamino-cyclohexyl)-amide
Glutaric acid-(4-benzyl-4-dimethylamino-cyclohexyl)-amide [2-(4-fluoro-phenyl)-ethyl]-amide
Glutaric acid-(4-benzyl-4-dimethylamino-cyclohexyl)-amide [1-(2,6-dichloro-benzyl)-pyrrolidin-3-yl]-amide
N-[4-(4-chloro-benzyl)-4-dimethylamino-cyclohexyl]-4-(1,4-dioxa-8-aza-spiro[4.5]dec-8-yl)-4-oxo-butyramide
N-[4-(3-chloro-benzyl)-4-dimethylamino-cyclohexyl]-4-oxo-4-thiomorpholin-4-yl-butyramide
4-(4-benzoyl-piperidin-1-yl)-N-[4-dimethylamino-4-(3-methyl-benzyl)-cyclohexyl]-4-oxo-butyramide
N-[4-(4-chloro-benzyl)-4-dimethylamino-cyclohexyl]-N'-(2,4-dimethoxy-benzyl)-succinamide
N-[4-dimethylamino-4-(3-methyl-benzyl)-cyclohexyl]-N'-(1,2,3,4-tetrahydro-naphthalen-1-yl)-succinamide
N-[4-(4-chloro-benzyl)-4-dimethylamino-cyclohexyl]-N'-ethyl-N'-pyridin-4-ylmethyl-succinamide
N-[2-(3,4-dimethoxy-phenyl)-ethyl]-N'-[4-dimethylamino-4-(3-methyl-benzyl)-cyclohexyl]-N-methyl-succinamide
N-[4-(4-chloro-benzyl)-4-dimethylamino-cyclohexyl]-N'-methyl-N'-pyridin-3-ylmethyl-succinamide
N-[4-(3-chloro-benzyl)-4-dimethylamino-cyclohexyl]-N'-pyridin-2-ylmethyl-succinamide
N-[4-(3-chloro-benzyl)-4-dimethylamino-cyclohexyl]-N'-(2-methyl-benzyl)-succinamide
N-[4-dimethylamino-4-(3-methyl-benzyl)-cyclohexyl]-N'-(4-methoxy-phenyl)-succinamide N-[4-dimethylamino-4-(3-methyl-benzyl)-cyclohexyl]-N'-indan-2-yl-succinamide
N-[4-(3-chloro-benzyl)-4-dimethylamino-cyclohexyl]-N'-(1-methyl-3-phenyl-propyl)-succinamide
N-(2-chloro-6-methyl-benzyl)-N'-[4-dimethylamino -4-(3-methyl-benzyl)-cyclohexyl]-succinamide
N-[4-dimethylamino-4-(4-methyl-benzyl)-cyclohexyl]-4-[4-(4-methoxy-phenyl)-piperazin-1-yl]-4-oxo-butyramide
N-[4-dimethylamino-4-(4-methyl-benzyl)-cyclohexyl]-N'-[2-(4-fluoro-phenyl)-ethyl]-succinamide
Glutaric acid-(4-benzyl-4-dimethylamino-cyclohexyl)-amide 4-dimethylamino-benzylamide
N-[4-(3-chloro-benzyl)-4-dimethylamino-cyclohexyl]-N'-(3,5-dichloro-benzyl)-succinamide
N-[4-(4-chloro-benzyl)-4-dimethylamino-cyclohexyl]-N'-(1-methyl-3-phenyl-propyl)-succinamide
4-{3-[4-(3-chloro-benzyl)-4-dimethylamino-cyclohexylcarbamoyl]-propionyl}-piperazin-1-carboxylic acid ethylester
N-[4-dimethylamino-4-(3-methyl-benzyl)-cyclohexyl]-N'-(4-methoxy-benzyl)-succinamide
N-[4-(4-chloro-benzyl)-4-dimethylamino-cyclohexyl]-4-(2,6-dimethyl-morpholin-4-yl)-4-oxo-butyramide
N-[4-dimethylamino-4-(4-methyl-benzyl)-cyclohexyl]-4-oxo-4-(4-phenyl-3,6-dihydro-2H-pyridin-1-yl)-butyramide
N-[4-(4-chloro-benzyl)-4-dimethylamino-cyclohexyl]-N'-[2-(3-fluoro-phenyl)-ethyl]-succinamide
4-[4-(4-allyloxy-benzyl)-piperazin-1-yl]-N-[4-dimethylamino-4-(3-methyl-benzyl)-cyclohexyl]-4-oxo-butyramide
Glutaric acid-(4-benzyl-4-dimethylamino-cyclohexyl)-amide [2-(5-bromo-2-methoxy-phenyl)-ethyl]-amide
5-[4-(3-methoxy-phenyl)-piperazin-1-yl]-5-oxo-valeric acid (4-benzyl-4-dimethylamino-cyclohexyl)-amide
N-[4-(3-chloro-benzyl)-4-dimethylamino-cyclohexyl]-4-(4-methyl-piperidin-1-yl)-4-oxo-butyramide
(4-{3-[4-(4-chloro-benzyl)-4-dimethylamino-cyclohexylcarbamoyl]-propionylamino}-benzyl)-phosphonic acid diethylester
N-[4-dimethylamino-4-(4-methyl-benzyl)-cyclohexyl]-4-oxo-4-(4-o-tolyl-piperazin-1-yl)-butyramide
N-[4-dimethylamino-4-(3-methyl-benzyl)-cyclohexyl]-N'-[2-(3-fluoro-phenyl)-ethyl]-succinamide
4-[4-(4-chloro-phenyl)-piperazin-1-yl]-N-[4-dimethylamino-4-(4-methyl-benzyl)-cyclohexyl]-4-oxo-butyramide
N-[4-(3-chloro-benzyl)-4-dimethylamino-cyclohexyl]-N'-[1-(4-fluoro-phenyl)-ethyl]-succinamide
N-[4-(4-chloro-benzyl)-4-dimethylamino-cyclohexyl]-N'-[1-(4-trifluoromethyl-benzyl)-pyrrolidin-3-yl]-succinamide
N-[4-(3-chloro-benzyl)-4-dimethylamino-cyclohexyl]-N'-[2-(1H-indol-3-yl)-ethyl]-succinamide
N-[4-(4-chloro-benzyl)-4-dimethylamino-cyclohexyl]-N'-indan-5-yl-succinamide
N-(4-benzyloxy-phenyl)-N'-[4-dimethylamino-4-(4-methyl-benzyl)-cyclohexyl]-succinamide
2-{3-[4-dimethylamino-4-(3-methyl-benzyl)-cyclohexyl-carbamoyl]-propionylamino}-3-methyl-valeric acid tert-butyl ester
4-(4-benzyl-piperidin-1-yl)-N-[4-dimethylamino-4-(3-methyl-benzyl)-cyclohexyl]-4-oxo-butyramide
N-[4-(4-chloro-benzyl)-4-dimethylamino-cyclohexyl]-4-[4-(4-fluoro-phenyl)-3,6-dihydro-2H-pyridin-1-yl]-4-oxo-butyramide
N-[4-dimethylamino-4-(4-methyl-benzyl)-cyclohexyl]-N'-(1,2-dimethyl-propyl)-succinamide
N-[4-dimethylamino-4-(3-methyl-benzyl)-cyclohexyl]-4-(8-fluoro-1,3,4,5-tetrahydro-pyrido[4,3-b]indol-2-yl)-4-oxo-butyramide
4-[4-(3-chloro-benzoyl)-piperazin-1-yl]-N-[4-dimethylamino-4-(3-methyl-benzyl)-cyclohexyl]cyclohexyl]-4-oxo-butyramide
N-[4-(4-chloro-benzyl)-4-dimethylamino-cyclohexyl]-N'-(4-methoxy-phenyl)-succinamide
5-[4-(2,6-dichloro-benzyl)-piperazin-1-yl]-5-oxo-valeric acid (4-benzyl-4-dimethylamino-cyclohexyl)-amide
N-[4-dimethylamino-4-(3-methyl-benzyl)-cyclohexyl]-N'-[2-(1H-indol-3-yl)-ethyl]-N'-methyl-succinamide
N-[4-dimethylamino-4-(3-methyl-benzyl)-cyclohexyl]-N'-[1-(4-fluoro-phenyl)-ethyl]-succinamide
4-[4-(4-chloro-phenyl)-piperazin-1-yl]-N-[4-dimethylamino-4-(3-methyl-benzyl)-cyclohexyl]-4-oxo-butyramide
N-[4-(3-chloro-benzyl)-4-dimethylamino-cyclohexyl]-4-oxo-4-(4-oxo-1-phenyl-1,3,8-triaza-spiro [4.5]dec-8-yl)-butyramide
N-benzyl-N'-[4-dimethylamino-4-(3-methyl-benzyl)-cyclohexyl]-N-methyl-succinamide
N-[4-(3-chloro-benzyl)-4-dimethylamino-cyclohexyl]-N'-(3,5-difluoro-benzyl)-succinamide
N-[4-dimethylamino-4-(3-methyl-benzyl)-cyclohexyl]-N'-[2-(4-fluoro-phenyl)-ethyl]-succinamide
N-[4-dimethylamino-4-(3-methyl-benzyl)-cyclohexyl]-N'-[2-(1H-indol-3-yl)-ethyl]-succinamide
N-(2-benzylsulphanyl-ethyl)-N'-[4-dimethylamino -4-(3-methyl-benzyl)-cyclohexyl]-succinamide
N-[4-(3-chloro-benzyl)-4-dimethylamino-cyclohexyl]-N'-(2,4-difluoro-benzyl)-succinamide
N-[4-(3-chloro-benzyl)-4-dimethylamino-cyclohexyl]-N'-phenethyl-succinamide
N-[4-dimethylamino-4-(3-methyl-benzyl)-cyclohexyl]-N'-(1-naphthalen-2-yl-ethyl)-succinamide
N-[4-(3-chloro-benzyl)-4-dimethylamino-cyclohexyl]-N'-(1-methoxymethyl-2-phenyl-ethyl)-succinamide
N-[4-(3-chloro-benzyl)-4-dimethylamino-cyclohexyl]-N'-(3,4-dichloro-benzyl)-succinamide
N-[4-(3-chloro-benzyl)-4-dimethylamino-cyclohexyl]-N'-furan-2-ylmethyl-succinamide
N-[4-dimethylamino-4-(4-methyl-benzyl)-cyclohexyl]-N'-(1,2,3,4-tetrahydro-naphthalen-1-yl)-succinamide
N-[4-(3-chloro-benzyl)-4-dimethylamino-cyclohexyl]-N'-(4-fluoro-benzyl)-succinamide
N-[4-dimethylamino-4-(3-methyl-benzyl)-cyclohexyl]-N'-indan-1-yl-succinamide
N-[4-(3-chloro-benzyl)-4-dimethylamino-cyclohexyl]-4-(3,5-dimethyl-piperidin-1-yl)-4-oxo-butyramide
N-[4-dimethylamino-4-(3-methyl-benzyl)-cyclohexyl]-N'-phenethyl-succinamide
N-[4-dimethylamino-4-(4-methyl-benzyl)-cyclohexyl]-N'-phenethyl-succinamide
N-(2-benzylsulphanyl-ethyl)-N'-[4-(3-chloro-benzyl)-4-dimethylamino-cyclohexyl]-succinamide
N-[4-(3-chloro-benzyl)-4-dimethylamino-cyclohexyl]-N'-(2,5-dichloro-benzyl)-succinamide
4-[4-(3-chloro-benzoyl)-piperazin-1-yl]-N-[4-(4-chloro-benzyl)-4-dimethylamino-cyclohexyl]-4-oxo-butyramide
N-[4-(4-chloro-benzyl)-4-dimethylamino-cyclohexyl]-N'-(1-phenyl-propyl)-succinamide
N-(4-bromo-2-fluoro-benzyl)-N'-[4-dimethylamino-4-(3-methyl-benzyl)-cyclohexyl]-succinamide N-[4-(3-chloro-benzyl)-4-dimethylamino-cyclohexyl]-N'-methyl-N'-pyridin-3-ylmethyl-succinamide
N-[4-dimethylamino-4-(4-methyl-benzyl)-cyclohexyl]-N'-(2-ethoxy-benzyl)-succinamide
N-[4-dimethylamino-4-(3-methyl-benzyl)-cyclohhexyl]-N'-[2-(5-methoxy-1H-indol-3-yl)-ethyl]-succinamide
N-(4-sec-butyl-phenyl)-N'-[4-(4-chloro-benzyl)-4-dimethylamino-cyclohexyl]-succinamide
5-oxo-5-(4-phenyl-3,6-dihydro-2H-pyridin-1-yl)-valeric acid (4-benzyl-4-dimethylamino-cyclohexyl)-amide
5-oxo-5-(4-phenyl-3,6-dihydro-2H-pyridin-1-yl)-valeric acid (4-benzyl-4-dimethylamino-cyclohexyl)-amide
N-[4-(3-chloro-benzyl)-4-dimethylamino-cyclohexyl]-N'-[2-(3-fluoro-phenyl)-ethyl]-succinamide
N-(3-bromo-benzyl)-N'-[4-(3-chloro-benzyl)-4-dimethylamino-cyclohexyl]-succinamide
N-(4-bromo-2-fluoro-benzyl)-N'-[4-(3-chloro-benzyl)-4-dimethylamino-cyclohexyl]-succinamide
N-[4-(3-chloro-benzyl)-4-dimethylamino-cyclohexyl]-N'-(1-phenyl-propyl)-succinamide
N-[4-dimethylamino-4-(3-methyl-benzyl)-cyclohexyl]-N'-(4-fluoro-2-trifluoromethyl-benzyl)-succinamide
N-[4-(3-chloro-benzyl)-4-dimethylamino-cyclohexyl]-N'-indan-2-yl-succinamide
N-[4-dimethylamino-4-(3-methyl-benzyl)-cyclohexyl]-4-oxo-4-(4-phenyl-3,6-dihydro-2H-pyridin-1-yl)-butyramide
N-[4-(4-chloro-benzyl)-4-dimethylamino-cyclohexyl]-N'-[2-(2-fluoro-phenyl)-ethyl]-succinamide
N-[4-dimethylamino-4-(4-methyl-benzyl)-cyclohexyl]-N'-[2-(2-fluoro-phenyl)-ethyl]-succinamide
Glutaric acid-(4-benzyl-4-dimethylamino-cyclohexyl)-amide [2-(2-fluoro-phenyl)-ethyl]-amide
N-[2-(2-chloro-phenyl)-ethyl]-N'-[4-dimethylamino-4-(4-methyl-benzyl)-cyclohexyl]-succinamide
N-[4-(3-chloro-benzyl)-4-dimethylamino-cyclohexyl]-N'-(3,4-difluoro-benzyl)-succinamide
N-benzyl-N-(2-cyano-ethyl)-N'-[4-dimethylamino-4-(4-methyl-benzyl)-cyclohexyl]-succinamide
N-[4-(3-chloro-benzyl)-4-dimethylamino-cyclohexyl]-N'-(3-methyl-benzyl)-succinamide
N-[4-(3-chloro-benzyl)-4-dimethylamino-cyclohexyl]-N'-(4-fluoro-3-trifluoromethyl-benzyl)-succinamide
N-[4-(3-chloro-benzyl)-4-dimethylamino-cyclohexyl]-N'-[2-(2-chloro-phenyl)-ethyl]-succinamide
N-[4-(3-chloro-benzyl)-4-dimethylamino-cyclohexyl]-N'-[2-(4-chloro-phenyl)-ethyl]-succinamide
N-[4-(3-chloro-benzyl)-4-dimethylamino-cyclohexyl]-N'-[2-(2,4-dichloro-phenyl)-ethyl]-succinamide
N-[4-(3-chloro-benzyl)-4-dimethylamino-cyclohexyl]-N'-indan-1-yl-succinamide
N-[4-(4-chloro-benzyl)-4-dimethylamino-cyclohexyl]-N'-indan-1-yl-succinamide
N-[2-(4-chloro-phenyl)-propyl]-N'-[4-dimethylamino-4-(3-methyl-benzyl)-cyclohexyl]-succinamide
N-(3-bromo-benzyl)-N'-[4-(4-chloro-benzyl)-4-dimethylamino-cyclohexyl]-succinamide
N-[4-(3-chloro-benzyl)-4-dimethylamino-cyclohexyl]-N'-(3-phenyl-propyl)-succinamide
N-[4-dimethylamino-4-(4-methyl-benzyl)-cyclohexyl]-N'-(2-p-tolyl-ethyl)-succinamide
N-[4-(3-chloro-benzyl)-4-dimethylamino-cyclohexyl]-N'-(2-thiophen-2-yl-ethyl)-succinamide
Glutaric acid-(4-benzyl-4-dimethylamino-cyclohexyl)-amide [2-(4-chloro-phenyl)-propyl]-amide
N-benzyl-N'-[4-(3-chloro-benzyl)-4-dimethylamino-cyclohexyl]-N-methyl-succinamide
N-[4-(3-chloro-benzyl)-4-dimethylamino-cyclohexyl]-N'-[2-(3-chloro-phenyl)-ethyl]-succinamide
Glutaric acid-(4-benzyl-4-dimethylamino-cyclohexyl)-amide [2-(2-ethoxy-phenyl)-ethyl]-amide
Glutaric acid-(4-benzyl-4-dimethylamino-cyclohexyl)-amide phenethyl-amide
Glutaric acid-(4-benzyl-4-dimethylamino-cyclohexyl)-amide [2-(3-chloro-phenyl)-ethyl]-amide
N-[4-(3-chloro-benzyl)-4-dimethylamino-cyclohexyl]-N'-[1-(3-methoxy-phenyl)-ethyl]-succinamide
Glutaric acid-(4-benzyl-4-dimethylamino-cyclohexyl)-amide (1,3-dimethyl-butyl)-amide
N-benzyl-N'-[4-dimethylamino-4-(3-methyl-benzyl)-cyclohexyl]-N-ethyl-succinamide
N-(4-chloro-benzyl)-N'-[4-(3-chloro -benzyl)-4-dimethylamino-cyclohexyl]-succinamide
N-[4-(3-chloro-benzyl)-4-dimethylamino-cyclohexyl]-N'-[2-(2-fluoro-phenyl)-ethyl]-succinamide
N-[4-dimethylamino-4-(3-methyl-benzyl)-cyclohexyl]-N'-(2-fluoro-benzyl)-succinamide
N-[2-(4-chloro-phenyl)-ethyl]-N'-[4-dimethylamino-4-(3-methyl-benzyl)-cyclohexyl]-succinamide
N-[2-(2-chloro-phenyl)-ethyl]-N'-[4-dimethylamino-4-(3-methyl-benzyl)-cyclohexyl]-succinamide
N-[2-(3-chloro-phenyl)-ethyl]-N'-[4-dimethylamino-4-(3-methyl-benzyl)-cyclohexyl]-succinamide
N-benzyl-N'-[4-(3-chloro-benzyl)-4-dimethylamino-cyclohexyl]-N-(2-cyano-ethyl)-succinamide
N-[4-(3-chloro-benzyl)-4-dimethylamino-cyclohexyl]-N'-(3-chloro-4-fluoro-benzyl)-succinamide
N-[4-dimethylamino-4-(3-methyl-benzyl)-cyclohexyl]-N'-(2-trifluoromethyl-benzyl)-succinamide
N-[2-(2,4-dichloro-phenyl)-ethyl]-N'-[4-dimethylamino-4-(3-methyl-benzyl)-cyclohexyl]-succinamide
N-benzyl-N'-[4-(3-chloro-benzyl)-4-dimethylamino-cyclohexyl]-N-ethyl-succinamide
N-[2-(4-chloro-phenyl)-ethyl]-N'-[4-dimethylamino-4-(4-methyl-benzyl)-cyclohexyl]-succinamide
5-oxo-5-(4-o-tolyl-piperazin-1-yl)-valeric acid (4-benzyl-4-dimethylamino-cyclohexyl)-amide
N-[4-(3-chloro-benzyl)-4-dimethylamino-cyclohexyl]-N'-[3-(methyl-phenyl-amino)-propyl]-succinamide
N-[4-(3-chloro-benzyl)-4-dimethylamino-cyclohexyl]-4-[4-(5-chloro-2-methyl-phenyl)-piperazin-1-yl]-4-oxo-butyramide
N-[4-dimethylamino-4-(3-methyl-benzyl)-cyclohexyl]-N'-[2-(2-ethoxy-phenyl)-ethyl]-succinamide
4-[4-(4-chloro-benzoyl)-piperidin-1-yl]-N-[4-(3-chloro-benzyl)-4-dimethylamino-cyclohexyl]-4-oxo-butyramide
N-[4-(3-chloro-benzyl)-4-dimethylamino-cyclohexyl]-N'-[2-(2-ethoxy-phenyl)-ethyl]-succinamide
N-[2-(2,6-dichloro-phenyl)-ethyl]-N'-[4-dimethylamino-4-(3-methyl-benzyl)-cyclohexyl]-succinamide
N-benzhydryl-N'-[4-(3-chloro-benzyl)-4-dimethylamino-cyclohexyl]-succinamide
N-[4-(3-chloro -benzyl)-4-dimethylamino-cyclohexyl]-N'-cyclooctyl-succinamide
N-[4-(3-chloro-benzyl)-4-dimethylamino-cyclohexyl]-N'-[2-(4-phenoxy-phenyl)-ethyl]-succinamide
N-[4-dimethylamino-4-(3-methyl-benzyl)-cyclohexyl]-N'-(2,3-dimethyl-benzyl)-succinamide
4-[4-(5-chloro-2-methyl-phenyl)-piperazin-1-yl]-N-[4-dimethylamino-4-(3-methyl-benzyl)-cyclohexyl]-4-oxo-butyramide
4-[4-(4-chloro-benzoyl)-piperidin-1-yl]-N-[4-dimethylamino-4-(3-methyl-benzyl)-cyclohexyl]-4-oxo-butyramide N-[4-(3-chloro-benzyl)-4-dimethylamino-cyclohexyl]-N'-(1,2,3,4-tetrahydro-naphthalen-1-yl)-succinamide
N-(2-chloro-benzyl)-N'-[4-dimethylamino-4-(3-methyl-benzyl)-cyclohexyl]-succinamide
N-(2-chloro-benzyl)-N'-[4-(3-chloro-benzyl)-4-dimethylamino-cyclohexyl]-succinamide
N-[4-(3-chloro-benzyl)-4-dimethylamino-cyclohexyl]-N'-(3-fluoro-5-trifluoromethyl-benzyl)-succinamide
N-[4-(3-chloro-benzyl)-4-dimethylamino-cyclohexyl]-N'-(1-p-tolyl-ethyl)-succinamide
N-[2-(2,6-dichloro-benzylsulphanyl)-ethyl]-N'-[4-dimethylamino-4-(4-methyl-benzyl)-cyclohexyl]-succinamide
N-[4-(3-chloro-benzyl)-4-dimethylamino-cyclohexyl]-N'-[2-(2,6-dichloro-benzylsulphanyl)-ethyl]-succinamide
N-[4-(3-chloro-benzyl)-4-dimethylamino-cyclohexyl]-N'-[2-(3-trifluoromethyl-phenyl)-ethyl]-succinamide
N-[2-(3,4-dichloro-phenyl)-ethyl]-N'-[4-dimethylamino-4-(3-methyl-benzyl)-cyclohexyl]-succinamide
N-[4-(3-chloro-benzyl)-4-dimethylamino-cyclohexyl]-4-[4-(2-fluoro-phenyl)-piperazin-1-yl]-4-oxo-butyramide
5-[4-(2,4-dimethoxy-phenyl)-piperazin-1-yl]-5-oxo-valeric acid (4-benzyl-4-dimethylamino-cycloh
N-[4-(3-chloro-benzyl)-4-dimethylamino-cyclohexyl]-N'-(1-naphthalen-1-yl-ethyl)-succinamide
N-[4-dimethylamino-4-(3-methyl-benzyl)-cyclohexyl]-N'-(1-naphthalen-1 -yl-ethyl)-succinamide
N-[4-(3-chloro-benzyl)-4-dimethylamino-cyclohexyl]-N'-(2-fluoro-benzyl)-N'-furan-2-ylmethyl-succinamide
N-[4-dimethylamino-4-(3-methyl-benzyl)-cyclohexyl]-N'-(2-fluoro-benzyl)-N'-furan-2-ylmethyl-succinamide
N-[4-(3-chloro-benzyl)-4-dimethylamino-cyclohexyl]-N'-(2,5-dimethoxy-benzyl)-N'-furan-2-ylmethyl-succinamide
N-(4-azepan-1-yl-4-benzyl-cyclohexyl)-4-(2,3-dihydro-indol-1-yl)-4-oxo-butyramide
4-(2,3-dihydro-indol-1-yl)-N-[4-dimethylamino-4-(3-fluoro-phenyl)-cyclohexyl]-4-oxo-butyramide
N-(4-benzyl-4-morpholin-4-yl-cyclohexyl)-N'-(2-chloro-6-methyl-benzyl)-succinamide
N-(4-benzyl-4-morpholin-4-yl-cyclohexyl)-N'-[2-(3-methoxy-phenyl)-ethyl]-succinamide
N-(4-benzyl-4-morpholin-4-yl-cyclohexyl)-N'-(3-methylbenzyl)-succinamide
N-(4-benzyl-4-morpholin-4-yl-cyclohexyl)-N'-(4-bromo-2-fluoro-benzyl)-succinamide
N-(4-benzyl-4-morpholin-4-yl-cyclohexyl)-N'-pyridin-4-ylmethyl-succinamide
N-(4-benzyl-4-morpholin-4-yl-cyclohexyl)-N'-indan-1-yl-succinamide
N-(4-benzyl-4-morpholin-4-yl-cyclohexyl)-N'-(2,4-dimethoxy-benzyl)-succinamide
N-(4-benzyl-4-morpholin-4-yl-cyclohexyl)-N'-thiophen-2-ylmethyl-succinamide
N-adamantan-1-ylmethyl-N'-(4-benzyl-4-morpholin-4-yl-cyclohexyl)-succinamide
N-(4-benzyl-4-morpholin-4-yl-cyclohexyl)-N'-(2,5-difluoro-benzyl)-succinamide
N-(4-benzyl-4-morpholin-4-yl-cyclohexyl)-N'-(4-tert-butyl-phenyl)-succinamide
N-(4-benzyl-4-morpholin-4-yl-cyclohexyl)-N'-(3,5-bis-trifluoromethyl-benzyl)-succinamide
N-(4-benzyl-4-morpholin-4-yl-cyclohexyl)-N'-[2-(2-ethoxy-phenyl)-ethyl]-succinamide
N-(4-benzyl-4-morpholin-4-yl-cyclohexyl)-N'-(3-methoxypropyl)-succinamide
N-(4-benzyl-4-morpholin-4-yl-cyclohexyl)-N'-(2-morpholin-4-yl-ethyl)-succinamide
N-(4-benzyl-4-morpholin-4-yl-cyclohexyl)-N'-(2,5-dichloro-benzyl)-succinamide
N-(4-benzyl-4-morpholin-4-yl-cyclohexyl)-N'-[1-(2-benzyloxy-benzyl)-pyrrolidin-3-yl]-N'-methyl-succinamide
N-(4-benzyl-4-morpholin-4-yl-cyclohexyl)-4-oxo-4-(2-pyrrolidin-1-ylmethyl-pyrrolidin-1-yl)-butyramide
N-(4-benzyl-4-morpholin-4-yl-cyclohexyl)-4-morpholin-4-yl-4-oxo-butyramide
N-(4-benzyl-4-morpholin-4-yl-cyclohexyl)-N'-(3-dimethylamino-propyl)-N'-methyl-succinamide
N-(4-benzyl-4-morpholin-4-yl-cyclohexyl)-N'-(2-phenyl-cyclopropyl)-succinamide
N-(4-benzyl-4-morpholin-4-yl-cyclohexyl)-N'-naphthalen-1-ylmethyl-succinamide
N-(4-benzyl-4-morpholin-4-yl-cyclohexyl)-4-(4-methyl-[1,4]diazepan-1-yl)-4-oxo-butyramide
N-(4-benzyl-4-morpholin-4-yl-cyclohexyl)-4-(4-hydroxy-piperidin-1-yl)-4-oxo-butyramide
N-(4-benzyl-4-morpholin-4-yl-cyclohexyl)-N'-[2-(7-methyl-1H-indol-3-yl)-ethyl]-succinamide
N-(4-benzyl-4-morpholin-4-yl-cyclohexyl)-N'-[2-(5-methoxy-1H-indol-3-yl)-ethyl]-succinamide
N-(4-benzyl-4-morpholin-4-yl-cyclohexyl)-4-oxo-4-(4-quinolin-2-ylmethyl-piperazin-1-yl)-butyramide
N-(4-dimethylamino-4-thiophen-2-yl-cyclohexyl)-4-oxo-4-[4-(5-trifluoromethyl-pyridin-2-yl)-piperazin-1-yl]-butyramide
Glutaric acid-(1-adamantan-1-yl-ethyl)-amide (4-dimethylamino-4-thiophen-2-yl-cyclohexyl)-amide
N-[2-(2,6-dichloro-phenyl)-ethyl]-N'-(4-dimethylamino-4-thiophen-2-yl-cyclohexyl)-succinamide
N-(4-dimethylamino-4-thi thiophen-2-yl-cyclohexyl)-N'-(1-methyl-3-phenyl-propyl)-succinamide
N-benzyl-N'-(4-dimethylamino-4-thiophen-2-yl-cyclohexyl)-N-ethyl-succinamide
N-[2-(4-bromo-phenyl)-ethyl]-N'-(4-dimethylamino-4-thiophen-2-yl-cyclohexyl)-succinamide
4-[4-(4-chloro-benzoyl)-piperidin-1-yl]-N-(4-dimethylamino-4-thiophen-2-yl-cyclohexyl)-4-oxo-butyramide
Glutaric acid-[1-(2,6-dichloro-benzyl)-pyrrolidin-3-yl]-amide (4-dimethylamino-4-thiophen-2-yl-cyclohexyl)-amide
Glutaric acid-(4-dimethylamino-4-thiophen-2-yl-cyclohexyl)-amide (3-phenyl-propyl)-amide
N-(4-dimethylamino-4-phenyl-cyclohexyl)-N'-pentyl-succinamide
3-(4-chloro-phenyl)-2-[4-(4-dimethylamino-4-thiophen-2-yl-cyclohexylcarbamoyl)-butyrylamino]-propanoic acid ethylester
Glutaric acid-(4-dimethylamino-4-thiophen-2-yl-cyclohexyl)-amide indan-1-ylamide
N-adamantan-1-ylmethyl-N'-(4-dimethylamino-4-thiophen-2-yl-cyclohexyl)-succinamide
5-(4-benzofuran-2-ylmethyl-piperazin-1-yl)-5-oxo-valeric acid (4-dimethylamino-4-thiophen-2-yl-cyclohexyl)-amide
4-[4-(4-tert-butyl-benzyl)-piperazin-1-yl]-N-(4-dimethylamino-4-phenyl-cyclohexyl)-4-oxo-butyramide
Glutaric acid-(4-dimethylamino-4-thiophen-2-yl-cyclohexyl)-amide [2-(1H-indol-3-yl)-ethyl]-amide
N-(4-dimethylamino-4-phenyl-cyclohexyl)-4-[4-hydroxy-4-(3-trifluoromethyl-phenyl)-piperidin-1-yl]-4-oxo-butyramide
5-(3,4-dihydro-1H-isoquinolin-2-yl)-5-oxo-valeric acid (4-dimethylamino-4-thiophen-2-yl-cyclohexyl)-amide
4-(4-benzyl-piperidin-1-yl)-N-(4-dimethylamino-4-phenyl-cyclohexyl)-4-oxo-butyramide {[4-(4-dimethylamino -4-thiophen-2-yl-cyclohexylcarbamoyl)-butyryl]-methyl-amino}-acetic acid benzylester
N-benzyl-N'-(4-dimethylamino-4-phenyl-cyclohexyl)-N-phenethyl-succinamide
Glutaric acid-(4-dimethylamino-4-thiophen-2-yl-cyclohexyl)-amide 3-trifluoromethoxy-benzylamide
Glutaric acid-(4-dimethylamino-4-thiophen-2-yl-cyclohexyl)-amide ethyl-(2-methyl-allyl)-amide
N,N-bis-(2-cyano-ethyl)-N'-(4-dimethylamino-4-thiophen-2-yl-cyclohexyl)-succinamide
Glutaric acid-benzyl-methyl-amide (4-dimethylamino-4-thiophen-2-yl-cyclohexyl)-amide
Glutaric acid-(2-benzyloxy-cyclopentyl)-amide (4-dimethylamino-4-thiophen-2-yl-cyclohexyl)-amide
Glutaric acid-(4-dimethylamino-4-thiophen-2-yl-cyclohexyl)-amide 4-trifluoromethyl-benzylamide
N-(4-dimethylamino-4-thiophen-2-yl-cyclohexyl)-N'-[2-(4-phenoxy-phenyl)-ethyl]-succinamide
Glutaric acid-(4-dimethylamino-4-thiophen-2-yl-cyclohexyl)-amide (3,3-diphenyl-propyl)-amide
4-(4-benzyl-piperidin-1-yl)-N-(4-dimethylamino-4-thiophen-2-yl-cyclohexyl)-4-oxo-butyramide
N-(4-dimethylamino-4-thiophen-2-yl-cyclohexyl)-4-[4-hydroxy-4-(3-trifluoromethyl-phenyl)-piperidin-1-yl]-4-oxo-butyramide
Glutaric acid-(4-dimethylamino-4-thiophen-2-yl-cyclohexyl)-amide 4-fluoro-2-trifluoromethyl-benzylamide
N-(4-dimethylamino-4-thiophen-2-yl-cyclohexyl)-N'-pentyl-succinamide
5-[4-(2-methoxy-naphthalen-1-ylmethyl)-piperazin-1-yl]-5-oxo-valeric acid (4-dimethylamino-4-thiophen-2-yl-cyclohexyl)-amide
N-(4-dimethylamino-4-thiophen-2-yl-cyclohexyl)-N'-(2-ethoxy-benzyl)-N'-furan-2-ylmethyl-succinamide
Glutaric acid-(4-dimethylamino-4-thiophen-2-yl-cyclohexyl)-amide (2-phenyl-cyclopropyl)-amide
N-[2-(3,4-dichloro-phenyl)-ethyl]-N'-(4-dimethylamino-4-phenyl-cyclohexyl)-succinamide
N-adamantan-1-ylmethyl-N'-(4-dimethylamino-4-phenyl-cyclohexyl)-succinamide 5-[4-(4-fluoro-phenyl)-3,6-dihydro-2H-pyridin-1-yl]-5-oxo-valeric acid (4-dimethylamino-4-thiophen-2-yl-cyclohexyl)-amide
2-[4-(4-dimethylamino-4-thiophen-2-yl-cyclohexylcarbamoyl)-butyrylamino]-4-methyl-valeric acid benzyl ester
{4-[4-(4-dimethylamino-4-thiophen-2-yl-cyclohexylcarbamoyl)-butyrylamino]-phenyl}-carbamic acid-tert-butylester
Glutaric acid-(4-dimethylamino-4-thiophen-2-yl-cyclohexyl)-amide [2-(3-methoxy-phenyl)-ethyl]-amide
Glutaric acid-benzyl-ethyl-amide (4-dimethylamino-4-thiophen-2-yl-cyclohexyl)-amide
Glutaric acid-3-chloro-benzylamide (4-dimethylamino-4-thiophen-2-yl-cyclohexyl)-amide
Glutaric acid-(4-dimethylamino-4-thiophen-2-yl-cyclohexyl)-amide (4-methyl-cyclohexyl)-amide
N-(4-dimethylamino-4-phenyl-cyclohexyl)-N'-[2-(1H-indol-3-yl)-ethyl]-N'-methyl-succinamide
Glutaric acid-2,5-dichloro-benzylamide (4-dimethylamino-4-thiophen-2-yl-cyclohexyl)-amide
Glutaric acid-(4-dimethylamino-4-thiophen-2-yl-cyclohexyl)-amide [2-(3-fluoro-phenyl)-ethyl]-amide
N-(4-dimethylamino-4-phenyl-cyclohexyl)-N'-[2-(4-methoxy-phenoxy)-ethyl]-succinamide
N-(4-dimethylamino-4-thiophen-2-yl-cyclohexyl)-N'-[2-(ethyl-m-tolyl-amino)-ethyl]-succinamide
Glutaric acid-(4-benzyloxy-phenyl)-amide (4-dimethylamino-4-thiophen-2-yl-cyclohexyl)-amide
Glutaric acid-(4-dimethylamino-4-thiophen-2-yl-cyclohexyl)-amide [2-(4-fluoro-phenyl)-ethyl]-amide
Glutaric acid-[2-(4-bromo-phenyl)-ethyl]-amide (4-dimethylamino-4-thiophen-2-yl-cyclohexyl)-amide
N-(4-dimethylamino-4-thiophen-2-yl-cyclohexyl)-N'-(4-phenoxy-phenyl)-succinamide
N-(4-dimethylamino-4-phenyl-cyclohexyl)-N'-[2-(3-trifluoromethyl-phenyl)-ethyl]-succinamide
Glutaric acid-[2-(4-chloro-phenyl)-propyl]-amide (4-dimethylamino-4-thiophen-2-yl-cyclohexyl)-amide
N-(4-dimethylamino-4-thiophen-2-yl-cyclohexyl)-N'-[2-(1H-indol-3-yl)-ethyl]-N'-methyl-succinamide
N-(4-dimethylamino-4-thiophen-2-yl-cyclohexyl)-N'-[2-(4-methoxy-phenoxy)-ethyl]-succinamide
Glutaric acid-(4-dimethylamino-4-thiophen-2-yl-cyclohexyl)-amide (3-phenoxy-phenyl)-amide
N-(4-dimethylamino-4-phenyl-cyclohexyl)-N'-[2-(ethyl-m-tolyl-amino)-ethyl]-succinamide
Glutaric acid-[2-(5-bromo-2-methoxy-phenyl)-ethyl]-amide (4-dimethylamino-4-thiophen-2-yl-cyclohexyl)-amide
N-(4-dimethylamino-4-thiophen-2-yl-cyclohexyl)-N'-[2-(3-trifluoromethyl-phenyl)-ethyl]-succinamide
Glutaric acid-(4-dimethylamino-4-thiophen-2-yl-cyclohexyl)-amide (1-methyl-3-phenyl-propyl)-amide
N-[2-(2,6-dichloro-benzylsulphanyl)-ethyl]-N'-(4-dimethylamino-4-thiophen-2-yl-cyclohexyl)-succinamide
Glutaric acid-(4-dimethylamino-4-thiophen-2-yl-cyclohexyl)-amide (2,2-diphenyl-propyl)-amide
N-(4-dimethylamino-4-thiophen-2-yl-cyclohexyl)-N'-[3-(methyl-phenyl-amino)-propyl]-succinamide
N-(1-biphenyl-4-ylmethyl-pyrrolidin-3-yl)-N'-(4-dimethylamino -4-thiophen-2-yl-cyclohexyl)-N-methyl-succinamide
Glutaric acid-[4-(cyano-phenyl-methyl)-phenyl]-amide (4-dimethylamino-4-thiophen-2-ylcyclohexyl)-amide
Glutaric acid-(4-tert-butyl-cyclohexyl)-amide (4-dimethylamino-4-thiophen-2-yl-cyclohexyl)-amide
Glutaric acid-(4-sec-butyl-phenyl)-amide (4-dimethylamino-4-thiophen-2-yl-cyclohexyl)-amide
Glutaric acid-(4-butyl-phenyl)-amide (4-dimethylamino-4-thiophen-2-yl-cyclohexyl)-amide
N-(2-benzylsulphanyl-ethyl)-N'-(4-dimethylamino-4-thiophen-2-yl-cyclohexyl)-succinamide
N-(4-dimethylamino-4-thiophen-2-yl-cyclohexyl)-N'-(2-phenoxy-ethyl)-succinamide
Glutaric acid-(4-dimethylamino-4-thiophen-2-yl-cyclohexyl)-amide (naphthalen-1-ylmethyl)-amide
Glutaric acid-3-bromo-benzylamide (4-dimethylamino-4-thiophen-2-yl-cyclohexyl)-amide
N-(4-dimethylamino-4-thiophen-2-yl-cyclohexyl)-N'-(3-phenyl-propyl)-succinamide
N-[2-(3-chloro-phenyl)-ethyl]-N'-(4-dimethylamino-4-phenyl-cyclohexyl)-succinamide
2-[3-(4-dimethylamino-4-thiophen-2-yl-cyclohexylcarbamoyl)-propionylamino]-propanoic acid benzylester
N-[2-(2-chloro-phenyl)-ethyl]-N'-(4-dimethylamino-4-phenyl-cyclohexyl)-succinamide
N-(4-dimethylamino-4-phenyl-cyclohexyl)-N'-[2-(3-fluoro-phenyl)-ethyl]-succinamide
Glutaric acid-(4-dimethylamino-4-thiophen-2-yl-cyclohexyl)-amide (2-thiophen-2-yl-ethyl)-amide
Glutaric acid-(4-dimethylamino-4-thiophen-2-yl-cyclohexyl)-amide [2-(4-phenoxy-phenyl)-ethyl]-amide
N-[2-(4-chloro-phenyl)-ethyl]-N'-(4-dimethylamino-4-phenyl-cyclohexyl)-succinamide
N-[2-(3-chloro-phenyl)-ethyl]-N'-(4-dimethylamino -4-thiophen-2-yl-cyclohexyl)-succinamide N-benzyl-N'-(4-dimethylamino-4-thiophen-2-yl-cyclohexyl)-N-ethyl-succinamide Glutaric acid-[1-(2,6-dichloro-benzyl)-pyrrolidin-3-yl]-amide (4-dimethylamino-4-thiophen-2-yl-cyclohexyl)-amide Glutaric acid-(4-dimethylamino-4-thiophen-2-yl-cyclohexyl)-amide (3-phenyl-propyl)-amide Glutaric acid-(4-dimethylamino-4-thiophen-2-yl-cyclohexyl)-amide [2-(1H-indol-3-yl)-ethyl]-amide 5-(3,4-dihydro-1H-isoquinolin-2-yl)-5-oxo-valeric acid (4-dimethylamino-4-thiophen-2-yl-cyclohexyl)-amide {[4-(4-dimethylamino-4-thiophen-2-yl-cyclohexylcarbamoyl)-butyryl]-methyl-amino}-acetic acid benzylester N-(4-dimethylamino-4-thiophen-2-yl-cyclohexyl)-N'-[2-(4-phenoxy-phenyl)-ethyl]-succinamide Glutaric acid-(4-dimethylamino-4-thiophen-2-yl-cyclohexyl)-amide (2-phenyl-cyclopropyl)-amide N-[4-(3-chlorobenzyl)-4-dimethylaminocyclohexyl]-N'-furan-2-ylmethylsuccinic acid amide hydrochloride, non-polar diastereoisomer N-[4-(3-chlorobenzyl)-4-dimethylaminocyclohexyl]-N'-furan-2-ylmethylsuccinic acid amide hydrochloride, polar diastereoisomer Glutaric acid (4-benzyl-4-dimethylaminocyclohexyl)amide [2-(2-fluorophenyl)ethyl]amide hydrochloride, non-polar diastereoisomer Glutaric acid (4-benzyl-4-dimethylaminocyclohexyl)amide [2-(2-fluorophenyl)ethyl] amide hydrochloride, polar diastereoisomer N-[4-(3-chlorobenzyl)-4-dimethylaminocyclohexyl]-N'-[2-(4-chlorophenyl)ethyl]-succinic acid amide hydrochloride, non-polar diastereoisomer N-[4-(3-chlorobenzyl)-4-dimethylaminocyclohexyl]-N'-[2-(4-chlorophenyl)ethyl]-succinic acid amide hydrochloride, polar diastereoisomer Glutaric acid (4-benzyl-4-dimethylaminocyclohexyl)amide [2-(4-chlorophenyl)ethyl]amide hydrochloride, non-polar diastereoisomer in the form of the racemate; the enantiomers, diastereomers, mixtures of the enantiomers or diastereomers or an individual enantiomer or diastereomer; the bases and/or salts of physiologically acceptable acids or cations.

The substances according to the invention act, for example, on the ORL1 receptor that is relevant in connection with various diseases, so they are suitable as a pharmaceutical active ingredient in a pharmaceutical composition. The invention therefore further relates to pharmaceutical compositions containing at least one substituted cyclohexyl carboxylic acid derivative according to the invention, and optionally suitable additives and/or auxiliaries and/or optionally further active ingredients.

The pharmaceutical compositions according to the invention contain, in addition to at least one substituted cyclohexyl-1,4-diamine derivative according to the invention, optionally suitable additives and/or auxiliaries, therefore also excipients, fillers, solvents, diluents, dyes and/or binders and can be administered as liquid pharmaceutical compositions in the form of injection solutions, drops or syrups, as semi-solid pharmaceutical compositions in the form of granules, tablets, pellets, patches, capsules, plasters or aerosols. The choice of auxiliaries, etc. and the amounts thereof to be used depend on whether the pharmaceutical composition is to be applied orally, perorally, parenterally, intravenously, intraperitoneally, intradermally, intramuscularly, intranasally, buccally, rectally or topically, for example to the skin, the mucous membranes or the eyes. Preparations in the form of tablets, dragees, capsules, granules, drops, juices and syrups are suitable for oral application, solutions, suspensions, easily reconstitutable dry preparations and sprays are suitable for parenteral, topical and inhalative applications. Substituted cyclohexyl-1,4-diamine derivatives according to the invention in a deposit, in dissolved form or in a plaster, optionally with the addition of agents to promote skin penetration, are suitable percutaneous application preparations. Orally or percutaneously applicable preparation forms can release the substituted cyclohexyl-1,4-diamine derivatives according to the invention after a delay. The substituted cyclohexyl-1,4-diamine derivatives according to the invention may also be applied in the form of parenteral long-acting repositories such as implants or implanted pumps. In principle, further active ingredients known to the person skilled in the art can be added to the pharmaceutical compositions according to the invention.

The amount of active ingredient to be administered to the patient varies as a function of the weight of the patient, the method of application, the indication and the severity of the illness. Conventionally, 0.00005 to 50 mg/kg, preferably 0.01 to 5 mg/kg, of at least one substituted cyclohexyl-1,4-diamine derivative according to the invention are applied.

For all of the above-mentioned forms of the pharmaceutical composition according to the invention, it is particularly preferred if, in addition to at least one substituted cyclohexyl-1,4-diamine derivative, the pharmaceutical composition contains a further active ingredient, in particular an opioid, preferably a strong opioid, in particular morphine, or an anaesthetic, preferably hexobarbital or halothane.

In a preferred form of the pharmaceutical composition, a contained substituted cyclohexyl-1,4-diamine derivative according to the invention is in the form of a pure diastereomer and/or enantiomer, as a racemate or as a non-equimolar or equimolar blend of the diastereomers and/or enantiomers.

Both the ORL1 receptor and the further opioid receptors have been identified in particular in the occurrence of pain. Accordingly, substituted cyclohexyl-1,4-diamine derivatives according to the invention can be used for producing a pharmaceutical composition for the treatment of pain, in particular acute, neuropathic or chronic pain.

The invention therefore further relates to the use of a substituted cyclohexyl-1,4-diamine derivative according to the invention for producing a pharmaceutical composition for treating pain, in particular acute, visceral, neuropathic or chronic pain.

The invention further relates to the use of a substituted cyclohexyl-1,4-diamine derivative according to the invention for the production of a pharmaceutical composition for the treatment of anxiety, stress and stress-related syndromes, depression, epilepsy, Alzheimer's disease, senile dementia, catalepsy, general cognitive dysfunction, learning and memory disorders (as a nootropic), withdrawal symptoms, alcohol- and/or drug- and/or medicine abuse and/or dependency, sexual dysfunction, cardiovascular diseases, hypotension, hypertension, tinnitus, pruritus, migraine, hearing difficulties, deficient intestine motility, impaired absorption of nutrients, anorexia, obesity, locomotive disorders, diarrhoea, cachexia, urinary incontinence, or as a muscle relaxant, anticonvulsive or anaesthetic or for co-administration in treatment with an opioid analgesic or anaesthetic, for diuresis or anti-natriuresis, anxiolysis, for modulation of motor activity, for modulation of neurotransmitter release and treatment of neurodegenerative diseases connected therewith, for the treatment of withdrawal symptoms and/or for reducing opioid addiction potential.

In this case it may be preferred in one of the present uses if a substituted cyclohexyl-1,4-diamine derivative used is in the form of a pure diastereomer and/or enantiomer, as a racemate or as a non-equimolar or equimolar blend of the diastereomers and/or enantiomers.

The invention further relates to a process for the treatment, in particular in one of the above-mentioned indications, of a non-human mammal or human, which or who requires treatment of pain, in particular chronic pain, by administration of a therapeutically effective dose of a substituted cyclohexyl-1,4-diamine derivative according to the invention, or of a pharmaceutical composition according to the invention.

The invention further relates to a process for producing the substituted cyclohexyl-1,4-diamine derivatives according to the invention, as stated in the following description and examples.

The radicals $R^{01}$ and $R^{02}$ have the meaning given for compounds according to the invention of formula I for $R^1$ and $R^2$ and, in addition, independently of one another can represent a protecting group. The remaining radicals have the meaning indicated in formula I:

mentary primary or secondary amine or a cyclohexane-1,4-diamine in the presence of dehydrating agents. In the second step, in particular, it may be advantageous to activate the carboxylic acid function of the intermediate semi-amide before producing the diamide by conversion into a carboxylic acid equivalent (for example acid chloride or active ester). The reactions with anhydrides preferably take place in polar or non-polar aprotic solvents such as DMF, DMSO, diethyl ether, diisopropylether, THF, toluene, dichloromethane or acetonitrile at temperatures between −20 and +110° C., preferably between −10 and +40° C.

In the case of reactions with acid chlorides, polar or non-polar aprotic solvents, to which an organic or inorganic auxiliary base, preferably tertiary amines such as triethylamine, diisopropylethylamine or DMAP, has been added, are also used. In addition to amines of this type, pyridine, for example, is also suitable as a base and as a solvent. Preferably acid

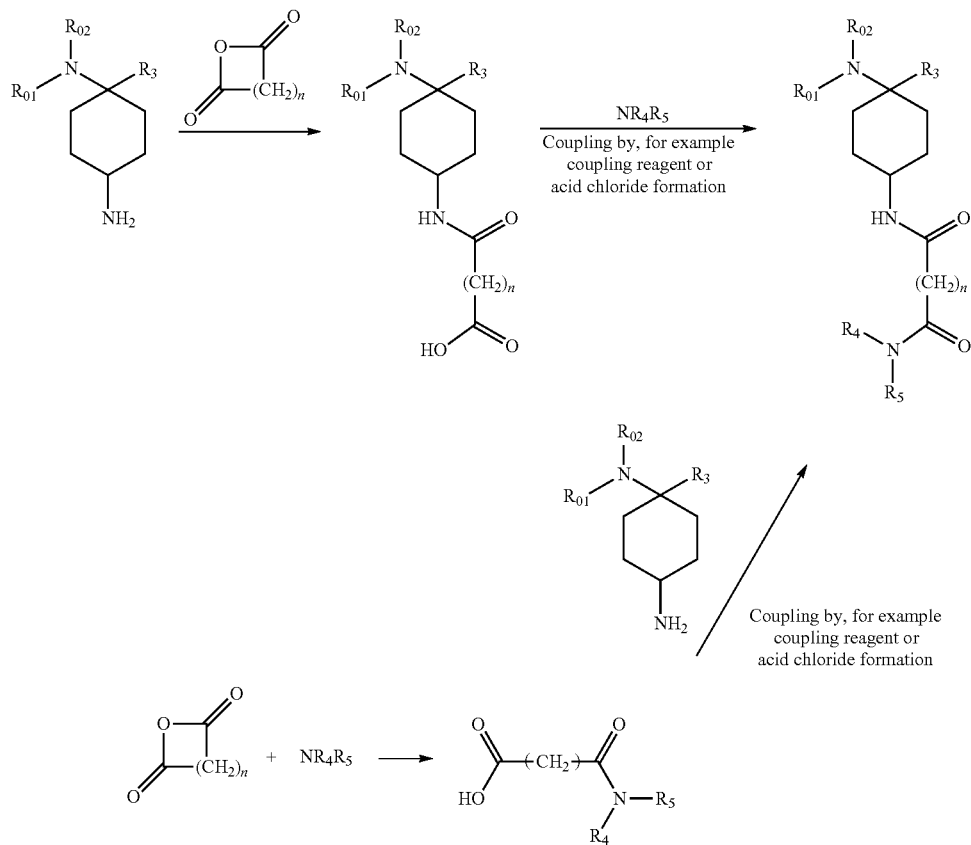

Basically the various methods known to a person skilled in the art for producing amides are suitable for preparing the diamides according to the invention. The process according to the invention involves linking substituted cyclohexane-1,4-diamines (WO 02090317) via anhydrides, open-chain dicarboxylic acids or preferably the activated analogues thereof, in particular the acid halides thereof, with further primary or secondary amines and thus converting them into compounds according to the invention. Preferably anhydrides are initially opened with a cyclohexane-1,4-diamine or a primary or secondary amine to form the corresponding semi-amides, before being reacted in the second step to the diamide by a complechlorides are reacted with amines at −10 and +40° C. in dichloromethane or chloroform in the presence of triethylamine or pyridine and optionally catalytic amounts of DMAP. For the reaction of the carboxylic acid function of an intermediate semi-amide with a further amine, the entire range of methods for producing amides known to a person skilled in the art is available. Organic or inorganic dehydrating agents such as a molecular sieve, magnesium sulphate, sulphuric acid or carbodiimides such as DCC or DIC, the latter optionally in the presence of HOBt (1-hydroxybenzotriazole), are advantageously used. These reactions are also preferably conducted in polar or non-polar aprotic solvents at temperatures between −20 and +110° C., preferably between −10 and +40° C. The protecting groups are optionally then cleaved.

EXAMPLES

Certain embodiments of the present invention may be further understood by reference to the following specific examples. These examples and the terminology used herein are for the purpose of describing particular embodiments only and are not intended to be limiting.

The yields of compounds produced have not been optimised.

All temperatures are uncorrected.

The term "ether" denotes diethyl ether, "EE" ethyl acetate and "DCM" dichloromethane. The term "equivalent" denotes amount of substance equivalent, "mp." melting point or melting range, "decomp." decomposition, "RT" room temperature, "abs." absolute (anhydrous), "rac." racemic, "conc." concentrated, "min" minutes, "h" hours, "d" days, "vol. %" volume percent, "m %" mass percent and "M" is a concentration in mol/l.

Silica gel 60 (0.040-0.063 mm) from E. Merck, Darmstadt was used as the stationary phase for column chromatography.

Thin-layer chromatography tests were carried out using HPTLC chromatoplates, silica gel 60 F 254, from E. Merck, Darmstadt.

The mixing ratios of eluants for chromatographic tests are always given in volume/volume.

The compounds used in the following were either commercially available, or production thereof is known from the prior art or has been derived from the prior art in a manner obvious to a person skilled in the art.

General Directions:

0.1 mmol cyclohexane-1,4-diamine and 0.1 mmol diisopropylethylamine in THF were added dropwise to 0.1 mmol of the anhydride. The mixture was stirred for 12 h and 2 M HCl were then added to the reaction solution. The carboxylic acid derivative was obtained by extraction with 3×2 ml dichloromethane and removal of the solvent.

0.1 mmol of the corresponding amine (see Table 1) and 1 equivalent dilsopropylcarbodiimide and 1 equivalent 1-hydroxybenzotriazole were added to the resultant product. The mixture was stirred for 12 h and a 1 M sodium carbonate solution was then added. The product was obtained by extraction with 3×2 ml ethyl acetate/THF in each case and removal of the solvent.

Table 1 cites the carboxylic acids used for the last step for the examples.

TABLE 1

List of examples and diagrams of the amine used in the last synthesis step.

| Example | | Name of example compound |
|---|---|---|
| 1 | [structure: 3-aminopyrrolidine with 2,6-dichlorobenzyl on N] | N-[1-(2,6-dichloro-benzyl)-pyrrolidin-3-yl]-N'-[4-dimethylamino-4-(4-methyl-benzyl)-cyclohexyl]-succinamide |
| 2 | [structure: 3-amino-dihydrofuran-2(3H)-one] | N-[4-(3-chloro-benzyl)-4-dimethylamino-cyclohexyl]-N'-(2-oxo-tetrahydro-furan-3-yl)-succinamide |
| 3 | [structure: 3,3-diphenylpropylamine] | N-[4-(4-chloro-benzyl)-4-dimethylamino-cyclohexyl]-N'-(3,3-diphenyl-propyl)-succinamide |
| 4 | [structure: piperazine with (7-methoxy-benzo[1,3]dioxol-5-ylmethyl) group] | N-[4-dimethylamino-4-(4-methyl-benzyl)-cyclohexyl]-4-[4-(7-methoxy-benzo[1,3]dioxol-5-ylmethyl)-piperazin-1-yl]-4-oxo-butyramide |

TABLE 1-continued

List of examples and diagrams of the amine used in the last synthesis step.

| Example | | Name of example compound |
|---|---|---|
| 5 |  | N-[4-(4-chloro-benzyl)-4-dimethylamino-cyclohexyl]-4-(3,6-dihydro-2H-pyridin-1-yl)-4-oxo-butyramide |
| 6 | 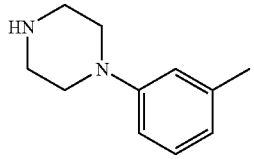 | N-[4-dimethylamino-4-(4-methyl-benzyl)-cyclohexyl]-4-oxo-4-(4-m-tolyl-piperazin-1-yl)-butyramide |
| 7 | 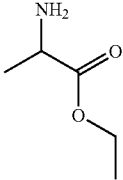 | 2-{3-[4-(4-chloro-benzyl)-4-dimethylamino-cyclohexylcarbamoyl]-propionylamino}-propanoic acid ethylester |
| 8 |  | N-[4-(3-chloro-benzyl)-4-dimethylamino-cyclohexyl]-4-(8-fluoro-1,3,4,5-tetrahydro-pyrido[4,3-b]indol-2-yl)-4-oxo-butyramide |
| 9 | 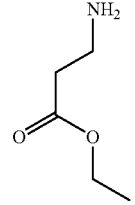 | 3-{3-[4-dimethylamino-4-(4-methyl-benzyl)-cyclohexylcarbamoyl]-propionylamino}-propanoic acid ethylester |
| 10 | 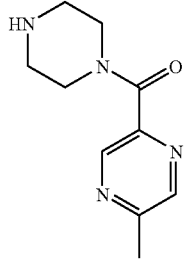 | N-[4-dimethylamino-4-(4-methyl-benzyl)-cyclohexyl]-4-[4-(5-methyl-pyrazin-2-carbonyl)-piperazin-1-yl]-4-oxo-butyramide |
| 11 | 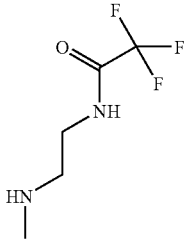 | N-[4-dimethylamino-4-(4-methyl-benzyl)-cyclohexyl]-N'-methyl-N'-[2-(2,2,2-trifluoro-acetylamino)-ethyl]-succinamide |

TABLE 1-continued

List of examples and diagrams of the amine used in the last synthesis step.

| Example | | Name of example compound |
|---|---|---|
| 12 | 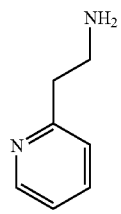 | N-[4-(3-chloro-benzyl)-4-dimethylamino-cyclohexyl]-N'-(2-pyridin-2-yl-ethyl)-succinamide |
| 13 | 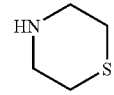 | N-[4-(4-chloro-benzyl)-4-dimethylamino-cyclohexyl]-4-oxo-4-thiomorpholin-4-yl-butyramide |
| 14 | 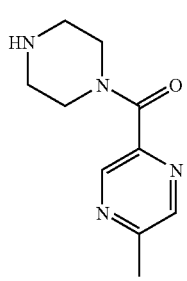 | N-[4-(4-chloro-benzyl)-4-dimethylamino-cyclohexyl]-4-[4-(5-methyl-pyrazin-2-carbonyl)-piperazin-1-yl]-4-oxo-butyramide |
| 15 | 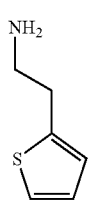 | N-[4-dimethylamino-4-(3-methyl-benzyl)-cyclohexyl]-N'-(2-thiophen-2-yl-ethyl)-succinamide |
| 16 | 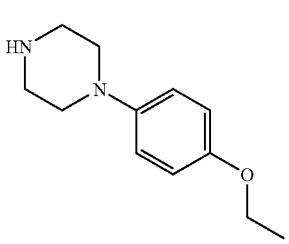 | N-[4-(4-chloro-benzyl)-4-dimethylamino-cyclohexyl]-4-[4-(4-ethoxy-phenyl)-piperazin-1-yl]-4-oxo-butyramide |
| 17 | 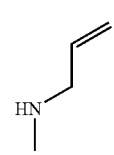 | N-allyl-N'-[4-(4-chloro-benzyl)-4-dimethylamino-cyclohexyl]-N-methyl-succinamide |
| 18 | 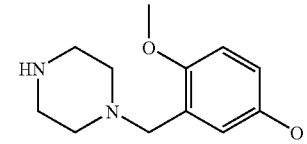 | 5-[4-(2,5-dimethoxy-benzyl)-piperazin-1-yl]-5-oxo-valeric acid (4-benzyl-4-dimethylamino-cyclohexyl)-amide |
| 19 | 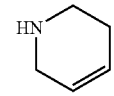 | 4-(3,6-dihydro-2H-pyridin-1-yl)-N-[4-dimethylamino-4-(4-methyl-benzyl)-cyclohexyl]-4-oxo-butyramide |

TABLE 1-continued

List of examples and diagrams of the amine used in the last synthesis step.

| Example | | Name of example compound |
|---|---|---|
| 20 | 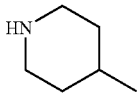 | N-[4-dimethylamino-4-(3-methyl-benzyl)-cyclohexyl]-4-(4-methyl-piperidin-1-yl)-4-oxo-butyramide |
| 21 | 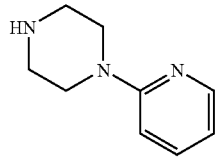 | N-[4-dimethylamino-4-(4-methyl-benzyl)-cyclohexyl]-4-oxo-4-(4-pyridin-2-yl-piperazin-1-yl)-butyramide |
| 22 | 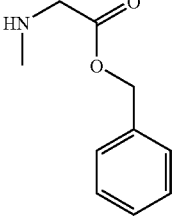 | ({3-[4-dimethylainino-4-(3-methyl-benzyl)-cyclohexylcarbamoyl]-propionyl}-methyl-amino)-acetic acid benzyl ester |
| 23 | 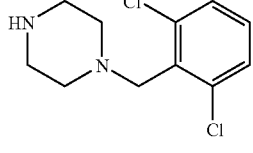 | 4-[4-(2,6-dichloro-benzyl)-piperazin-1-yl]-N-[4-dimethylamino-4-(3-methyl-benzyl)-cyclohexyl]-4-oxo-butyramide |
| 24 | 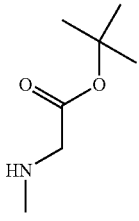 | {[4-(4-benzyl-4-dimethylamino-cyclohexylcarbamoyl)-butyryl]-methyl-amino}-acetic acid tert butyl ester |
| 25 | 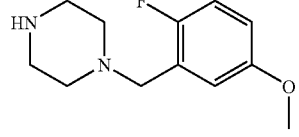 | 5-[4-(2-fluoro-5-methoxy-benzyl)-piperazin-1-yl]-5-oxo-valeric acid (4-benzyl-4-dimethylamino-cyclohexyl)-amide |
| 26 | 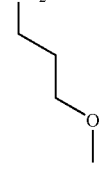 | N-[4-(4-chloro-benzyl)-4-dimethylamino-cyclohexyl]-N'-(3-methoxy-propyl)-succinamide |
| 27 | 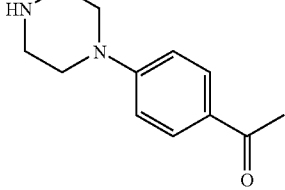 | 4-[4-(4-Acetyl-phenyl)-piperazin-1-yl]-N-[4-dimethylamino-4-(4-methyl-benzyl)-cyclohexyl]-4-oxo-butyramide |

TABLE 1-continued

List of examples and diagrams of the amine used in the last synthesis step.

| Example | Name of example compound |
|---|---|
| 28 | 4-{3-[4-dimethylamino-4-(4-methyl-benzyl)-cyclohexylcarbamoyl]-propionyl}-piperazin-1-carboxylic acid-tert-butylester |
| 29 | N-[4-(3-chloro-benzyl)-4-dimethylamino-cyclohexyl]-N'-(tetrahydro-furan-2-ylmethyl)-succinamide |
| 30 | 2-{3-[4-(3-chloro-benzyl)-4-dimethylamino-cyclohexylcarbamoyl]-propionylamino}-propanoic acid ethylester |
| 31 | N-(3-bromo-benzyl)-N'-[4-dimethylamino-4-(3-methyl-benzyl)-cyclohexyl]-succinamide |
| 32 | 3-(4-chloro-phenyl)-2-{3-[4-dimethylamino-4-(4-methyl-benzyl)-cyclohexylcarbamoyl]-propionylamino}-propanoic acid methylester |
| 33 | N-[4-(3-chloro-benzyl)-4-dimethylamino-cyclohexyl]-4-[4-(5-methyl-pyrazin-2-carbonyl)-piperazin-1-yl]-4-oxo-butyramide |
| 34 | N-[4-(4-chloro-benzyl)-4-dimethylamino-cyclohexyl]-N'-naphthalen-1-ylmethyl-succinamide |
| 35 | N-[4-dimethylamino-4-(3-methyl-benzyl)-cyclohexyl]-4-[4-(3-fluoro-4-methoxy-benzyl)-piperazin-1-yl]-4-oxo-butyramide |

TABLE 1-continued

List of examples and diagrams of the amine used in the last synthesis step.

| Example | | Name of example compound |
|---|---|---|
| 36 | 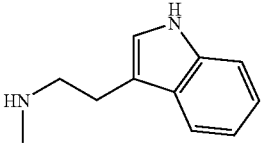 | N-[4-dimethylamino-4-(4-methyl-benzyl)-cyclohexyl]-N'-[2-(1H-indol-3-yl)-ethyl]-N'-methyl-succinamide |
| 37 | 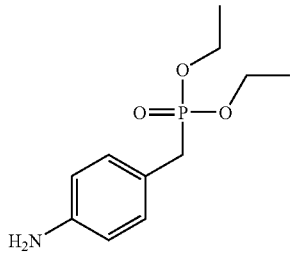 | (4-{3-[4-(3-chloro-benzyl)-4-dimethylamino-cyclohexylcarbamoyl]-propionylamino}-benzyl)-phosphonic acid diethylester |
| 38 | 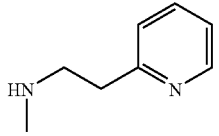 | N-[4-dimethylamino-4-(4-methyl-benzyl)-cyclohexyl]-N'-methyl-N'-(2-pyridin-2-yl-ethyl)-succinamide |
| 39 | 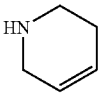 | N-[4-(3-chloro-benzyl)-4-dimethylamino-cyclohexyl]-4-(3,6-dihydro-2H-pyridin-1-yl)-4-oxo-butyramide |
| 40 | 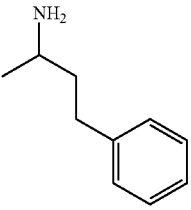 | N-[4-dimethylamino-4-(3-methyl-benzyl)-cyclohexyl]-N'-(1-methyl-3-phenyl-propyl)-succinamide |
| 41 | 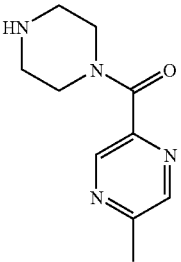 | 5-[4-(5-methyl-pyrazin-2-carbonyl)-piperazin-1-yl]-5-oxo-valeric acid (4-benzyl-4-dimethylamino-cyclohexyl)-amide |
| 42 | 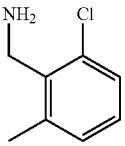 | N-[4-(3-chloro-benzyl)-4-dimethylamino-cyclohexyl]-N'-(2-chloro-6-methyl-benzyl)-succinamide |
| 43 | 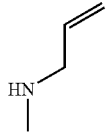 | N-allyl-N'-[4-(3-chloro-benzyl)-4-dimethylamino-cyclohexyl]-N-methyl-succinamide |

TABLE 1-continued

List of examples and diagrams of the amine used in the last synthesis step.

| Example | Name of example compound |
|---|---|
| 44 | N-[4-(4-chloro-benzyl)-4-dimethylamino-cyclohexyl]-Nt-cyclopentyl-succinamide |
| 45 | N-[4-dimethylamino-4-(4-methyl-benzyl)-cyclohexyl]-N'-(tetrahydro-furan-2-ylmethyl)-succinamide |
| 46 | (4-{3-[4-dimethylamino-4-(3-methyl-benzyl)-cyclohexylcarbamoyl]-propionylamino}-benzyl)-phosphonic acid diethylester |
| 47 | N-[4-(4-chloro-benzyl)-4-dimethylamino-cyclohexyl]-4-[4-(2-methoxy-phenyl)-piperazin-1-yl]-4-oxo-butyramide |
| 48 | N-[4-dimethylamino-4-(3-methyl-benzyl)-cyclohexyl]-4-[4-(3-methoxy-phenyl)-piperazin-1-yl]-4-oxo-butyramide |
| 49 | N-[4-(4-chloro-benzyl)-4-dimethylamino-cyclohexyl]-N'-(3,5-difluoro-benzyl)-succinamide |
| 50 | N-[4-(4-chloro-benzyl)-4-dimethylamino-cyclohexyl]-N'-(2-methyl-benzyl)-succinamide |

TABLE 1-continued

List of examples and diagrams of the amine used in the last synthesis step.

| Example | Name of example compound |
|---|---|
| 51 | N-[4-dimethylamino-4-(4-methyl-benzyl)-cyclohexyl]-4-oxo-4-{4-[(2,2,2-trifluoro-acetylamino)-methyl]-piperidin-1-yl}-butyramide |
| 52 | N-[4-(4-chloro-benzyl)-4-dimethylamino-cyclohexyl]-N'-[2-(1H-indol-3-yl)-ethyl]-succinamide |
| 53 | N-[4-(3-chloro-benzyl)-4-dimethylamino-cyclohexyl]-N'-[2-(1H-indol-3-yl)-ethyl]-N'-methyl-succinamide |
| 54 | 5-[4-(7-methoxy-benzo[1,3]dioxol-5-ylmethyl)-piperazin-1-yl]-5-oxo-valeric acid (4-benzyl-4-dimethylamino-cyclohex/1)-amide |
| 55 | N-benzyl-N'-[4-dimethylamino-4-(3-methyl-benzyl)-cyclohexyl]-N-(2-hydroxy-ethyl)-succinamide |
| 56 | 5-[4-(2,3-dimethyl-phenyl)-piperazin-1-yl]-5-oxo-valeric acid (4-benzyl-4-dimethylamino-cyclohexyl)-amide |
| 57 | N-[4-(4-chloro-benzyl)-4-dimethylamino-cyclohexyl]-N'-[2-(1H-indol-3-yl)-ethyl]-N'-methyl-succinamide |

TABLE 1-continued

List of examples and diagrams of the amine used in the last synthesis step.

| Example | Name of example compound |
|---|---|
| 58 | N-[4-dimethylamino-4-(4-methyl-benzyl)-cyclohexyl]-4-[4-(2,3-dimethyl-phenyl)-piperazin-1-yl]-4-oxo-butyramide |
| 59 | Glutaric acid-(4-benzyl-4-dimethylamino-cyclohexyl)-amide (1,2,3,4-tetrahydro-naphthalen-1-yl)-amide |
| 60 | N-[4-(4-chloro-benzyl)-4-dimethylamino-cyclohexyl]-4-(4-methyl-piperidin-1-yl)-4-oxobutyramide |
| 61 | 2-{3-[4-dimethylamino-4-(4-methyl-benzyl)-cyclohexylcarbamoyl]-propionylamino}-propanoic acid-tert-butylester |
| 62 | 5-(4-cycloheptyl-piperazin-1-yl)-5-oxo-valeric acid (4-benzyl-4-dimethylamino-cyclohexyl)-amide |
| 63 | Glutaric acid-(4-benzyl-4-dimethylamino-cyclohexyl)-amide[2-(4-fluoro-phenyl)-ethyl]-amide |
| 64 | Glutaric acid-(4-benzyl-4-dimethylamino-cyclohexyl)-amide[1-(2,6-dichloro-benzyl)-pyrrolidin-3-yl]-amide |
| 65 | N-[4-(4-chloro-benzyl)-4-dimethylamino-cyclohexyl]-4-(1,4-dioxa-8-aza-spiro[4.5]dec-8-yl)-4-oxo-butyramide |
| 66 | N-[4-(3-chloro-benzyl)-4-dimethylamino-cyclohexyl]-4-oxo-4-thiomorpholin-4-yl-butyramide |

TABLE 1-continued

List of examples and diagrams of the amine used in the last synthesis step.

| Example | Name of example compound |
|---|---|
| 67 | 4-(4-benzoyl-piperidin-1-yl)-N-[4-dimethylamino-4-(3-methyl-benzyl)-cyclohexyl]-4-oxo-butyramide |
| 68 | N-[4-(4-chloro-benzyl)-4-dimethylamino-cyclohexyl]-N'-(2,4-dimethoxy-benzyl)-succinamide |
| 69 | N-[4-dimethylamino-4-(3-methyl-benzyl)-cyclohexyl]-N'-(1,2,3,4-tetrahydro-naphthalen-1-yl)-succinamide |
| 70 | N-[4-(4-chloro-benzyl)-4-dimethylamino-cyclohexyl]-N'-ethyl-N'-pyridin-4-ylmethyl-succinamide |
| 71 | N-[2-(3,4-dimethoxy-phenyl)-ethyl]-N'-[4-dimethylamino-4-(3-methyl-benzyl)-cyclohexyl]-N-methyl-succinamide |
| 72 | N-[4-(4-chloro-benzyl)-4-dimethylamino-cyclohexyl]-N'-methyl-N'-pyridin-3-ylmethyl-succinamide |
| 73 | N-[4-(3-chloro-benzyl)-4-dimethylamino-cyclohexyl]-N'-pyridin-2-ylmethyl-succinamide |
| 74 | N-[4-(3-chloro-benzyl)-4-dimethylamino-cyclohexyl]-N'-(2-methyl-benzyl)-succinamide |
| 75 | N-[4-dimethylamino-4-(3-methyl-benzyl)-cyclohexyl]-N'-(4-methoxy-phenyl)-succinamide |
| 76 | N-[4-dimethylamino-4-(3-methyl-benzyl)-cyclohexyl]-N'-indan-2-yl-succinamide |

TABLE 1-continued

List of examples and diagrams of the amine used in the last synthesis step.

| Example | | Name of example compound |
|---|---|---|
| 77 | 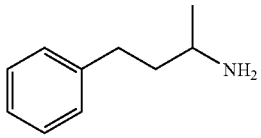 | N-[4-(3-chloro-benzyl)-4-dimethylamino-cyclohexyl]-N'-(1-methyl-3-phenyl-propyl)-succinamide |
| 78 | 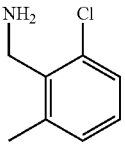 | N-(2-chloro-6-methyl-benzyl)-N'-[4-dimethylamino-4-(3-methyl-benzyl)-cyclohexyl]-succinamide |
| 79 | 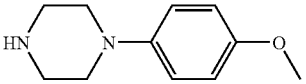 | N-[4-dimethylamino-4-(4-methyl-benzyl)-cyclohexyl]-4-[4-(4-methoxy-phenyl)-piperazin-1-yl]-4-oxo-butyramide |
| 80 | 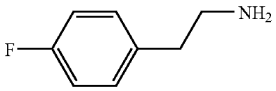 | N-[4-dimethylamino-4-(4-methyl-benzyl)-cyclohexyl]-N'-[2-(4-fluoro-phenyl)-ethyl]-succinamide |
| 81 | 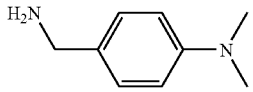 | Glutaric acid-(4-benzyl-4-dimethylamino-cyclohexyl)-amide 4-dimethylamino-benzylamide |
| 82 | 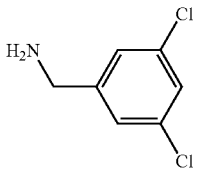 | N-[4-(3-chloro-benzyl)-4-dimethylamino-cyclohexyl]-N'-(3,5-dichloro-benzyl)-succinamide |
| 83 | 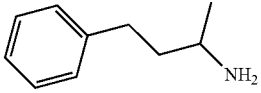 | N-[4-(4-chloro-benzyl)-4-dimethylamino-cyclohexyl]-N'-(1-methyl-3-phenyl-propyl)-succinamide |
| 84 | 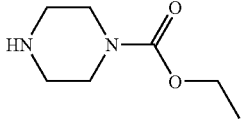 | 4-{3-[4-(3-chloro-benzyl)-4-dimethylamino-cyclohexylcarbamoyl]-propionyl}-piperazin-1-carboxylic acid ethylester |
| 85 | 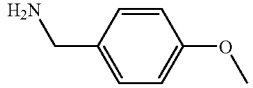 | N-[4-dimethylamino-4-(3-methyl-benzyl)-cyclohexyl]-N'-(4-methoxy-benzyl)-succinamide |
| 86 | 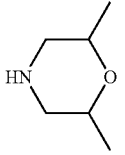 | N-[4-(4-chloro-benzyl)-4-dimethylamino-cyclohexyl]-4-(2,6-dimethyl-morpholin-4-yl)-4-oxo-butyramide |
| 87 | 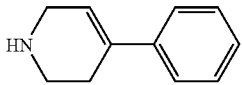 | N-[4-dimethylamino-4-(4-methyl-benzyl)-cyclohexyl]-4-oxo-4-(4-phenyl-3,6-dihydro-2H-pyridin-1-yl)-butyramide |

TABLE 1-continued

List of examples and diagrams of the amine used in the last synthesis step.

| Example | Name of example compound |
|---|---|
| 88 | N-[4-(4-chloro-benzyl)-4-dimethylamino-cyclohexyl]-N'-[2-(3-fluoro-phenyl)-ethyl]-succinamide |
| 89 | 4-[4-(4-allyloxy-benzyl)-piperazin-1-yl]-N-[4-dimethylamino-4-(3-methyl-benzyl)-cyclohexyl]-4-oxo-butyramide |
| 90 | Glutaric acid-(4-benzyl-4-dimethylamino-cyclohexyl)-amide[2-(5-bromo-2-methoxy-phenyl)-ethyl]-amide |
| 91 | 5-[4-(3-methoxy-phenyl)-piperazin-1-yl]-5-oxo-valeric acid (4-benzyl-4-dimethylamino-cyclohexyl)-amide |
| 92 | N-[4-(3-chloro-benzyl)-4-dimethylamino-cyclohexyl]-4-(4-methyl-piperidin-1-yl)-4-oxo-butyramide |
| 93 | (4-{3-[4-(4-chloro-benzyl)-4-dimethylamino-cyclohexylcarbamoyl]-propionylamino}-benzyl)-phosphonic acid diethylester |
| 94 | N-[4-dimethylamino-4-(4-methyl-benzyl)-cyclohexyl]-4-oxo-4-(4-o-tolyl-piperazin-1-yl)-butyramide |
| 95 | N-[4-dimethylamino-4-(3-methyl-benzyl)-cyclohexyl]-N'-[2-(3-fluoro-phenyl)-ethyl]-succinamide |
| 96 | 4-[4-(4-chloro-phenyl)-piperazin-1-yl]-N-[4-dimethylamino-4-(4-methyl-benzyl)-cyclohexyl]-4-oxo-butyramide |
| 97 | N-[4-(3-chloro-benzyl)-4-dimethylamino-cyclohexyl]-N'-[1-(4-fluoro-phenyl)-ethyl]-succinamide |

TABLE 1-continued

List of examples and diagrams of the amine used in the last synthesis step.

| Example | Name of example compound |
|---|---|
| 98 | N-[4-(4-chloro-benzyl)-4-dimethylamino-cyclohexyl]-N'-[1-(4-trifluoromethyl-benzyl)-pyrrolidin-3-yl]-succinamide |
| 99 | N-[4-(3-chloro-benzyl)-4-dimethylamino-cyclohexyl]-N'-[2-(1H-indol-3-yl)-ethyl]-succinamide |
| 100 | N-[4-(4-chloro-benzyl)-4-dimethylamino-cyclohexyl]-N'-indan-5-yl-succinamide |
| 101 | N-(4-benzyloxy-phenyl)-N'-[4-dimethylamino-4-(4-methyl-benzyl)-cyclohexyl]-succinamide |
| 102 | 2-{3-[4-dimethylamino-4-(3-methyl-benzyl)-cyclohexylcarbamoyl]-propionylamino}-3-methyl-valeric acid tert-butyl ester |
| 103 | 4-(4-benzyl-piperidin-1-yl)-N-[4-dimethylamino-4-(3-methyl-benzyl)-cyclohexyl]-4-oxo-butyramide |
| 104 | N-[4-(4-chloro-benzyl)-4-dimethylamino-cyclohexyl]-4-[4-(4-fluoro-phenyl)-3,6-dihydro-2H-pyridin-1-yl]-4-oxo-butyramide |
| 105 | N-[4-dimethylamino-4-(4-methyl-benzyl)-cyclohexyl]-N'-(1,2-dimethyl-propyl)-succinamide |
| 106 | N-[4-dimethylamino-4-(3-methyl-benzyl)-cyclohexyl]-4-(8-fluoro-1,3,4,5-tetrahydro-pyrido[4,3-b]indol-2-yl)-4-oxo-butyramide |
| 107 | 4-[4-(3-chloro-benzoyl)-piperazin-1-yl]-N-[4-dimethylamino-4-(3-methyl-benzyl)-cyclohexyl]-4-oxo-butyramide |
| 108 | N-[4-(4-chloro-benzyl)-4-dimethylamino-cyclohexyl]-N'-(4-methoxy-phenyl)-succinamide |

TABLE 1-continued

List of examples and diagrams of the amine used in the last synthesis step.

| Example | | Name of example compound |
|---|---|---|
| 110 | 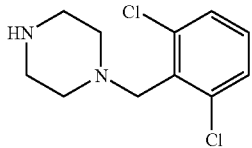 | 5-[4-(2,6-dichloro-benzyl)-piperazin-1-yl]-5-oxo-valeric acid (4-benzyl-4-dimethylamino-cyclohexyl)-amide |
| 111 | 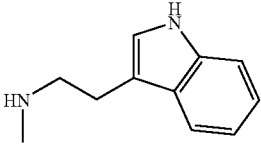 | N-[4-dimethylamino-4-(3-methyl-benzyl)-cyclohexyl]-N'-[2-(1H-indol-3-yl)-ethyl]-N'-methyl-succinamide |
| 112 | 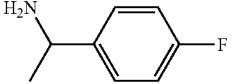 | N-[4-dimethylamino-4-(3-methyl-benzyl)-cyclohexyl]-N'-[1-(4-fluoro-phenyl)-ethyl]-succinamide |
| 113 | 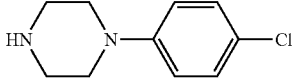 | 4-[4-(4-chloro-phenyl)-piperazin-1-yl]-N-[4-dimethylamino-4-(3-methyl-benzyl)-cyclohexyl]-4-oxo-butyramide |
| 114 | 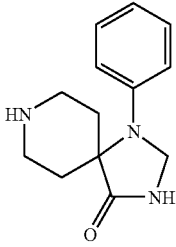 | N-[4-(3-chloro-benzyl)-4-dimethylamino-cyclohexyl]-4-oxo-4-(4-oxo-1-phenyl-1,3,8-triaza-spiro[4.5]dec-8-yl)-butyramide |
| 115 | 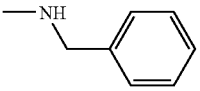 | N-benzyl-N'-[4-dimethylamino-4-(3-methyl-benzyl)-cyclohexyl]-N-methyl-succinamide |
| 116 | 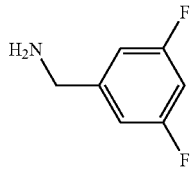 | N-[4-(3-chloro-benzyl)-4-dimethylamino-cyclohexyl]-N'-(3,5-difluoro-benzyl)-succinamide |
| 117 | 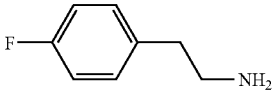 | N-[4-dimethylamino-4-(3-methyl-benzyl)-cyclohexyl]-N'-[2-(4-fluoro-phenyl)-ethyl]-succinamide |
| 118 | 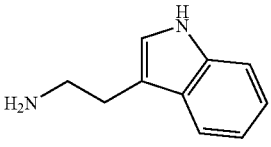 | N-[4-dimethylamino-4-(3-methyl-benzyl)-cyclohexyl]-N'-[2-(1H-indol-3-yl)-ethyl]-succinamide |
| 119 | 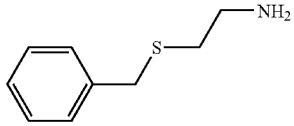 | N-(2-benzylsulphanyl-ethyl)-N'-[4-dimethylamino-4-(3-methyl-benzyl)-cyclohexyl]-succinamide |

TABLE 1-continued

List of examples and diagrams of the amine used in the last synthesis step.

| Example | | Name of example compound |
|---|---|---|
| 120 | 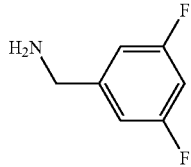 | N-[4-(3-chloro-benzyl)-4-dimethylamino-cyclohexyl]-N'-(2,4-difluoro-benzyl)-succinamide |
| 121 | 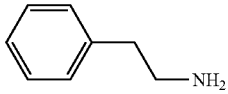 | N-[4-(3-chloro-benzyl)-4-dimethylamino-cyclohexyl]-N'-phenethyl-succinamide |
| 122 | 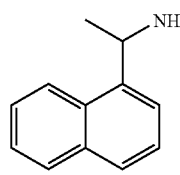 | N-[4-dimethylamino-4-(3-methyl-benzyl)-cyclohexyl]-N'-(1-naphthalen-2-yl-ethyl)-succinamide |
| 123 | 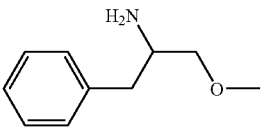 | N-[4-(3-chloro-benzyl)-4-dimethylamino-cyclohexyl]-N'-(1-methoxymethyl-2-phenyl-ethyl)-succinamide |
| 124 | 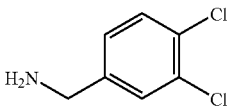 | N-[4-(3-chloro-benzyl)-4-dimethylamino-cyclohexyl]-N'-(3,4-dichloro-benzyl)-succinamide |
| 125 | 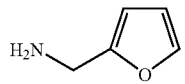 | N-[4-(3-chloro-benzyl)-4-dimethylamino-cyclohexyl]-N'-furan-2-ylmethyl-succinamide |
| 126 | 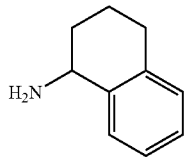 | N-[4-dimethylamino-4-(4-methyl-benzyl)-cyclohexyl]-N'-(1,2,3,4-tetrahydro-naphthalen-1-yl)-succinamide |
| 127 | 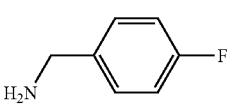 | N-[4-(3-chloro-benzyl)-4-dimethylamino-cyclohexyl]-N'-(4-fluoro-benzyl)-succinamide |
| 128 | 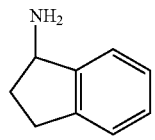 | N-[4-dimethylamino-4-(3-methyl-benzyl)-cyclohexyl]-N'-indan-1-yl-succinamide |
| 129 | 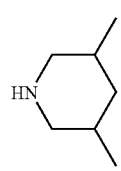 | N-[4-(3-chloro-benzyl)-4-dimethylamino-cyclohexyl]-4-(3,5-dimethyl-piperidin-1-yl)-4-oxo-butyramide |
| 130 | 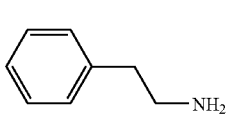 | N-[4-dimethylamino-4-(3-methyl-benzyl)-cyclohexyl]-N'-phenethyl-succinamide |

TABLE 1-continued

List of examples and diagrams of the amine used in the last synthesis step.

| Example | | Name of example compound |
|---|---|---|
| 131 | 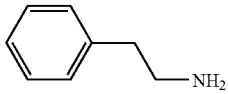 | N-[4-dimethylamino-4-(4-methyl-benzyl)-cyclohexyl]-N'-phenethyl-succinamide |
| 132 | 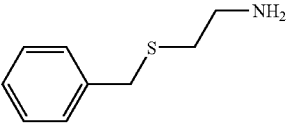 | N-(2-benzylsulphanyl-ethyl)-N'-[4-(3-chloro-benzyl)-4-dimethylamino-cyclohexyl]-succinamide |
| 133 | 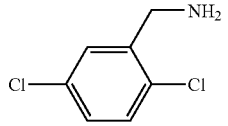 | N-[4-(3-chloro-benzyl)-4-dimethylamino-cyclohexyl]-N'-(2,5-dichloro-benzyl)-succinamide |
| 134 | 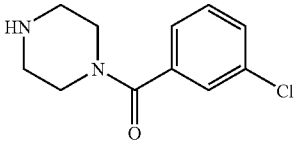 | 4-[4-(3-chloro-benzoyl)-piperazin-1-yl]-N-[4-(4-chloro-benzyl)-4-dimethylamino-cyclohexyl]-4-oxo-butyramide |
| 135 | 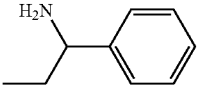 | N-[4-(4-chloro-benzyl)-4-dimethylamino-cyclohexyl]-N'-(1-phenyl-propyl)-succinamide |
| 136 | 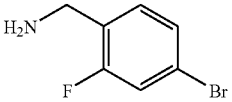 | N-(4-bromo-2-fluoro-benzyl)-N'-[4-dimethylamino-4-(3-methyl-benzyl)-cyclohexyl]-succinamide |
| 137 | 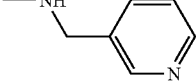 | N-[4-(3-chloro-benzyl)-4-dimethylamino-cyclohexyl]-N'-methyl-N'-pyridin-3-ylmethyl-succinamide |
| 138 | 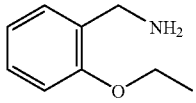 | N-[4-dimethylamino-4-(4-methyl-benzyl)-cyclohexyl]-N'-(2-ethoxy-benzyl)-succinamide |
| 139 | 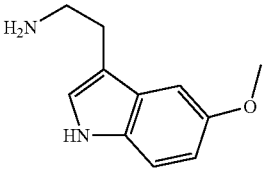 | N-[4-dimethylamino-4-(3-methyl-benzyl)-cyclohexyl]-N'-(2-(5-methoxy-1H-indol-3-yl)-ethyl]-succinamide |
| 140 | 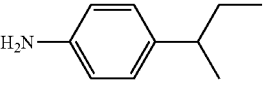 | N-(4-sec-butyl-phenyl)-N'-[4-(4-chloro-benzyl)-4-dimethylamino-cyclohexyl]-succinamide |
| 141 | 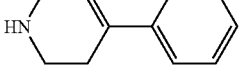 | 5-oxo-5-(4-phenyl-3,6-dihydro-2H-pyridin-1-yl)-valeric acid (4-benzyl-4-dimethylamino-cyclohexyl)-amide |
| 142 | 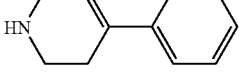 | 5-oxo-5-(4-phenyl-3,6-dihydro-2H-pyridin-1-yl)-valeric acid (4-benzyl-4-dimethylamino-cyclohexyl)-amide |

TABLE 1-continued

List of examples and diagrams of the amine used in the last synthesis step.

| Example | Name of example compound |
|---|---|
| 143 | N-[4-(3-chloro-benzyl)-4-dimethylamino-cyclohexyl]-N'-[2-(3-fluoro-phenyl)-ethyl]-succinamide |
| 144 | N-(3-bromo-benzyl)-N'-[4-(3-chloro-benzyl)-4-dimethylamino-cyclohexyl]-succinamide |
| 145 | N-(4-bromo-2-fluoro-benzyl)-N'-[4-(3-chloro-benzyl)-4-dimethylamino-cyclohexyl]-succinamide |
| 146 | N-[4-(3-chloro-benzyl)-4-dimethylamino-cyclohexyl]-N'-(1-phenyl-propyl)-succinamide |
| 147 | N-[4-dimethylamino-4-(3-methyl-benzyl)-cyclohexyl]-N'-(4-fluoro-2-trifluoromethyl-benzyl)-succinamide |
| 148 | N-[4-(3-chloro-benzyl)-4-dimethylamino-cyclohexyl]-N'-indan-2-yl-succinamide |
| 149 | N-[4-dimethylamino-4-(3-methyl-benzyl)-cyclohexyl]-4-oxo-4-(4-phenyl-3,6-dihydro-2H-pyridin-1-yl)-butyramide |
| 150 | N-[4-(4-chloro-benzyl)-4-dimethylamino-cyclohexyl]-N'-[2-(2-fluoro-phenyl)-ethyl]-succinamide |
| 151 | N-[4-dimethylamino-4-(4-methyl-benzyl)-cyclohexyl]-N'-[2-(2-fluoro-phenyl)-ethyl]-succinamide |
| 152 | Glutaric acid-(4-benzyl-4-dimethylamino-cyclohexyl)-amide[2-(2-fluoro-phenyl)-ethyl]-amide |
| 153 | N-[2-(2-chloro-phenyl)-ethyl]-N'-[4-dimethylamino-4-(4-methyl-benzyl)-cyclohexyl]-succinamide |

TABLE 1-continued

List of examples and diagrams of the amine used in the last synthesis step.

| Example | Name of example compound |
|---|---|
| 154 | N-[4-(3-chloro-benzyl)-4-dimethylamino-cyclohexyl]-N'-(3,4-difluoro-benzyl)-succinamide |
| 155 | N-benzyl-N-(2-cyano-ethyl)-N'-[4-dimethylamino-4-(4-methyl-benzyl)-cyclohexyl]-succinamide |
| 156 | N-[4-(3-chloro-benzyl)-4-dimethylamino-cyclohexyl]-N'-(3-methyl-benzyl)-succinamide |
| 157 | N-[4-(3-chloro-benzyl)-4-dimethylamino-cyclohexyl]-N'-(4-fluoro-3-trifluoromethyl-benzyl)-succinamide |
| 159 | N-[4-(3-chloro-benzyl)-4-dimethylamino-cyclohexyl]-N'-[2-(2-chloro-phenyl)-ethyl]-succinamide |
| 160 | N-[4-(3-chloro-benzyl)-4-dimethylamino-cyclohexyl]-N'-[2-(4-chloro-phenyl)-ethyl]-succinamide |
| 161 | N-[4-(3-chloro-benzyl)-4-dimethylamino-cyclohexyl]-N'-[2-(2,4-dichloro-phenyl)-ethyl]-succinamide |
| 162 | N-[4-(3-chloro-benzyl)-4-dimethylamino-cyclohexyl]-N'-indan-1-yl-succinamide |
| 163 | N-[4-(4-chloro-benzyl)-4-dimethylamino-cyclohexyl]-N'-indan-1-yl-succinamide |
| 164 | N-[2-(4-chloro-phenyl)-propyl]-N'-[4-dimethylamino-4-(3-methyl-benzyl)-cyclohexyl]-succinamide |
| 165 | N-(3-bromo-benzyl)-N'-[4-(4-chloro-benzyl)-4-dimethylamino-cyclohexyl]-succinamide |

TABLE 1-continued

List of examples and diagrams of the amine used in the last synthesis step.

| Example | | Name of example compound |
|---|---|---|
| 167 | 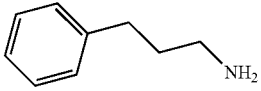 | N-[4-(3-chloro-benzyl)-4-dimethylamino-cyclohexyl]-N'-(3-phenyl-propyl)-succinamide |
| 168 | 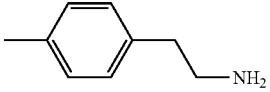 | N-[4-dimethylamino-4-(4-methyl-benzyl)-cyclohexyl]-N'-(2-p-tolyl-ethyl)-succinamide |
| 169 | 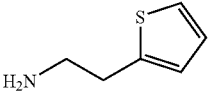 | N-[4-(3-chloro-benzyl)-4-dimethylamino-cyclohexyl]-N'-(2-thiophen-2-yl-ethyl)-succinamide |
| 170 | 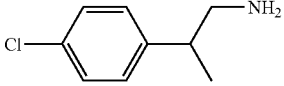 | Glutaric acid-(4-benzyl-4-dimethylamino-cyclohexyl)-amide[2-(4-chloro-phenyl)-propyl]-amide |
| 171 | 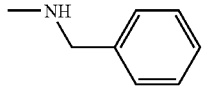 | N-benzyl-N'-[4-(3-chloro-benzyl)-4-dimethylamino-cyclohexyl]-N-methyl-succinamide |
| 172 | 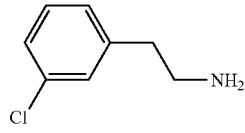 | N-[4-(3-chloro-benzyl)-4-dimethylamino-cyclohexyl]-N'-[2-(3-chloro-phenyl)-ethyl]-succinamide |
| 173 | 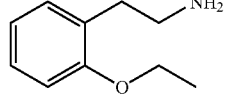 | Glutaric acid-(4-benzyl-4-dimethylamino-cyclohexyl)-amide[2-(2-ethoxy-phenyl)-ethyl]-amide |
| 174 | 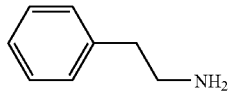 | Glutaric acid-(4-benzyl-4-dimethylamino-cyclohexyl)-amide phenethyl-amide |
| 175 | 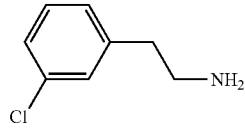 | Glutaric acid-(4-benzyl-4-dimethylamino-cyclohexyl)-amide[2-(3-chloro-phenyl)-ethyl]-amide |
| 176 | 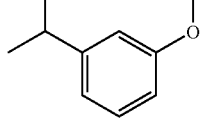 | N-[4-(3-chloro-benzyl)-4-dimethylamino-cyclohexyl]-N'-[1-(3-methoxy-phenyl)-ethyl]-succinamide |
| 177 | 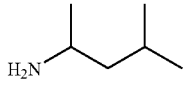 | Glutaric acid-(4-benzyl-4-dimethylamino-cyclohexyl)-amide (1,3-dimethyl-butyl)-amide |
| 178 | 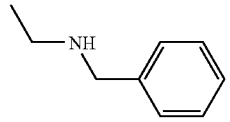 | N-benzyl-N'-[4-dimethylamino-4-(3-methyl-benzyl)-cyclohexyl]-N-ethyl-succinamide |

TABLE 1-continued

List of examples and diagrams of the amine used in the last synthesis step.

| Example | | Name of example compound |
|---|---|---|
| 179 | [structure: 4-chlorobenzylamine] | N-(4-chloro-benzyl)-N'-[4-(3-chloro-benzyl)-4-dimethylamino-cyclohexyl]-succinamide |
| 180 | [structure: 2-(2-fluorophenyl)ethylamine] | N-[4-(3-chloro-benzyl)-4-dimethylamino-cyclohexyl]-N'-[2-(2-fluoro-phenyl)-ethyl]-succinamide |
| 181 | [structure: 2-fluorobenzylamine] | N-[4-dimethylamino-4-(3-methyl-benzyl)-cyclohexyl]-N'-(2-fluoro-benzyl)-succinamide |
| 182 | [structure: 2-(4-chlorophenyl)ethylamine] | N-[2-(4-chloro-phenyl)-ethyl]-N'-[4-dimethylamino-4-(3-methyl-benzyl)-cyclohexyl]-succinamide |
| 183 | [structure: 2-(2-chlorophenyl)ethylamine] | N-[2-(2-chloro-phenyl)-ethyl]-N'-[4-dimethylamino-4-(3-methyl-benzyl)-cyclohexyl]-succinamide |
| 184 | [structure: 2-(3-chlorophenyl)ethylamine] | N-[2-(3-chloro-phenyl)-ethyl]-N'-[4-dimethylamino-4-(3-methyl-benzyl)-cyclohexyl]-succinamide |
| 185 | [structure: N-benzyl-3-aminopropionitrile] | N-benzyl-N'-[4-(3-chloro-benzyl)-4-dimethylamino-cyclohexyl]-N-(2-cyano-ethyl)-succinamide |
| 186 | [structure: 3-chloro-4-fluorobenzylamine] | N-[4-(3-chloro-benzyl)-4-dimethylamino-cyclohexyl]-N'-(3-chloro-4-fluoro-benzyl)-succinamide |
| 187 | [structure: 2-(trifluoromethyl)benzylamine] | N-[4-dimethylamino-4-(3-methyl-benzyl)-cyclohexyl]-N'-(2-trifluoromethyl-benzyl)-succinamide |
| 188 | [structure: 2-(2,4-dichlorophenyl)ethylamine] | N-[2-(2,4-dichloro-phenyl)-ethyl]-N'-[4-dimethylamino-4-(3-methyl-benzyl)-cyclohexyl]-succinamide |
| 189 | [structure: N-ethylbenzylamine] | N-benzyl-N'-[4-(3-chloro-benzyl)-4-dimethylamino-cyclohexyl]-N-ethyl-succinamide |

TABLE 1-continued

List of examples and diagrams of the amine used in the last synthesis step.

| Example | | Name of example compound |
|---|---|---|
| 190 | 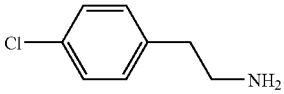 | N-[2-(4-chloro-phenyl)-ethyl]-N'-[4-dimethylamino-4-(4-methyl-benzyl)-cyclohexyl]-succinamide |
| 191 | 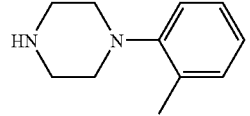 | 5-oxo-5-(4-o-tolyl-piperazin-1-yl)-valeric acid (4-benzyl-4-dimethylamino-cyclohexyl)-amide |
| 192 | 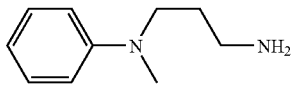 | N-[4-(3-chloro-benzyl)-4-dimethylamino-cyclohexyl]-N'-[3-(methyl-phenyl-amino)-propyl]-succinamide |
| 193 | 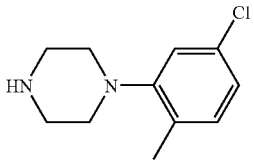 | N-[4-(3-chloro-benzyl)-4-dimethylamino-cyclohexyl]-4-[4-(5-chloro-2-methyl-phenyl)-piperazin-1-yl]-4-oxo-butyramide |
| 194 | 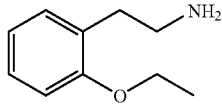 | N-[4-dimethylamino-4-(3-methyl-benzyl)-cyclohexyl]-N'-[2-(2-ethoxy-phenyl)-ethyl]-succinamide |
| 195 | 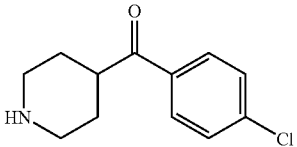 | 4-[4-(4-chloro-benzoyl)-piperidin-1-yl]-N-[4-(3-chloro-benzyl)-4-dimethylamino-cyclohexyl]-4-oxo-butyramide |
| 196 | 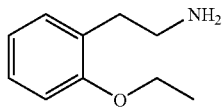 | N-[4-(3-chloro-benzyl)-4-dimethylamino-cyclohexyl]-N'-[2-(2-ethoxy-phenyl)-ethyl]-succinamide |
| 197 | 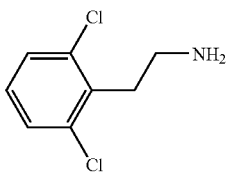 | N-[2-(2,6-dichloro-phenyl)-ethyl]-N'-[4-dimethylamino-4-(3-methyl-benzyl)-cyclohexyl]-succinamide |
| 198 | 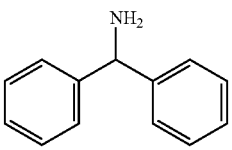 | N-benzhydryl-N'-[4-(3-chloro-benzyl)-4-dimethylamino-cyclohexyl]-succinamide |
| 199 | 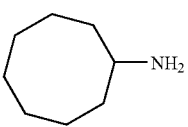 | N-[4-(3-chloro-benzyl)-4-dimethylamino-cyclohexyl]-N'-cyclooctyl-succinamide |

TABLE 1-continued

List of examples and diagrams of the amine used in the last synthesis step.

| Example | Name of example compound |
|---|---|
| 200 | N-[4-(3-chloro-benzyl)-4-dimethylamino-cyclohexyl]-N'-[2-(4-phenoxy-phenyl)-ethyl]-succinamide |
| 201 | N-[4-dimethylamino-4-(3-methyl-benzyl)-cyclohexyl]-N'-(2,3-dimethyl-benzyl)-succinamide |
| 202 | 4-[4-(5-chloro-2-methyl-phenyl)-piperazin-1-yl]-N-[4-dimethylamino-4-(3-methyl-benzyl)-cyclohexyl]-4-oxo-butyramide |
| 203 | 4-[4-(4-chloro-benzoyl)-piperidin-1-yl]-N-[4-dimethylamino-4-(3-methyl-benzyl)-cyclohexyl]-4-oxo-butyramide |
| 204 | N-[4-(3-chloro-benzyl)-4-dimethylamino-cyclohexyl]-N'-(1,2,3,4-tetrahydro-naphthalen-1-yl)-succinamide |
| 205 | N-(2-chloro-benzyl)-N'-[4-dimethylamino-4-(3-methyl-benzyl)-cyclohexyl]-succinamide |
| 206 | N-(2-chloro-benzyl)-N'-[4-(3-chloro-benzyl)-4-dimethylamino-cyclohexyl]-succinamide |
| 207 | N-[4-(3-chloro-benzyl)-4-dimethylamino-cyclohexyl]-N'-(3-fluoro-5-trifluoromethyl-benzyl)-succinamide |
| 208 | N-[4-(3-chloro-benzyl)-4-dimethylamino-cyclohexyl]-N'-(1-p-tolyl-ethyl)-succinamide |

TABLE 1-continued

List of examples and diagrams of the amine used in the last synthesis step.

| Example | Name of example compound |
|---|---|
| 209 | N-[2-(2,6-dichloro-benzylsulphanyl)-ethyl]-N'-[4-dimethylamino-4-(4-methyl-benzyl)-cyclohexyl]-succinamide |
| 210 | N-[4-(3-chloro-benzyl)-4-dimethylamino-cyclohexyl]-N'-[2-(2,6-dichloro-benzylsulphanyl)-ethyl]-succinamide |
| 211 | N-[4-(3-chloro-benzyl)-4-dimethylamino-cyclohexyl]-N'-[2-(3-trifluoromethyl-phenyl)-ethyl]-succinamide |
| 212 | N-[2-(3,4-dichloro-phenyl)-ethyl]-N'-[4-dimethylamino-4-(3-methyl-benzyl)-cyclohexyl]-succinamide |
| 213 | N-[4-(3-chloro-benzyl)-4-dimethylamino-cyclohexyl]-4-[4-(2-fluoro-phenyl)-piperazin-1-yl]-4-oxo-butyramide |
| 214 | 5-[4-(2,4-dimethoxy-phenyl)-piperazin-1-yl]-5-oxo-valeric acid (4-benzyl-4-dimethylamino-cyclohexyl)-amide |
| 215 | N-[4-(3-chloro-benzyl)-4-dimethylamino-cyclohexyl]-N'-(1-naplithalen-1-yl-ethyl)-succinamide |
| 216 | N-[4-dimethylamino-4-(3-methyl-benzyl)-cyclohexyl]-N'-(1-naplithalen-1-yl-ethyl)-succinamide |
| 217 | N-[4-(3-chloro-benzyl)-4-dimethylamino-cyclohexyl]-N'-(2-fluoro-benzyl)-N'-furan-2-ylmethyl-succinamide |

TABLE 1-continued

List of examples and diagrams of the amine used in the last synthesis step.

| Example | | Name of example compound |
|---|---|---|
| 218 | 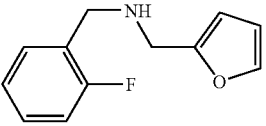 | N-[4-dimethylamino-4-(3-methyl-benzyl)-cyclohexyl]-N'-(2-fluoro-benzyl)-N'-furan-2-ylmethyl-succinamide |
| 219 | 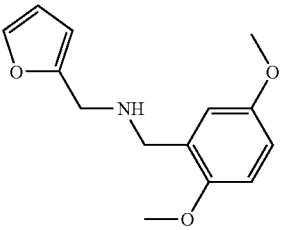 | N-[4-(3-chloro-benzyl)-4-dimethylamino-cyclohexyl]-N'-(2,5-dimethoxy-benzyl)-N'-furan-2-ylmethyl-succinamide |
| 220 | 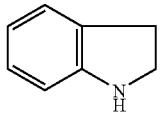 | N-(4-azepan-1-yl-4-benzyl-cyclohexyl)-4-(2,3-dihydro-indol-1-yl)-4-oxo-butyramide |
| 221 | 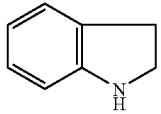 | 4-(2,3-dihydro-indol-1-yl)-N-[4-dimethylamino-4-(3-fluoro-phenyl)-cyclohexyl]-4-oxo-butyramide |
| 222 | 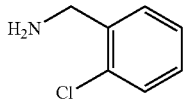 | N-(4-benzyl-4-morpholin-4-yl-cyclohexyl)-N'-(2-chloro-6-methyl-benzyl)-succinamide |
| 223 | 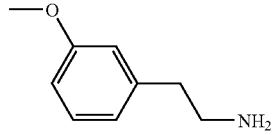 | N-(4-benzyl-4-morpholin-4-yl-cyclohexyl)-N'-[2-(3-methoxy-phenyl)-ethyl]-succinamide |
| 224 | 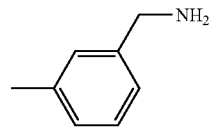 | N-(4-benzyl-4-morpholin-4-yl-cyclohexyl)-N'-(3-methyl-benzyl)-succinamide |
| 225 | 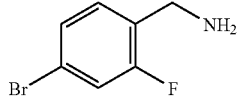 | N-(4-benzyl-4-morpholin-4-yl-cyclohexyl)-N'-(4-bromo-2-fluoro-benzyl)-succinamide |
| 226 | 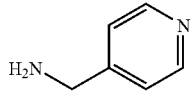 | N-(4-benzyl-4-morpholin-4-yl-cyclohexyl)-N'-pyridin-4-ylmethyl-succinamide |
| 227 | 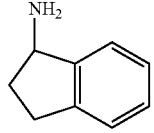 | N-(4-benzyl-4-morpholin-4-yl-cyclohexyl)-N'-indan-1-yl-succinamide |
| 228 | 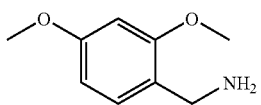 | N-(4-benzyl-4-morpholin-4-yl-cyclohexyl)-N'-(2,4-dimethoxy-benzyl)-succinamide |

TABLE 1-continued

List of examples and diagrams of the amine used in the last synthesis step.

| Example | | Name of example compound |
|---|---|---|
| 229 | | N-(4-benzyl-4-morpholin-4-yl-cyclohexyl)-N'-thiophen-2-ylmethyl-succinamide |
| 230 | | N-adamantan-1-ylmethyl-N'-(4-benzyl-4-morpholin-4-yl-cyclohexyl)-succinamide |
| 231 | | N-(4-benzyl-4-morpholin-4-yl-cyclohexyl)-N'-(2,5-difluoro-benzyl)-succinamide |
| 232 | | N-(4-benzyl-4-morpholin-4-yl-cyclohexyl)-N'-(4-tert-butyl-phenyl)-succinamide |
| 233 | | N-(4-benzyl-4-morpholin-4-yl-cyclohexyl)-N'-(3,5-bis-trifluoromethyl-benzyl)-succinamide |
| 234 | | N-(4-benzyl-4-morpholin-4-yl-cyclohexyl)-N'-[2-(2-ethoxy-phenyl)-ethyl]-succinamide |
| 235 | | N-(4-benzyl-4-morpholin-4-yl-cyclohexyl)-N'-(3-methoxy-propyl)-succinamide |
| 236 | | N-(4-benzyl-4-morpholin-4-yl-cyclohexyl)-N'-(2-morpholin-4-yl-ethyl)-succinamide |
| 237 | | N-(4-benzyl-4-morpholin-4-yl-cyclohexyl)-N'-(2,5-dichloro-benzyl)-succinamide |
| 238 | | N-(4-benzyl-4-morpholin-4-yl-cyclohexyl)-N'-[1-(2-benzyloxy-benzyl)-pyrrolidin-3-yl]-N'-methyl-succinamide |
| 239 | | N-(4-benzyl-4-morpholin-4-yl-cyclohexyl)-4-oxo-4-(2-pyrrolidin-1-ylmethyl-pyrrolidin-1-yl)-butyramide |

TABLE 1-continued

List of examples and diagrams of the amine used in the last synthesis step.

| Example | Name of example compound |
|---|---|
| 240 | N-(4-benzyl-4-morpholin-4-yl-cyclohexyl)-4-morpholin-4-yl-4-oxo-butyramide |
| 241 | N-(4-benzyl-4-morpholin-4-yl-cyclohexyl)-N'-(3-dimethylamino-propyl)-N'-methyl-succinamide |
| 242 | N-(4-benzyl-4-morpholin-4-yl-cyclohexyl)-N'-(2-phenyl-cyclopropyl)-succinamide |
| 243 | N-(4-benzyl-4-morpholn-4-yl-cyclohexyl)-N'-naphthalen-1-ylmethyl-succinamide |
| 244 | N-(4-benzyl-4-morpholin-4-yl-cyclohexyl)-4-(4-methyl-[1,4]diazepan-1-yl)-4-oxo-butyramide |
| 245 | N-(4-benzyl-4-morpholin-4-yl-cyclohexyl)-4-(4-hydroxy-piperidin-1-yl)-4-oxo-butyramide |
| 246 | N-(4-benzyl-4-morpholin-4-yl-cyclohexyl)-N'-[2-(7-methyl-1H-indol-3-yl)-ethyl]-succinamide |
| 247 | N-(4-benzyl-4-morpholin-4-yl-cyclohexyl)-N'-[2-(5-methoxy-1H-indol-3-yl)-ethyl]-succinamide |
| 248 | N-(4-benzyl-4-morpholin-4-yl-cyclohexyl)-4-oxo-4-(4-quinolin-2-ylmethyl-piperazin-1-yl)-butyramide |
| 249 | N-(4-dimethylamino-4-thiophen-2-yl-cyclohexyl)-4-oxo-4-[4-(5-trifluoromethyl-pyndrn-2-yl)-piperazin-1-yl]-butyramide |
| 250 | Glutaric acid-(1-adamantan-1-yl-ethyl)-amide (4-dimethylamino-4-thiophen-2-yl-cyclohexyl)-amide |

TABLE 1-continued

List of examples and diagrams of the amine used in the last synthesis step.

| Example | Name of example compound |
|---|---|
| 251 | N-[2-(2,6-dichloro-phenyl)-ethyl]-N'-(4-dimethylamino-4-thiophen-2-yl-cyclohexyl)-succinamide |
| 252 | N-(4-dimethylamino-4-thiophen-2-yl-cyclohexyl)-N'-(1-methyl-3-phenyl-propyl)-succinamide |
| 253 | N-benzyl-N'-(4-dimethylamino-4-thiophen-2-yl-cyclohexyl)-N-ethyl-succinamide |
| 254 | N-[2-(4-bromo-phenyl)-ethyl]-N'-(4-dimethylamino-4-thiophen-2-yl-cyclohexyl)-succinamide |
| 255 | 4-[4-(4-chloro-benzoyl)-piperidin-1-yl]-N-(4-dimethylamino-4-thiophen-2-yl-cyclohexyl)-4-oxo-butyramide |
| 256 | Glutaric acid-[1-(2,6-dichloro-benzyl)-pyrrolidin-3-yl]-amide (4-dimethylamino-4-thiophen-2-yl-cyclohexyl)-amide |
| 257 | Glutaric acid-(4-dimethylamino-4-thiophen-2-yl-cyclohexyl)-amide (3-phenyl-propyl)-amide |
| 258 | N-(4-dimethylamino-4-phenyl-cyclohexyl)-N'-pentyl-succinamide |
| 259 | 3-(4-chloro-phenyl)-2-[4-(4-dimethylamino-4-thiophen-2-yl-cyclohexylcarbamoyl)-butyrylamino]-propanoic acid ethylester |
| 260 | Glutaric acid-(4-dimethylamino-4-thiophen-2-yl-cyclohexyl)-amide indan-1-ylamide |
| 261 | N-adamantan-1-ylmethyl-N'-(4-dimethylamino-4-thiophen-2-yl-cyclohexyl)-succinamide |

TABLE 1-continued

List of examples and diagrams of the amine used in the last synthesis step.

| Example | Name of example compound |
|---|---|
| 262 | 5-(4-benzofuran-2-ylmethyl-piperazin-1-yl)-5-oxo-valeric acid (4-dimethylamino-4-thiophen-2-yl-cyclohexyl)-amide |
| 263 | 4-[4-(4-tert-butyl-benzyl)-piperazin-1-yl]-N-(4-dimethylamino-4-phenyl-cyclohexyl)-4-oxo-butyramide |
| 264 | Glutaric acid-(4-dimethylamino-4-thiophen-2-yl-cyclohexyl)-amide[2-(1H-indol-3-yl)-ethyl]-amide |
| 265 | N-(4-dimethylamino-4-phenyl-cyclohexyl)-4-[4-hydroxy-4-(3-trifluoromethyl-phenyl)-piperidin-1-yl]-4-oxo-butyramide |
| 266 | 5-(3,4-dihydro-1H-isoquinolin-2-yl)-5-oxo-valeric acid (4-dimethylamino-4-thiophen-2-yl-cyclohexyl)-amide |
| 267 | 4-(4-benzyl-piperidin-1-yl)-N-(4-dimethylamino-4-phenyl-cyclohexyl)-4-oxo-butyramide |
| 268 | {[4-(4-dimethylamino-4-thiophen-2-yl-cyclohexylcarbamoyl)-butyryl]-methyl-amino}-acetic acid benzylester |
| 269 | N-benzyl-N'-(4-dimethylamino-4-phenyl-cyclohexyl)-N-phenethyl-succinamide |
| 270 | Glutaric acid-(4-dimethylamino-4-thiophen-2-yl-cyclohexyl)-amide 3-trifluoromethoxy-benzylamide |
| 271 | Glutaric acid-(4-dimethylamino-4-thiophen-2-yl-cyclohexyl)-amide ethyl-(2-methyl-allyl)-amide |
| 272 | N,N-bis-(2-cyano-ethyl)-N'-(4-dimethylamino-4-thiophen-2-yl-cyclohexyl)-succinamide |

TABLE 1-continued

List of examples and diagrams of the amine used in the last synthesis step.

| Example | | Name of example compound |
|---|---|---|
| 273 | 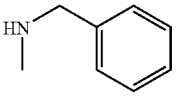 | Glutaric acid-benzyl-methyl-amide (4-dimethylamino-4-thiophen-2-yl-cyclohexyl)-amide |
| 274 | 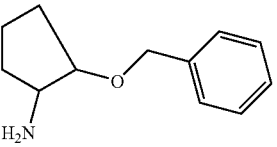 | Glutaric acid-(2-benzyloxy-cyclopentyl)-amide (4-dimethylamino-4-thiophen-2-yl-cyclohexyl)-amide |
| 275 |  | Glutaric acid-(4-dimethylamino-4-thiophen-2-yl-cyclohexyl)-amide 4-trifluoromethyl-benzylamide |
| 276 | 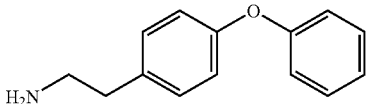 | N-(4-dimethylamino-4-thiophen-2-yl-cyclohexyl)-N'-[2-(4-phenoxy-phenyl)-ethyl]-succinamide |
| 277 | 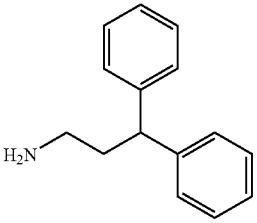 | Glutaric acid-(4-dimethylamino-4-thiophen-2-yl-cyclohexyl)-amide (3,3-diphenyl-propyl)-amide |
| 278 | 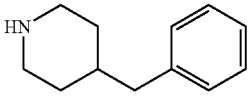 | 4-(4-benzyl-piperidin-1-yl)-N-(4-dimethylamino-4-thiophen-2-yl-cyclohexyl)-4-oxo-butyramide |
| 279 | 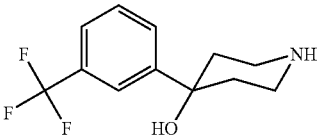 | N-(4-dimethylamino-4-thiophen-2-yl-cyclohexyl)-4-[4-hydroxy-4-(3-trifluoromethyl-phenyl)-piperidin-1-yl]-4-oxo-butyramide |
| 280 | 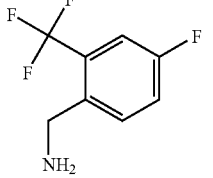 | Glutaric acid-(4-dimethylamino-4-thiophen-2-yl-cyclohexyl)-amide 4-fluoro-2-trifluoromethyl-benzylamide |
| 281 | 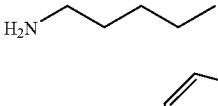 | N-(4-dimethylamino-4-thiophen-2-yl-cyclohexyl)-N'-pentyl-succinamide |
| 282 | 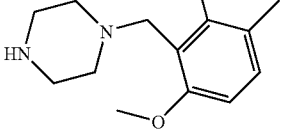 | 5-[4-(2-methoxy-naphthalen-1-ylmethyl)-piperazin-1-yl]-5-oxo-valeric acid (4-dimethylamino-4-thiophen-2-yl-cyclohexyl)-amide |

TABLE 1-continued

List of examples and diagrams of the amine used in the last synthesis step.

| Example | Name of example compound |
|---------|--------------------------|
| 283 | N-(4-dimethylamino-4-thiophen-2-yl-cyclohexyl)-N'-(2-ethoxy-benzyl)-N'-furan-2-ylmethyl-succinamide |
| 284 | Glutaric acid-(4-dimethylamino-4-thiophen-2-yl-cyclohexyl)-amide (2-phenyl-cyclopropyl)-amide |
| 285 | N-[2-(3,4-dichloro-phenyl)-ethyl]-N'-(4-dimethylamino-4-phenyl-cyclohexyl)-succinamide |
| 286 | N-adamantan-1-ylmethyl-N'-(4-dimethylamino-4-phenyl-cyclohexyl)-succinamide |
| 287 | 5-[4-(4-fluoro-phenyl)-3,6-dihydro-2H-pyridin-1-yl]-5-oxo-valeric acid (4-dimethylamino-4-thiophen-2-yl-cyclohexyl)-amide |
| 288 | 2-[4-(4-dimethylamino-4-thiophen-2-yl-cyclohexylcarbamoyl)-butyrylamino]-4-methyl-valeric acid benzyl ester |
| 289 | {4-[4-(4-dimethylamino-4-thiophen-2-yl-cyclohexylcarbamoyl)-butyrylamino]-phenyl}-carbamic acid-tert-butylester |
| 290 | Glutaric acid-(4-dimethylamino-4-thiophen-2-yl-cyclohexyl)-amide[2-(3-methoxy-phenyl)-ethyl]-amide |
| 291 | Glutaric acid-benzyl-ethyl-amide (4-dimethylamino-4-thiophen-2-yl-cyclohexyl)-amide |
| 292 | Glutaric acid-3-chloro-benzylamide (4-dimethylamino-4-thiophen-2-yl-cyclohexyl)-amide |
| 293 | Glutaric acid-(4-dimethylamino-4-thiophen-2-yl-cyclohexyl)-amide (4-methyl-cyclohexyl)-amide |

TABLE 1-continued

List of examples and diagrams of the amine used in the last synthesis step.

| Example | | Name of example compound |
|---|---|---|
| 294 | 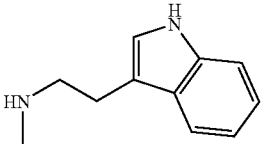 | N-(4-dimethylamino-4-phenyl-cyclohexyl)-N'-[2-(1H-indol-3-yl)-ethyl]-N'-methyl-succinamide |
| 295 | 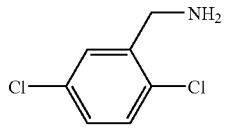 | Glutaric acid-2,5-dichloro-benzylamide (4-dimethylamino-4-thiophen-2-yl-cyclohexyl)-amide |
| 296 | 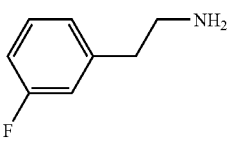 | Glutaric acid-(4-dimethylamino-4-thiophen-2-yl-cyclohexyl)-amide[2-(3-fluoro-phenyl)-ethyl]-amide |
| 297 | 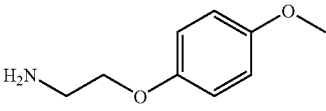 | N-(4-dimethylamino-4-phenyl-cyclohexyl)-N'-[2-(4-methoxy-phenoxy)-ethyl]-succinamide |
| 298 | 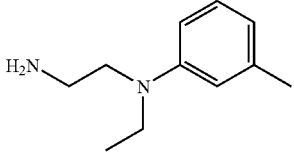 | N-(4-dimethylamino-4-thiophen-2-yl-cyclohexyl)-N'-[2-(ethyl-m-tolyl-amino)-ethyl]-succinamide |
| 299 | 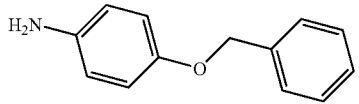 | Glutaric acid-(4-benzyloxy-phenyl)-amide (4-dimethylamino-4-thiophen-2-yl-cyclohexyl)-amide |
| 300 | 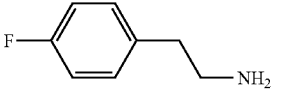 | Glutaric acid-(4-dimethylamino-4-thiophen-2-yl-cyclohexyl)-amide[2-(4-fluoro-phenyl)-ethyl]-amide |
| 301 | 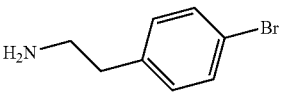 | Glutaric acid-[2-(4-bromo-phenyl)-ethyl]-amide (4-dimethylamino-4-thiophen-2-yl-cyclohexyl)-amide |
| 302 | 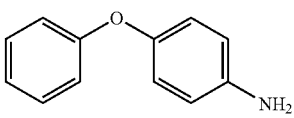 | N-(4-dimethylamino-4-thiophen-2-yl-cyclohexyl)-N'-(4-phenoxy-phenyl)-succinamide |
| 303 | 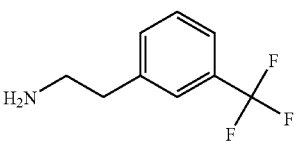 | N-(4-dimethylamino-4-phenyl-cyclohexyl)-N'-[2-(3-trifluoromethyl-phenyl)-ethyl]-succinamide |
| 304 | 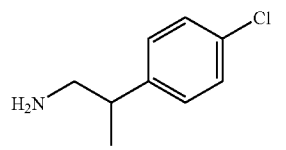 | Glutaric acid-[2-(4-chloro-phenyl)-propyl]-amide (4-dimethylamino-4-thiophen-2-yl-cyclohexyl)-amide |

TABLE 1-continued

List of examples and diagrams of the amine used in the last synthesis step.

| Example | Name of example compound |
|---|---|
| 305 | N-(4-dimethylamino-4-thiophen-2-yl-cyclohexyl)-N'-[2-(1H-indol-3-yl)-ethyl]-N'-methyl-succinamide |
| 306 | N-(4-dimethylamino-4-thiophen-2-yl-cyclohexyl)-N'-[2-(4-methoxy-phenoxy)-ethyl]-succinamide |
| 307 | Glutaric acid-(4-dimethylamino-4-thiophen-2-yl-cyclohexyl)-amide (3-phenoxy-phenyl)-amide |
| 308 | N-(4-dimethylamino-4-phenyl-cyclohexyl)-N'-[2-(ethyl-m-tolyl-amino)-ethyl]-succinamide |
| 309 | Glutaric acid-[2-(5-bromo-2-methoxy-phenyl)-ethyl]-amide (4-dimethylamino-4-thiophen-2-yl-cyclohexyl)-amide |
| 310 | N-(4-dimethylamino-4-thiophen-2-yl-cyclohexyl)-N'-[2-(3-trifluoromethyl-phenyl)-ethyl]-succinamide |
| 311 | Glutaric acid-(4-dimethylamino-4-thiophen-2-yl-cyclohexyl)-amide (1-methyl-3-phenyl-propyl)-amide |
| 312 | N-[2-(2,6-dichloro-benzylsulphanyl)-ethyl]-N'-(4-dimethylamino-4-thiophen-2-yl-cyclohexyl)-succinamide |
| 313 | Glutaric acid-(4-dimethylamino-4-thiophen-2-yl-cyclohexyl)-amide (2,2-diphenyl-propyl)-amide |
| 314 | N-(4-dimethylamino-4-thiophen-2-yl-cyclohexyl)-N'-[3-(methyl-phenyl-amino)-propyl]-succinamide |

TABLE 1-continued

List of examples and diagrams of the amine used in the last synthesis step.

| Example | | Name of example compound |
|---|---|---|
| 315 | 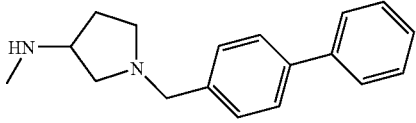 | N-(1-biphenyl-4-ylmethyl-pyrrolidin-3-yl)-N'-(4-dimethylamino-4-thiophen-2-yl-cyclohexyl)-N-methyl-succinamide |
| 316 | 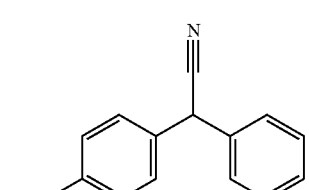 | Glutaric acid-[4-(cyano-phenyl-methyl)-phenyl]-amide (4-dimethylamino-4-thiophen-2-ylcyclohexyl)-amide |
| 317 |  | Glutaric acid-(4-tert-butyl-cyclohexyl)-amide (4-dimethylamino-4-thiophen-2-yl-cyclohexyl)-amide |
| 318 | 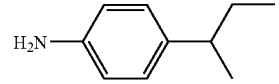 | Glutaric acid-(4-sec-butyl-phenyl)-amide (4-dimethylamino-4-thiophen-2-yl-cyclohexyl)-amide |
| 319 | 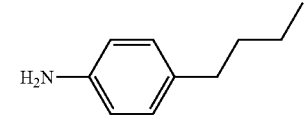 | Glutaric acid-(4-butyl-phenyl)-amide (4-dimethylamino-4-thiophen-2-yl-cyclohexyl)-amide |
| 320 | 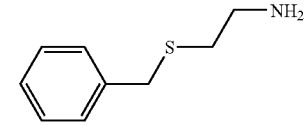 | N-(2-benzylsulphanyl-ethyl)-N'-(4-dimethylamino-4-thiophen-2-yl-cyclohexyl)-succinamide |
| 321 | 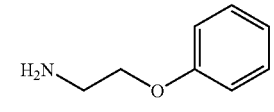 | N-(4-dimethylamino-4-thiophen-2-yl-cyclohexyl)-N'-(2-phenoxy-ethyl)-succinamide |
| 322 | 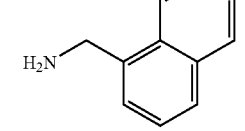 | Glutaric acid-(4-dimethylamino-4-thiophen-2-yl-cyclohexyl)-amide (naphthalen-1-ylmethyl)-amide |
| 323 | 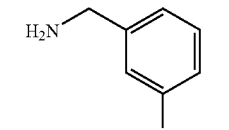 | Glutaric acid-3-bromo-benzylamide (4-dimethylamino-4-thiophen-2-yl-cyclohexyl)-amide |
| 324 | 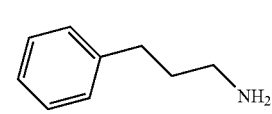 | N-(4-dimethylamino-4-thiophen-2-yl-cyclohexyl)-N'-(3-phenyl-propyl)-succinamide |
| 325 | 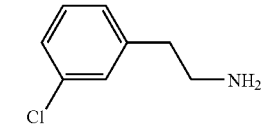 | N-[2-(3-chloro-phenyl)-ethyl]-N'-(4-dimethylamino-4-phenyl-cyclohexyl)-succinamide |

TABLE 1-continued

List of examples and diagrams of the amine used in the last synthesis step.

| Example | | Name of example compound |
|---|---|---|
| 326 | 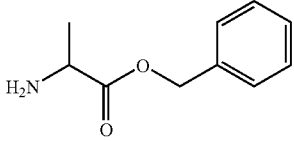 | 2-[3-(4-dimethylamino-4-thiophen-2-yl-cyclohexylcarbamoyl)-propionylamino]-propanoic acid benzylester |
| 327 | 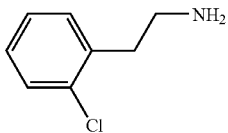 | N-[2-(2-chloro-phenyl)-ethyl]-N'-(4-dimethylamino-4-phenyl-cyclohexyl)-succinamide |
| 328 | 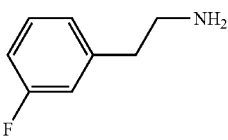 | N-(4-dimethylamino-4-phenyl-cyclohexyl)-N'-[2-(3-fluoro-phenyl)-ethyl]-succinamide |
| 329 | 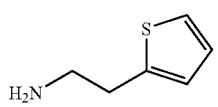 | Glutaric acid-(4-dimethylamino-4-thiophen-2-yl-cyclohexyl)-amide (2-thiophen-2-yl-ethyl)-amide |
| 330 | 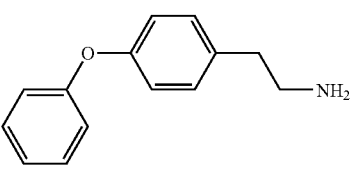 | Glutaric acid-(4-dimethylamino-4-thiophen-2-yl-cyclohexyl)-amide[2-(4-phenoxy-phenyl)-ethyl]-amide |
| 331 | 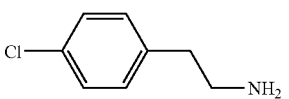 | N-[2-(4-chloro-phenyl)-ethyl]-N'-(4-dimethylamino-4-phenyl-cyclohexyl)-succinamide |
| 332 | 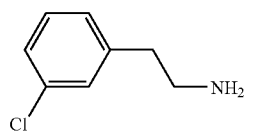 | N-[2-(3-chloro-phenyl)-ethyl]-N'-(4-dimethylamino-4-thiophen-2-yl-cyclohexyl)-succinamide |
| 333 | 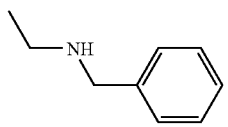 | N-benzyl-N'-(4-dimethylamino-4-thiophen-2-yl-cyclohexyl)-N-ethyl-succinamide |
| 334 | 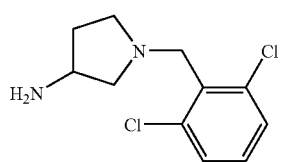 | Glutaric acid-[1-(2,6-dichloro-benzyl)-pyrrolidin-3-yl]-amide (4-dimethylamino-4-thiophen-2-yl-cyclohexyl)-amide |
| 335 | 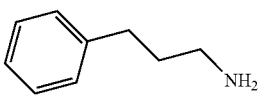 | Glutaric acid-(4-dimethylamino-4-thiophen-2-yl-cyclohexyl)-amide (3-phenyl-propyl)-amide |

TABLE 1-continued

List of examples and diagrams of the amine used in the last synthesis step.

| Example | | Name of example compound |
|---|---|---|
| 336 | 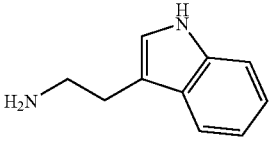 | Glutaric acid-(4-dimethylamino-4-thiophen-2-yl-cyclohexyl)-amide[2-(1H-indol-3-yl)-ethyl]-amide |
| 337 | 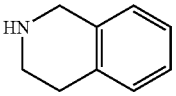 | 5-(3,4-dihydro-1H-isoquinolin-2-yl)-5-oxo-valeric acid (4-dimethylamino-4-thiophen-2-yl-cyclohexyl)-amide |
| 338 | 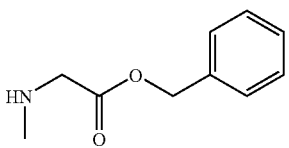 | {[4-(4-dimethylamino-4-thiophen-2-yl-cyclohexylcarbamoyl)-butyryl]-methyl-amino}-acetic acid benzylester |
| 339 | 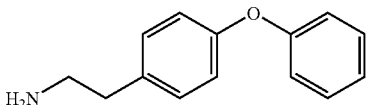 | N-(4-dimethylamino-4-thiophen-2-yl-cyclohexyl)-N'-[2-(4-phenoxy-phenyl)-ethyl]-succinamide |
| 340 | 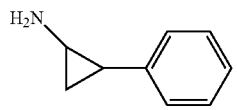 | Glutaric acid-(4-dimethylamino-4-thiophen-2-yl-cyclohexyl)-amide (2-phenyl-cyclopropyl)-amide |

Selected examples have also been synthesised on a larger scale.

Example 341

N-[-(4-chlorobenzyl)-4-dimethylaminocyclohexyl]-N'-furan-2-yl-methylsuccinic acid amide hydrochloride, non-polar diastereoisomer A solution of 5.0 ml C-furan-2-yl-methylamine and 6.7 ml dilsopropylethylamine in 25 ml THF p.a. was added dropwise to 3.92 g succinic acid anhydride in 40 ml THF p.a. and the solution stirred over night. After addition of 25 ml two-molar hydrochloric acid, extraction was carried out three times with 40 ml dichloromethane in each case, the extracts dried over magnesium sulphate, filtered and evaporated. 7.0 g N-furan-2-yl-methylsuccinic acid were obtained.

1.0 g 1-(3-chlorobenzyl)-N,N-dimethylcyclohexane-1,4-diamine, obtained as a cis/trans-mixture from 4-(3-chlorobenzyl)-4-dimethylaminocyclohexanone by reaction with hydroxylamine and reduction of the oxime obtained with lithium aluminium hydride (WO 02090317), dissolved in 5 ml DMF, was added to 0.74 g N-furan-2-yl-methylsuccinic acid at 0° C. and 0.59 ml N,N-diisopropylcarbodiimide followed by 0.5 g 1-hydroxybenzotriazole (HOBt) were added while stirring. After 3 hours in an ice bath, the mixture was stirred overnight at room temperature. For working up, one-molar sodium carbonate solution was added (pH>10) and the crude product (1.75 g) was isolated by extraction with ethyl acetate/THF (V:V=1:1), with subsequent drying over sodium sulphate and evaporation. The main fraction, obtained after column chromatography on silica gel (3.0×20 cm) with 250 ml diethyl ether, diethyl ether/methanol (V:V=4:1) and diethyl ether/methanol (V:V=1:1), of 718 mg was dissolved in 50 ml 2-butanone, 50 ml ethyl acetate and 2 ml methanol and, by adding 29 µl water and 200 µl chlorotrimethylsilane, converted into the corresponding hydrochloride of the N-[4-(3-chlorobenzyl)-4-dimethylaminocyclohexyl]-N'-furan-2-yl-methylsuccinic acid amide (648 mg of white solid, mp. 233-234.5° C.).

Example 342

N-[4-(3-chlorobenzyl)-4-dimethylaminocyclohexyl]-N'-furan-2-yl-methylsuccinic acid amide hydrochloride, polar diastereoisomer As described for Example 341, 357 mg of the polar diastereoisomer of N-[4-(3-chlorobenzyl)-4-dimethylaminocyclohexyl]-N'-furan-2-yl-methylsuccinic acid amide were also obtained, which, dissolved in 25 ml 2-butanone, were converted into the corresponding hydrochloride by adding 14.4 µl water and 100 µl chlorotrimethylsilane (230 mg of white solid, mp. 186-188° C.).

Example 343

Glutaric acid (4-benzyl-4-dimethylaminocyclohexyl)amide [2-(2-fluorophenyl)ethyl]amide hydrochloride, non-polar diastereoisomer As described for Example 341, 0.95 mg 4-[2-(2-fluorophenyl)ethylcarbamoyl]butyric acid and 0.87 1-benzyl-N,N-dimethylcyclohexane-1,4-diamine were converted in 5 ml DMF in the presence of 0.59 ml N,N-diisopropylcarbodiimide and 0.50 g 1-hydroxybenzotriazole and the crude product (1.65 g yellow solid) similarly isolated. 720 mg of the non-polar diastereoisomer of glutaric acid (4-benzyl-4-dimethylaminocyclohexyl)amide was obtained by column chromatography on silica gel (3.0×20 cm) with 450 ml diethyl ether, followed by 450 ml diethyl ether/methanol (V:V=4:1) and 450 ml diethyl ether/methanol (V:V=1:1), was dissolved in 25 ml 2-butanone, 25 ml ethyl acetate and converted into the corresponding hydrochloride by adding 28 µl water and 198 µl chlorotrimethylsilane (657 mg of vitreous solid).

Example 344

Glutaric acid (4-benzyl-4-dimethylaminocyclohexyl)amide [2-(2-fluorophenyl)ethyl]amide hydrochloride, polar diastereoisomer As described for Example 343, 260 mg of the polar diastereoisomer of glutaric acid (4-benzyl-4-dimethylaminocyclohexyl)amide were also obtained, which were dissolved in 5 ml 2-butanone and 45 ml ethyl acetate and converted into the corresponding hydrochloride by adding 10 µl water and 71 µl chlorotrimethylsilane (110 mg of vitreous solid).

Example 345

N-[4-(3-chlorobenzyl)-4-dimethylaminocyclohexyl]-N'-[2-(4-chlorophenyl)ethyl]succinic acid amide hydrochloride, non-polar diastereoisomer As described for Example 341, 0.96 mg N-[2-(4-chlorophenyl)ethyl]succinic acid and 1.0 g 4-(3-chlorobenzyl)-4-dimethylaminocyclohexanone were converted in 5 ml DMF in the presence of 0.59 ml N,N-diisopropylcarbodiimide and 0.5 g 1-hydroxybenzotriazole and the crude product (2.23 g yellow solid) similarly isolated. 947 mg of the non-polar diastereoisomer of N-[4-(3-chlorobenzyl)-4-dimethylaminocyclohexyl]-N'-[2-(4-chlorophenyl)ethyl]succinic acid amide were obtained by column chromatography on silica gel (3.0×20 cm) with 200 ml diethyl ether, followed by 200 ml diethyl ether/methanol (V:V=5:1). 300 mg of this were dissolved in 5 ml 2-butanone, 10 ml ethyl acetate and 1 ml methanol and 10.7 µl water and 76 µl chlorotrimethylsilane were added, the batch evaporated to dryness, the residue stirred over 3 days at room temperature with 10 ml butanone and 10 diisopropylether and the precipitated hydrochloride isolated by filtration and dried (200 mg white solid).

Example 346

N-[4-(3-chlorobenzyl)-4-dimethylaminocyclohexyl]-N'-[2-(4-chlorophenyl)ethyl]succinic acid amide hydrochloride, polar diastereoisomer As described for Example 345, 360 mg of the polar diastereoisomer of N-[4-(3-chlorobenzyl)-4-dimethylaminocyclohexyl]-N'-[2-(4-chlorophenyl)ethyl]succinic acid amide were also obtained, which were dissolved in 25 ml 2-butanone and 10 ml ethyl acetate and converted into the corresponding hydrochloride by adding 12.5 µl water, 88 µl chlorotrimethylsilane and 10 ml diisopropylether (236 mg of white solid, mp 186-187.5° C.).

Example 347

Glutaric acid (4-benzyl-4-dimethylaminocyclohexyl)amide [2-4(-chlorophenyl)ethyl]amide hydrochloride, non-polar diastereoisomer As described for Example 341, 0.87 mg 4-[2-(4-chlorophenyl)ethyl-carbamoyl]butyric acid and 1.0 g 4-benzyl-4-dimethylaminocyclohexanone were converted in 5 ml DMF in the presence of 0.59 ml N,N-diisopropylcarbodiimide and 0.5 g 1-hydroxybenzotriazole and the crude product (1.80 g) similarly isolated. 900 mg of the non-polar diastereoisomer of glutaric acid (4-benzyl-4-dimethylaminocyclohexyl)amide [2-4(-chlorophenyl)ethyl] amide were obtained by chromatography on silica gel (3.0×20 cm) with 200 ml diethyl ether, followed by 200 ml diethyl ether/methanol (V:V=5:1), was dissolved in 20 ml 2-butanone and 20 ml ethyl acetate and converted into the corresponding hydrochloride by adding 33.5 µl water and 236 µl chlorotrimethylsilane and then evaporating to dryness (980 mg of vitreous solid).

Example 348

Glutaric acid (4-benzyl-4-dimethylaminocyclohexyl)amide [2-(4-chlorophenyl)ethyl]amide hydrochloride, polar diastereoisomer As described for Example 347, 335 mg of the polar diastereoisomer of glutaric acid (4-benzyl-4-dimethylaminocyclohexyl)amide [2-(4-chlorophenyl)ethyl]amide were obtained, which, dissolved in 30 ml 2-butanone, 30 ml ethyl acetate and 2 ml methanol, were converted into the corresponding hydrochloride by adding 12.5 µl water, 88 µl chlorotrimethylsilane and 10 ml diisopropylether (255 mg of white solid).

Tests on the Efficacy of the Compounds According to the Invention:

Measurement of ORL1 Binding

The cyclohexane derivatives of general formula I were examined in a receptor binding assay with $^3$H-nociceptin/orphanin FQ with membranes of recombinant CHO-ORL1 cells. This test system was carried out according to the methods presented by Ardati et al (Mol. Pharmacol., 51, 1997, pp. 816-824). The concentration of $^3$H-nociceptin/orphanin FQ was 0.5 nM in these tests. The binding assays were carried out with 20 µg membrane protein per 200 µl batch in 50 mM Hepes, pH 7.4, 10 mM $MgCl_2$ and 1 mM EDTA. The binding with the ORL1 receptor was determined by using 1 mg WGA-SPA beads (Amersham-Pharmacia, Freiburg), by incubation of the batch for one hour at RT and subsequent measurement in the Trilux scintillation counter (Wallac, Finland). The affinity is shown in Table 1 as a nanomolar $K_i$ value in or % inhibition at c=1 µM.

Measurement of µ-Binding

The receptor affinity for human p-opiate receptor was determined in a homogenous batch in microtitre plates. For this purpose, dilution series of the respective substituted cyclohexyl-1,4-diamine derivative to be tested were incubated with a receptor membrane preparation (15-40 µg protein per 250 µl incubation batch) of CHO-K1 cells, which express the human µ-opiate receptor (RB-HOM receptor membrane preparation from NEN, Zaventem, Belgium) in the presence of 1 nmol/l of the radioactive ligand [$^3$H]-naloxone (NET719, NEN, Zaventem, Belgium) and 1 mg WGA-SPA beads (wheat germ agglutinin SPA beads from Amersham/Pharmacia, Freiburg, Germany) in a total volume of 250 μl for 90 minutes at room temperature. 50 mmol/l tris-HCl were added as an incubation buffer with 0.05% by weight sodium azide and 0.06% by weight bovine serum albumin. 25 μmol/l naloxone were also added to determine the non-specific binding. At the end of the 90-minute incubation period, the microtitre plates were centrifuged off for 20 minutes at 1000 g and the radioactivity measured in a β-counter (Microbeta-Trilux, PerkinElmer Wallac, Freiburg, Germany). The percentage displacement of the radioactive ligand from its binding with the human p-opiate receptor at a concentration of the test substances of 1 μmol/l was determined and given as a percentage inhibition (% inhibition) of the specific binding. $IC_{50}$ inhibition concentrations, which bring about a 50% displacement of the radioactive ligand, were partially calculated by taking as a basis the percentage displacement by various concentrations of the compounds of general formula I to be tested. Ki values for the test substances were obtained as a result of conversion by means of the Cheng-Prusoff equation.

Measurement of Serotonin Re-Uptake

In order to carry out these in vitro studies, synaptosomes were freshly isolated from areas of rats' brains. In each case, what is known as a "$P_2$" fraction, which was prepared in accordance with Gray and Whittaker's directions (E. G. Gray and V. P. Whittaker (1962) J. Anat. 76, 79-88), was used. For the 5HT-uptake, these vesicular particles were isolated from the medulla+pons region of male rats' brains.

A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

Measurement of Noradrenalin Re-Uptake

In order to carry out these in vitro studies, synaptosomes were freshly isolated from rat brain areas. In each case, what is known as a "$P_2$" fraction, which was prepared in accordance with Gray and Whittaker's directions (E. G. Gray and V. P. Whittaker (1962) J. Anat. 76, 79-88), was used. For the NA-uptake, these vesicular particles were isolated from the hypothalamus of male rats' brains.

A detailed description of the method can be found in the literature (M. Ch. Frink, H. H. Hennies, W. Englberger, M. Haurand and B. Wilffert (1996) Arzneim.-Forsch./Drug Res. 46 (III), 11, 1029-1036).

The following binding data was determined, by way of example:

| Example | ORL1-binding, [1 μM], % inhibition |
|---------|------------------------------------|
| 249 | 49 |
| 250 | 76 |
| 251 | 96 |
| 252 | 88 |
| 253 | 92 |
| 254 | 88 |
| 255 | 69 |
| 256 | 95 |
| 257 | 94 |
| 258 | 68 |
| 259 | 73 |
| 260 | 80 |
| 261 | 90 |
| 262 | 57 |
| 263 | 79 |
| 264 | 99 |
| 265 | 77 |
| 266 | 96 |
| 267 | 95 |
| 268 | 98 |
| 269 | 86 |
| 270 | 92 |
| 271 | 78 |
| 272 | 39 |
| 273 | 96 |
| 274 | 64 |
| 275 | 85 |
| 276 | 98 |
| 277 | 86 |
| 278 | 96 |
| 279 | 82 |
| 280 | 96 |
| 281 | 77 |
| 282 | 82 |
| 283 | 76 |
| 284 | 84 |
| 285 | 99 |
| 286 | 72 |
| 287 | 79 |
| 288 | 75 |
| 289 | 86 |
| 290 | 95 |
| 291 | 78 |
| 292 | 93 |
| 293 | 81 |
| 294 | 100 |
| 295 | 98 |
| 296 | 97 |
| 297 | 74 |
| 298 | 73 |
| 299 | 90 |
| 300 | 95 |
| 301 | 99 |
| 302 | 72 |
| 303 | 99 |
| 304 | 98 |
| 305 | 99 |
| 306 | 72 |
| 307 | 98 |
| 308 | 71 |
| 309 | 100 |
| 310 | 98 |
| 311 | 90 |
| 312 | 100 |
| 313 | 71 |
| 314 | 88 |
| 315 | 60 |
| 316 | 77 |
| 317 | 91 |
| 318 | 94 |
| 319 | 97 |
| 320 | 98 |
| 321 | 90 |
| 322 | 98 |
| 323 | 97 |
| 324 | 96 |
| 325 | 98 |
| 326 | 91 |
| 327 | 93 |
| 328 | 94 |
| 329 | 97 |
| 330 | 99 |
| 331 | 92 |
| 332 | 98 |
| 333 | 92 |
| 334 | 95 |
| 335 | 94 |
| 336 | 99 |
| 337 | 96 |
| 338 | 98 |
| 339 | 98 |
| 340 | 84 |

| Example | μ-binding, [1 μM], % inhibition |
|---|---|
| 15 | 59 |
| 31 | 53 |
| 40 | 57 |
| 42 | 64 |
| 55 | 50 |
| 59 | 55 |
| 63 | 65 |
| 64 | 67 |
| 66 | 57 |
| 69 | 58 |
| 74 | 56 |
| 76 | 54 |
| 77 | 62 |
| 78 | 54 |
| 80 | 51 |
| 82 | 60 |
| 90 | 89 |
| 95 | 56 |
| 97 | 59 |
| 110 | 55 |
| 115 | 59 |
| 116 | 50 |
| 117 | 68 |
| 118 | 59 |
| 119 | 70 |
| 120 | 58 |
| 121 | 50 |
| 124 | 80 |
| 125 | 87 |
| 127 | 64 |
| 128 | 64 |
| 129 | 56 |
| 130 | 60 |
| 131 | 66 |
| 132 | 70 |
| 136 | 62 |
| 141 | 58 |
| 142 | 70 |
| 143 | 57 |
| 144 | 67 |
| 145 | 66 |
| 146 | 58 |
| 147 | 66 |
| 148 | 64 |
| 149 | 54 |
| 150 | 67 |
| 151 | 90 |
| 152 | 68 |
| 153 | 67 |
| 154 | 57 |
| 155 | 66 |
| 156 | 69 |
| 157 | 54 |
| 159 | 80 |
| 160 | 62 |
| 161 | 52 |
| 162 | 50 |
| 163 | 51 |
| 164 | 58 |
| 167 | 59 |
| 169 | 60 |
| 170 | 68 |
| 171 | 67 |
| 172 | 58 |
| 173 | 90 |
| 174 | 72 |
| 175 | 84 |
| 176 | 56 |
| 177 | 56 |
| 178 | 60 |
| 179 | 56 |
| 180 | 59 |
| 181 | 50 |
| 182 | 53 |
| 183 | 61 |
| 184 | 51 |
| 185 | 57 |

-continued

| Example | μ-binding, [1 μM], % inhibition |
|---|---|
| 186 | 55 |
| 187 | 53 |
| 188 | 50 |
| 189 | 61 |
| 190 | 54 |
| 191 | 59 |
| 192 | 54 |
| 193 | 51 |
| 194 | 68 |
| 195 | 51 |
| 196 | 50 |
| 197 | 74 |
| 198 | 62 |
| 199 | 50 |
| 200 | 55 |
| 201 | 69 |
| 202 | 67 |
| 203 | 56 |
| 204 | 52 |
| 205 | 51 |
| 206 | 56 |
| 207 | 57 |
| 208 | 50 |
| 209 | 67 |
| 210 | 57 |
| 211 | 56 |
| 212 | 77 |
| 213 | 73 |
| 214 | 58 |
| 215 | 54 |
| 216 | 65 |
| 217 | 54 |
| 218 | 62 |
| 219 | 60 |

| Example | 5HT-uptake [10 μM], % inhibition |
|---|---|
| 1 | 93 |
| 2 | 95 |
| 3 | 94 |
| 4 | 92 |
| 5 | 93 |
| 6 | 96 |
| 7 | 93 |
| 8 | 92 |
| 9 | 93 |
| 10 | 92 |
| 11 | 92 |
| 12 | 92 |
| 13 | 92 |
| 14 | 95 |
| 15 | 92 |
| 16 | 97 |
| 17 | 93 |
| 18 | 94 |
| 19 | 93 |
| 20 | 92 |
| 21 | 95 |
| 22 | 95 |
| 23 | 92 |
| 24 | 92 |
| 25 | 97 |
| 26 | 93 |
| 27 | 95 |
| 28 | 92 |
| 29 | 94 |
| 30 | 93 |
| 31 | 97 |
| 32 | 99 |
| 33 | 95 |
| 34 | 97 |

| Example | 5HT-uptake [10 µM], % inhibition |
|---|---|
| 35 | 94 |
| 36 | 96 |
| 37 | 95 |
| 38 | 95 |
| 39 | 94 |
| 40 | 94 |
| 41 | 92 |
| 42 | 97 |
| 43 | 98 |
| 44 | 94 |
| 45 | 92 |
| 46 | 92 |
| 47 | 93 |
| 48 | 94 |
| 49 | 92 |
| 50 | 92 |
| 51 | 92 |
| 52 | 96 |
| 53 | 93 |
| 54 | 95 |
| 56 | 95 |
| 57 | 93 |
| 58 | 93 |
| 60 | 93 |
| 61 | 92 |
| 62 | 100 |
| 63 | 94 |
| 64 | 96 |
| 65 | 92 |
| 66 | 94 |
| 67 | 98 |
| 68 | 98 |
| 70 | 93 |
| 71 | 92 |
| 72 | 95 |
| 73 | 93 |
| 74 | 96 |
| 75 | 97 |
| 76 | 96 |
| 79 | 96 |
| 81 | 92 |
| 82 | 92 |
| 83 | 93 |
| 84 | 95 |
| 85 | 94 |
| 86 | 92 |
| 87 | 96 |
| 88 | 97 |
| 89 | 94 |
| 90 | 96 |
| 91 | 92 |
| 92 | 92 |
| 93 | 92 |
| 94 | 92 |
| 95 | 93 |
| 96 | 94 |
| 98 | 92 |
| 99 | 94 |
| 100 | 92 |
| 101 | 94 |
| 102 | 94 |
| 103 | 94 |
| 104 | 93 |
| 105 | 92 |
| 106 | 93 |
| 107 | 95 |
| 108 | 94 |
| 110 | 100 |
| 111 | 96 |
| 112 | 96 |
| 113 | 97 |
| 114 | 99 |
| 122 | 93 |
| 123 | 92 |
| 126 | 93 |
| 133 | 93 |
| 134 | 92 |
| 135 | 92 |
| 137 | 94 |
| 138 | 92 |
| 139 | 93 |
| 140 | 93 |
| 141 | 94 |
| 165 | 92 |
| 168 | 92 |

| Example | NA-uptake [10 µM], % inhibition |
|---|---|
| 1 | 71 |
| 2 | 87 |
| 3 | 89 |
| 4 | 89 |
| 5 | 80 |
| 6 | 91 |
| 7 | 91 |
| 8 | 85 |
| 9 | 91 |
| 10 | 78 |
| 11 | 77 |
| 12 | 95 |
| 13 | 72 |
| 14 | 78 |
| 15 | 85 |
| 16 | 86 |
| 17 | 82 |
| 18 | 84 |
| 19 | 74 |
| 20 | 90 |
| 21 | 83 |
| 22 | 93 |
| 23 | 92 |
| 24 | 91 |
| 25 | 95 |
| 26 | 79 |
| 27 | 92 |
| 28 | 81 |
| 29 | 91 |
| 30 | 96 |
| 31 | 102 |
| 32 | 97 |
| 33 | 99 |
| 34 | 87 |
| 35 | 95 |
| 36 | 93 |
| 37 | 100 |
| 38 | 79 |
| 39 | 90 |
| 40 | 96 |
| 41 | 90 |
| 42 | 97 |
| 43 | 96 |
| 44 | 84 |
| 45 | 77 |
| 46 | 89 |
| 47 | 73 |
| 48 | 97 |
| 49 | 98 |
| 50 | 89 |
| 51 | 77 |
| 52 | 88 |
| 53 | 94 |
| 54 | 90 |
| 56 | 96 |
| 57 | 100 |
| 58 | 79 |
| 60 | 71 |
| 61 | 93 |
| 62 | 86 |

-continued

| Example | NA-uptake [10 μM], % inhibition |
|---|---|
| 63 | 94 |
| 64 | 102 |
| 65 | 84 |
| 66 | 92 |
| 67 | 96 |
| 68 | 85 |
| 70 | 96 |
| 71 | 94 |
| 72 | 70 |
| 73 | 87 |
| 74 | 98 |
| 75 | 99 |
| 76 | 101 |
| 79 | 95 |
| 81 | 91 |
| 82 | 94 |
| 83 | 105 |
| 84 | 96 |
| 85 | 100 |
| 86 | 76 |
| 87 | 94 |
| 88 | 102 |
| 89 | 98 |
| 90 | 109 |
| 91 | 101 |
| 92 | 89 |
| 93 | 75 |
| 94 | 86 |
| 95 | 99 |
| 96 | 87 |
| 98 | 74 |
| 99 | 99 |
| 100 | 77 |
| 101 | 77 |
| 102 | 105 |
| 103 | 108 |
| 104 | 84 |
| 105 | 90 |
| 106 | 98 |
| 107 | 106 |
| 108 | 100 |
| 110 | 95 |
| 111 | 97 |
| 112 | 101 |
| 113 | 94 |
| 114 | 106 |
| 122 | 102 |
| 123 | 99 |
| 126 | 84 |
| 133 | 97 |
| 134 | 101 |
| 135 | 96 |
| 137 | 83 |
| 138 | 84 |
| 139 | 95 |
| 140 | 77 |
| 141 | 99 |
| 165 | 94 |
| 168 | 96 |

Parenteral Solution of a Substituted cyclohexyl-1,4-diamine Derivative According to the Invention 38 g of one of the substituted cyclohexyl-1,4-diamine derivatives according to the invention, here Example 1, were dissolved at room temperature in 1 l water for injection purposes and then adjusted to isotonic conditions for injection purposes by adding anhydrous glucose.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A cyclohexyl-1,4-diamine compound corresponding to formula I,

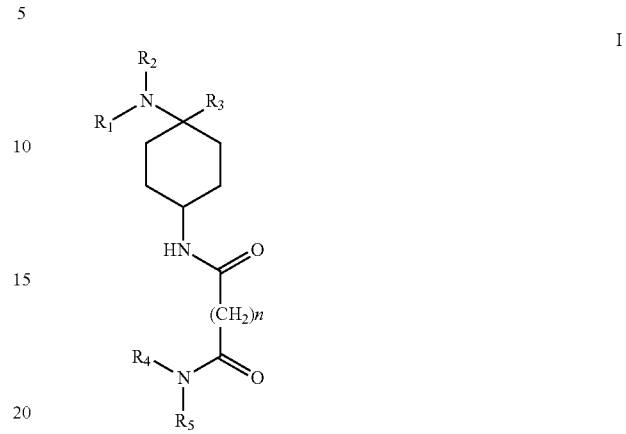

wherein n represents 1, 2, 3, 4 or 5

$R^1$ and $R^2$ independently of one another represent H; saturated or unsaturated, branched or unbranched, singly or multiply substituted or unsubstituted $C_{1-5}$ alkyl; singly or multiply substituted or unsubstituted $C_{3-8}$ cycloalkyl; or singly or multiply substituted or unsubstituted aryl, $C_{3-8}$ cycloalkyl or heteroaryl bound by $C_{1-3}$ alkyl;

or $R^1$ and $R^2$ together form a ring and represent $CH_2CH_2OCH_2CH_2$, $CH_2CH_2NR^{10}CH_2CH_2$ or $(CH2)_{3-6}$, wherein $R^{10}$ represents H; saturated or unsaturated, branched or unbranched, singly or multiply substituted or unsubstituted $C_{1-5}$ alkyl singly or multiply substituted or unsubstituted $C_{3-8}$ cycloalkyl; singly or multiply substituted or unsubstituted aryl or heteroaryl; or singly or multiply substituted or unsubstituted aryl, $C_{3-8}$ cycloalkyl or heteroaryl bound by $C_{1-3}$ alkyl; substituted or unsubstituted C(O)phenyl, C(O)heteroaryl, C(O)$C_{1-5}$ alkyl;

$R^3$ represents saturated or unsaturated, branched or unbranched, singly or multiply substituted or unsubstituted $C_{1-5}$ alkyl; singly or multiply substituted or unsubstituted $C_{3-8}$ cycloalkyl; unsubstituted or singly or multiply substituted aryl or heteroaryl; unsubstituted or singly or multiply substituted aryl, heteroaryl or $C_{3-8}$ cycloalkyl bound by a $C_{1-3}$ alkyl group;

$R^4$ represents —$(CR^6R^7)_pR^8$, wherein p represents 0, 1, 2, 3 or 4;

$R^6$ represents H or saturated or unsaturated, branched or unbranched, unsubstituted or singly or multiply substituted $C_{1-5}$ alkyl;

$R^7$ represents H, saturated or unsaturated, branched or unbranched, unsubstituted or singly or multiply substituted $C_{1-5}$ alkyl or COOR$^9$;

or $R^6$ and $R^7$ together form a ring and represent $(CH_2)_kCHR^8(CH_2)_m$, where k =1, 2, or 3 and m =1 or 2;

$R^8$ represents respectively saturated or unsaturated, branched or unbranched, unsubstituted or singly or multiply substituted $C_{1-6}$ alkyl; unsubstituted or singly or multiply substituted $C_{3-8}$ cycloalkyl, aryl or heteroaryl;

$R^9$ represents H or $C_{1-5}$ alkyl;

$R^5$ represents H or —$(CH_2)_1R^8$, wherein l represents 1, 2 or 3 or $R^5$ and $R^4$ together form a ring and represent $CH_2CHR^{14}OCHR^{14}CH_2$, $CH_2CH_2SCH_2CH_2$ $CH_2CH_2NR^{11}CH_2CH_2$, $(CR^{12}R^{13})_{3-6}$ or

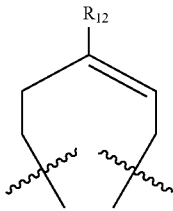

wherein $R^{11}$ represents H; saturated or unsaturated, branched or unbranched, singly or multiply substituted or unsubstituted $C_{1-5}$ alkyl; saturated or unsaturated, singly or multiply substituted or unsubstituted $C_{3-8}$ cycloalkyl; singly or multiply substituted or unsubstituted aryl or heteroaryl; or singly or multiply substituted or unsubstituted aryl, $C_{3-8}$ cycloalkyl or heteroaryl bound by $C_{1-3}$ alkyl;

$R^{12}$ represents H; saturated or unsaturated, branched or unbranched, singly or multiply substituted or unsubstituted $C_{1-5}$ alkyl; OH; unsubstituted or singly or multiply substituted C(O)phenyl; singly or multiply substituted or unsubstituted $C_{3-8}$ cycloalkyl; respectively singly or multiply substituted or unsubstituted aryl or heteroaryl; or singly or multiply substituted or unsubstituted aryl, $C_{3-8}$ cycloalkyl or heteroaryl bound by $C_{1-3}$ alkyl;

and $R^{13}$ represents H or OH or together with $R^{12}$ via the same C atom or an adjacent C atom forms a five-membered or six-membered ring which may contain heteroatoms, be saturated or unsaturated, substituted or unsubstituted or be part of a polycyclic system;

$R^{14}$ represents respectively saturated or unsaturated, branched or unbranched, singly or multiply substituted or unsubstituted $C_{1-3}$ alkyl;

or an acid, base or a physiologically acceptable salt thereof.

2. The compound of claim 1, wherein said compound is present in the form of a pure enantiomer or pure diastereoisomer.

3. The compound of claim 1, wherein said compound is present in the form of a mixture of stereoisomers.

4. The compound of claim 1, wherein said compound is present in the form of a racemic mixture.

5. A cyclohexyl-1,4-diamine compound according to claim 1, wherein
$R^1$ and $R^2$ independently of one another represent H; saturated or unsaturated, branched or unbranched, singly or multiply substituted or unsubstituted $C_{1-5}$ alkyl;
or $R^1$ and $R^2$ together form a ring and represent $CH_2CH_2OCH_2CH_2$, $CH_2CH_2NR^{10}CH_2CH_2$ or $(CH2)_{3-6}$,
wherein $R^{10}$ represents H; saturated or unsaturated, branched or unbranched, singly or multiply substituted or unsubstituted $C_{1-5}$ alkyl.

6. A cyclohexyl-1,4-diamine compound according to claim 1, wherein $R^1$ and $R^2$ independently of one another represent $CH_3$ or H, wherein $R^1$ and $R^2$ do not simultaneously represent H, or $R^1$ and $R^2$ together form a ring and represent $CH_2CH_2OCH_2CH_2$ or $(CH_2)_6$.

7. A cyclohexyl-1,4-diamine compound according to claim 1, wherein $R^3$ represents unsubstituted or singly or multiply substituted cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl; respectively unsubstituted or singly or multiply substituted $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bound by a saturated, unbranched $C_{1-2}$ alkyl.

8. A cyclohexyl-1,4-diamine compound according to claim 1, wherein $R^3$ represents unsubstituted or singly or multiply substituted phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl; unsubstituted or singly or multiply substituted phenyl, furyl or thiophenyl bound by a saturated, unbranched $C_{1-2}$ alkyl group.

9. A cyclohexyl-1,4-diamine compound according to claim 1, wherein $R^3$ represents substituted or unsubstituted phenyl, thiophenyl, pyridyl or benzyl, more preferably 4-methylbenzyl, 3-chlorobenzyl, 4-chlorobenzyl, 3-methylbenzyl, benzyl, phenyl, thiophenyl or 3-fluorophenyl.

10. A cyclohexyl-1,4-diamine compound according to claim 1, wherein n represents 2 or 3.

11. A cyclohexyl-1,4-diamine compound according to claim 1, wherein $R^4$ represents —$(CR^6R^7)_pR^8$ and $R^5$ represents H.

12. A cyclohexyl-1,4-diamine compound according to claim 1, wherein $R^4$ represents $(CH_2)_pR^8$ and $R^5$ represents —$(CH_2)_rR^8$.

13. A cyclohexyl-1,4-diamine compound according to claim 1, wherein $R^4$ and $R^5$ together represent $CH_2CHR^{14}OCHR^{14}CH_2$, $CH_2CH_2SCH_2CH_2$, $CH_2CH_2NR^{11}CH_2CH_2$ $(CR^{12}R^{13})_{3-6}$ or

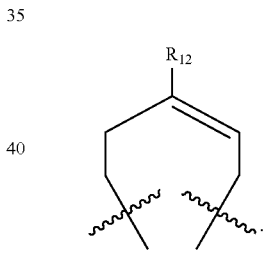

14. A cyclohexyl-1,4-diamine compound according to claim 1, wherein $R^6$ represents H and $R^7$ represents H, $CH_3$, unsubstituted or singly or multiply substituted benzyl, or $COOR^9$ or $R^6$ and $R^7$ together form a ring and represent $(CH_2)_kCHR^8(CH_2)_m$.

15. A cyclohexyl-1,4-diamine compound according to claim 1, wherein $R^8$ represents saturated or unsaturated, branched or unbranched, unsubstituted or singly or multiply substituted $C_{1-6}$ alkyl; unsubstituted or singly or multiply substituted cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyrrolidinyl, tetrahydrofuryl, piperazinyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl.

16. A cyclohexyl-1,4-diamine compound according to claim 1, wherein $R^8$ represents saturated or unsaturated, branched or unbranched, unsubstituted or singly or multiply substituted $C_{1-6}$ alkyl; unsubstituted or singly or multiply substituted pyrrolidinyl, morpholinyl, tetrahydrofuryl, tetrahydronaphthyl, dihydroindolyl, pyridyl, thienyl, piperazinyl, naphthyl, indanyl, quinolinyl, cyclopropyl, cyclopentyl, cyclohexyl, cycloheptyl, cyclooctyl, adamantyl, furyl, benzofuryl, phenyl or indolyl.

17. A cyclohexyl-1,4-diamine compound according to claim 1, wherein said compound is selected from the group consisting of:

- N-[1-(2,6-dichloro-benzyl)-pyrrolidin-3-yl]-N'-[4-dimethylamino-4-(4-methyl-benzyl)-cyclohexyl]-succinamide;
- N-[4-(3-chloro-benzyl)-4-dimethylamino-cyclohexyl]-N'-(2-oxo-tetrahydro-furan-3-yl)-succinamide;
- N-[4-(4-chloro-benzyl)-4-dimethylamino-cyclohexyl]-N'-(3,3-diphenyl-propyl)-succinamide;
- N-[4-dimethylamino-4-(4-methyl-benzyl)-cyclohexyl]-4-[4-(7-methoxy-benzo[1,3]dioxol-5-yl-methyl)-piperazin-1-yl]-4-oxo-butyramide;
- N-[4-(4-chloro-benzyl)-4-dimethylamino-cyclohexyl]-4-(3,6-dihydro-2H-pyridin-1-y1)-4-oxo-butyramide;
- N-[4-dimethylamino-4-(4-methyl-benzyl)-cyclohexyl]-4-oxo-4-(4-m-tolyl-piperazin-1-yl)-butyramide;
- 2-{3-[4-(4-chloro-benzyl)-4-dimethylamino-cyclohexylcarbamoyl]-propionylamino}-propanoic acid ethylester;
- N-[4-(3-chloro-benzyl)-4-dimethylamino-cyclohexyl]-4-(8-fluoro-1,3,4,5-tetrahydro-pyrido[4,3-b]indol-2-yl)-4-oxo-butyramide;
- 3-{3-[4-dimethylamino-4-(4-methyl-benzyl)-cyclohexylcarbamoyl]-propionylamino}-propanoic acid ethylester;
- N-[4-dimethylamino-4-(4-methyl-benzyl)-cyclohexyl]-4-[4-(5-methyl-pyrazin-2-carbonyl)-piperazin -1-yl]-4-oxo-butyramide;
- N-[4-dimethylamino-4-(4-methyl-benzyl)-cyclohexyl]-N'-methyl-N'-[2-(2,2,2-trifluoro-acetylamino)-ethyl]-succinamide;
- N-[4-(3-chloro-benzyl)-4-dimethylamino-cyclohexyl]-N'-(2-pyridin-2-yl-ethyl)-succinamide;
- N-[4-(4-chloro-benzyl)-4-dimethylamino-cyclohexyl]-4-oxo-4-thiomorpholin-4-yl-butyramide;
- N-[4-(4-chloro-benzyl)-4-dimethylamino-cyclohexyl]-4-[4-(5-methyl-pyrazin-2-carbonyl)-piperazin -1-yl]-4-oxo-butyramide;
- N-[4-dimethylamino-4-(3-methyl-benzyl)-cyclohexyl]-N'-(2-thiophen-2-yl-ethyl)-succinamide;
- N-[4-(4-chloro-benzyl)-4-dimethylamino-cyclohexyl]-4-[4-(4-ethoxy-phenyl)-piperazin-1-yl]-4-oxo-butyramide;
- N-allyl-N'-[4-(4-chloro-benzyl)-4-dimethylamino-cyclohexyl]-N-methyl-succinamide;
- 5-[4-(2,5-dimethoxy-benzyl)-piperazin-1-yl]-5-oxo-valeric acid (4-benzyl-4-dimethylamino-cyclohexyl)-amide;
- 4-(3,6-dihydro-2H-pyridin-1-yl)-N-[4-dimethylamino-4-(4-methyl-benzyl)-cyclohexyl]-4-oxo-butyramide;
- N-[4-dimethylamino-4-(3-methyl-benzyl)-cyclohexyl]-4-(4-methyl-piperidin-1-yl)-4-oxo-butyramide;
- N-[4-dimethylamino-4-(4-methyl-benzyl)-cyclohexyl]-4-oxo-4-(4-pyridin-2-yl-piperazin-1-yl)-butyramide;
- ({3-[4-dimethylamino-4-(3-methyl-benzyl)-cyclohexylcarbamoyl]-propionyl}-methyl-amino)-acetic acid benzyl ester;
- 4-[4-(2,6-dichloro-benzyl)-piperazin-1-yl]-N-[4-dimethylamino-4-(3-methyl-benzyl)-cyclohexyl]-4-oxo-butyramide;
- {[4-(4-benzyl-4-dimethylamino-cyclohexylcarbamoyl)-butyryl]-methyl-amino}-acetic acid tert butyl ester;
- 5-[4-(2-fluoro-5-methoxy-benzyl)-piperazin-1-yl]-5-oxo-valeric acid (4-benzyl-4-dimethylamino-cyclohexyl)-amide;
- N-[4-(4-chloro-benzyl)-4-dimethylamino-cyclohexyl]-N'-(3-methoxy-propyl)-succinamide;
- 4-[4-(4-acetyl-phenyl)-piperazin-1-yl]-N-[4-dimethylamino-4-(4-methyl-benzyl)-cyclohexyl]-4-oxo-butyramide;
- 4-{3-[4-dimethylamino-4-(4-methyl-benzyl)-cyclohexylcarbamoyl]-propionyl}-piperazin-1-carboxylic acid-tert-butylester;
- N-[4-(3-chloro-benzyl)-4-dimethylamino-cyclohexyl]-N'-(tetrahydro-furan-2-ylmethyl)-succinamide;
- 2-{3-[4-(3-chloro-benzyl)-4-dimethylamino-cyclohexylcarbamoyl]-propionylamino}-propanoic acid ethylester;
- N-(3-bromo-benzyl)-N'-[4-dimethylamino-4-(3-methyl-benzyl)-cyclohexyl]-succinamide;
- 3-(4-chloro-phenyl)-2-{3-[4-dimethylamino-4-(4-methyl-benzyl)-cyclohexylcarbamoyl]-propionylamino}-prop anoic acid methylester;
- N-[4-(3-chloro-benzyl)-4-dimethylamino-cyclohexyl]-4-[4-(5-methyl-pyrazin-2-carbonyl)-piperazin-1-yl]-4-oxo-butyramide;
- N-[4-(4-chloro-benzyl)-4-dimethylamino-cyclohexyl]-N'-naphthalen-1-ylmethyl-succinamide;
- N-[4-dimethylamino-4-(3-methyl-benzyl)-cyclohexyl]-4-[4-(3-fluoro-4-methoxy-benzyl)-piperazin-1-yl]-4-oxo-butyramide;
- N-[4-dimethylamino-4-(4-methyl-benzyl)-cyclohexy]N'-[2-(1H-indol-3-yl)-ethyl]-N'-methyl-succinamide;
- (4-{3-[4-(3-chloro-benzyl)-4-dimethylamino-cyclohexylcarbamoyl]-propionylamino}-benzyl)-phosphonic acid diethylester;
- N-[4-dimethylamino-4-(4-methyl-benzyl)-cyclohexyl]-N'-methyl-N'-(2-pyridin-2-yl-ethyl)-succinamide;
- N-[4-(3-chloro-benzyl)-4-dimethylamino-cyclohexyl]-4-(3,6-dihydro-2H-pyridin-1-yl)-4-oxo-butyramide;
- N-[4-dimethylamino-4-(3-methyl-benzyl)-cyclohexyl]-N'-(1-methyl-3-phenyl-propyl)-succinamide;
- 5-[4-(5-methyl-pyrazin-2-carbonyl)-piperazin-1-yl]-5-oxo-valeric acid (4-benzyl-4-dimethylamino-cyclohexyl)-amide;
- N-[4-(3-chloro-benzyl)-4-dimethylamino-cyclohexyl]-N'-(2-chloro-6-methyl-benzyl)-succinamide;
- N-allyl-N'-[4-(3-chloro-benzyl)-4-dimethylamino-cyclohexyl]-N-methyl-succinamide;
- N-[4-(4-chloro-benzyl)-4-dimethylamino-cyclohexyl]-N'-cyclopentyl-succinamide;
- N-[4-dimethylamino-4-(4-methyl-benzyl)-cyclohexyl]-N'-(tetrahydro-furan-2-ylmethyl)-succinamide;
- (4-{3-[4-dimethylamino-4-(3-methyl-benzyl)-cyclohexylcarbamoyl]-propionylamino}-benzyl)-phosphonic acid diethylester;
- N-[4-(4-chloro-benzyl)-4-dimethylamino-cyclohexyl]-4-[4-(2-methoxy-phenyl)-piperazin-1-yl]-4-oxo-butyramide;
- N-[4-dimethylamino-4-(3-methyl-benzyl)-cyclohexyl]-4-[4-(3-methoxy-phenyl)-piperazin-1-yl]-4-oxo-butyramide;
- N-[4-(4-chloro-benzyl)-4-dimethylamino-cyclohexyl]-N'-(3,5-difluoro-benzyl)-succinamide;

N-[4-(4-chloro-benzyl)-4-dimethylamino-cyclohexyl]-N'-(2-methyl-benzyl)-succinamide;
N-[4-dimethylamino-4-(4-methyl-benzyl)-cyclohexyl]-4-oxo-4-{4-[(2,2,2-trifluoro-acetylamino)-methyl]-piperidin-1-yl}-butyramide;
N-[4-(4-chloro-benzyl)-4-dimethylamino-cyclohexyl]-N'-[2-(1H-indol-3-yl)-ethyl]-succinamide;
N-[4-(3-chloro-benzyl)-4-dimethylamino-cyclohexyl]-N'-[2-(1H-indol-3-yl)-ethyl]-N'-methyl-succinamide;
5-[4-(7-methoxy-benzo[1,3]dioxol-5-ylmethyl)-piperazin-1-yl]-5-oxo-valeric acid (4-benzyl-4-dimethylamino-cyclohex/1)-amide;
N-benzyl-N'-[4-dimethylamino-4-(3-methyl-benzyl)-cyclohexyl]-N-(2-hydroxy-ethyl)-succinamide;
5-[4-(2,3-dimethyl-phenyl)-piperazin-1-yl]-5-oxo-valeric acid (4-benzyl-4-dimethylamino-cyclohexyl)-amide;
N-[4-(4-chloro-benzyl)-4-dimethylamino-cyclohexyl]-N'-[2-(1H-indol-3-yl)-ethyl]-N'-methyl-succinamide;
N-[4-dimethylamino-4-(4-methyl-benzyl)-cyclohexyl]-4-[4-(2,3-dimethyl-phenyl)-piperazin-1-yl]-4-oxo-butyramide;
Glutaric acid-(4-benzyl-4-dimethylamino-cyclohexyl)-amide (1,2,3,4-tetrahydro-naphthalen-1-yl)-amide;
N-[4-(4-chloro-benzyl)-4-dimethylamino-cyclohexyl]-4-(4-methyl-piperidin-1-yl)-4-oxobutyramide;
2-{3-[4-dimethylamino-4-(4-methyl-benzyl)-cyclohexylcarbamoyl]-propionylamino}-propanoic acid-tert-butylester;
5-(4-cycloheptyl-piperazin-1-yl)-5-oxo-valeric acid (4-benzyl-4-dimethylamino-cyclohexyl)-amide;
Glutaric acid-(4-benzyl-4-dimethylamino-cyclohexyl)-amide [2-(4-fluoro-phenyl)-ethyl]-amide;
Glutaric acid-(4-benzyl-4-dimethylamino-cyclohexyl)-amide [1-(2,6-dichloro-benzyl)-pyrrolidin-3-yl]-amide;
N-[4-(4-chloro-benzyl)-4-dimethylamino-cyclohexyl]-4-(1,4-dioxa-8-aza-spiro[4.5]dec-8-yl)-4-oxo-butyramide;
N-[4-(3-chloro-benzyl)-4-dimethylamino-cyclohexyl]-4-oxo-4-thiomorpholin-4-yl-butyramide;
4-(4-benzoyl-piperidin-1-yl)-N-[4-dimethylamino-4-(3-methyl-benzyl)-cyclohexyl]-4-oxo-butyramide;
N-[4-(4-chloro-benzyl)-4-dimethylamino-cyclohexyl]-N'-(2,4-dimethoxy-benzyl)-succinamide;
N-[4-dimethylamino-4-(3-methyl-benzyl)-cyclohexyl]-N'-(1,2,3,4-tetrahydro-naphthalen-1-yl)-succinamide;
N-[4-(4-chloro-benzyl)-4-dimethylamino-cyclohexyl]-N'-ethyl-N'-pyridin-4-ylmethyl-succinamide;
N-[2-(3,4-dimethoxy-phenyl)-ethyl]-N'-[4-dimethylamino-4-(3-methyl-benzyl)-cyclohexyl]-N-methyl-succinamide;
N-[4-(4-chloro-benzyl)-4-dimethylamino-cyclohexyl]-N'-methyl-N'-pyridin-3-ylmethyl-succinamide;
N-[4-(3-chloro-benzyl)-4-dimethylamino-cyclohexyl]-N'-pyridin-2-ylmethyl-succinamide;
N-[4-(3-chloro-benzyl)-4-dimethylamino-cyclohexyl]-N'-(2-methyl-benzyl)-succinamide;
N-[4-dimethylamino-4-(3-methyl-benzyl)-cyclohexyl]-N'-(4-methoxy-phenyl)-succinamide;
N-[4-dimethylamino-4-(3-methyl-benzyl)-cyclohexyl]-N'-indan-2-yl-succinamide;
N-[4-(3-chloro-benzyl)-4-dimethylamino-cyclohexyl]-N'-(1-methyl-3-phenyl-propyl)-succinamide;
N-(2-chloro-6-methyl-benzyl)-N'-[4-dimethylamino-4-(3-methyl-benzyl)-cyclohexyl]-succinamide;
N-[4-dimethylamino-4-(4-methyl-benzyl)-cyclohexyl]-4-[4-(4-methoxy-phenyl)-piperazin-1-yl]-4-oxo-butyramide;
N-[4-dimethylamino-4-(4-methyl-benzyl)-cyclohexyl]-N'-[2-(4-fluoro-phenyl)-ethyl]-succinamide;
Glutaric acid-(4-benzyl-4-dimethylamino-cyclohexyl)-amide 4-dimethylamino-benzylamide;
N-[4-(3-chloro-benzyl)-4-dimethylamino-cyclohexyl]-N'-(3,5-dichloro-benzyl)-succinamide;
N-[4-(4-chloro-benzyl)-4-dimethylamino-cyclohexyl]-N'-(1-methyl-3-phenyl-propyl)-succinamide;
4-{3-[4-(3-chloro-benzyl)-4-dimethylamino-cyclohexylcarbamoyl]-propionyl}-piperazin-1-carboxylic acid ethylester;
N-[4-dimethylamino-4-(3-methyl-benzyl)-cyclohexyl]-N'-(4-methoxy-benzyl)-succinamide;
N-[4-(4-chloro-benzyl)-4-dimethylamino-cyclohexyl]-4-(2,6-dimethyl-morpholin-4-y1)-4-oxo-butyramide;
N-[4-dimethylamino-4-(4-methyl-benzyl)-cyclohexyl]-4-oxo-4-(4-phenyl-3,6-dihydro-2H-pyridin-1-yl)-butyramide;
N-[4-(4-chloro-benzyl)-4-dimethylamino-cyclohexyl]-N'-[2-(3-fluoro-phenyl)-ethyl]-succinamide;
4-[4-(4-allyloxy-benzyp-piperazin-1-yl]-N-[4-dimethylamino-4-(3-methyl-benzyl)-cyclohexyl]-4-oxo-butyramide;
Glutaric acid-(4-benzyl-4-dimethylamino-cyclohexyl)-amide [2-(5-bromo-2-methoxy-phenyl)-ethyl]-amide;
5-[4-(3-methoxy-phenyl)-piperazin-1-yl]-5-oxo-valeric acid (4-benzyl-4-dimethylamino-cyclohexyl)-amide;
N-[4-(3-chloro-benzyl)- 4- dimethylamino-cyclohexyl]-4-(4-methyl-piperidin-1-yl)-4-oxo-butyramide;
(4-{3-[4-(4-chloro-benzyl)-4-dimethylamino-cyclohexylcarbamoyl]-propionylamino}-benzyl)-phosphonic acid diethylester;
N-[4-dimethylamino-4-(4-methyl-benzyl)-cyclohexyl]-4-oxo-4-(4-o-tolyl-piperazin-1-y1)-butyramide;
N-[4-dimethylamino-4-(3-methyl-benzyl)-cyclohexyl]-N'-[2-(3-fluoro-phenyl)-ethyl]-succinamide;
4-[4-(4-chloro-phenyl)-piperazin-1-yl]-N-[4-dimethylamino-4-(4-methyl-benzyl)-cyclohexyl]-4-oxo-butyramide;
N-[4-(3-chloro-benzyl)-4-dimethylamino-cyclohexyl]-N'-[1-(4-fluoro-phenyl)-ethyl]-succinamide;
N-[4-(4-chloro-benzyl)-4-dimethylamino-cyclohexyl]-N'-[1-(4-trifluoromethyl-benzyl)-pyrrolidin-3-yl]-succinamide;
N-[4-(3-chloro-benzyl)-4-dimethylamino-cyclohexyl]-N'-[2-(1H-indol-3-yl)-ethyl]-succinamide;
N-[4-(4-chloro-benzyl)-4-dimethylamino-cyclohexyl]-N'-indan-5-yl-succinamide;
N-(4-benzyloxy-phenyl)-N'-[4-dimethylamino-4-(4-methyl-benzyl)-cyclohexyl]-succinamide;
2-{3-[4-dimethylamino-4-(3-methyl-benzyl)-cyclohexylcarbamoyl]-propionylamino}-3-methyl-valeric acid tert-butyl ester;
4-(4-benzyl-piperidin-1-yl)-N-[4-dimethylamino-4-(3-methyl-benzyl)-cyclohexyl]-4-oxo-butyramide;
N-[4-(4-chloro-benzyl)-4-dimethylamino-cyclohexyl]-4-[4-(4-fluoro-phenyl)-3,6-dihydro-2H-pyridin-1-yl]-4-oxo-butyramide;
N-[4-dimethylamino-4-(4-methyl-benzyl)-cyclohexyl]-N'-(1,2-dimethyl-propyl)-succinamide;
N-[4-dimethylamino-4-(3-methyl-benzyl)-cyclohexyl]-4-(8-fluoro-1,3,4,5-tetrahydro-pyrido[4,3-b]indol-2-yl)-4-oxo-butyramide, 4-[4-(3-chloro-benzoyl)-piperazin-1-yl]-N-[4-dimethylamino-4-(3-methyl-benzyl)-cyclohexyl]-4-oxo-butyramide;
N-[4-(4-chloro-benzyl)-4-dimethylamino-cyclohexyl]-N'-(4-methoxy-phenyl)-succinamide;

5-[4-(2,6-dichloro-benzyl)-piperazin-1-yl]-5-oxo-valeric acid (4-benzyl-4-dimethylamino-cyclohexyl)-amide;
N-[4-dimethylamino-4-(3-methyl-benzyl)-cyclohexyl]-N'-[2-(1H-indol-3-yl)-ethyl]-N'-methyl-succinamide;
N-[4-dimethylamino-4-(3-methyl-benzyl)-cyclohexyl]-N'-[1-(4-fluoro-phenyl)-ethyl]-succinamide;
4-[4-(4-chloro-phenyl)-piperazin-1-yl]-N-[4-dimethylamino-4-(3-methyl-benzyl)-cyclohexyl]-4-oxo-butyramide;
N-[4-(3-chloro-benzyl)-4-dimethylamino-cyclohexyl]-4-oxo-4-(4-oxo-1-phenyl-1,3,8-triaza-spiro[4.5]dec-8-yl)-butyramide;
N-benzyl-N'-[4-dimethylamino-4-(3-methyl-benzyl)-cyclohexyl]-N-methyl-succinamide;
N-[4-(3-chloro-benzyl)-4-dimethylamino-cyclohexyl]-N'-(3,5-difluoro-benzyl)-succinamide;
N-[4-dimethylamino-4-(3-methyl-benzyl)-cyclohexyl]-N'-[2-(4-fluoro-phenyl)-ethyl]-succinamide;
N-[4-dimethylamino-4-(3-methyl-benzyl)-cyclohexyl]-N'-[2-(1H-indol-3-yl)-ethyl]-succinamide;
N-(2-benzylsulphanyl-ethyl)-N'-[4-dimethylamino-4-(3-methyl-benzyl)-cyclohexyl]-succinamide;
N-[4-(3-chloro-benzyl)-4-dimethylamino-cyclohexyl]-N'-(2,4-difluoro-benzyl)-succinamide;
N-[4-(3-chloro-benzyl)-4-dimethylamino-cyclohexyl]-N'-phenethyl-succinamide;
N-[4-dimethylamino-4-(3-methyl-benzyl)-cyclohexyl]-N'-(1-naphthalen-2-yl-ethyl)-succinamide;
N-[4-(3-chloro-benzyl)-4-dimethylamino-cyclohexyl]-N'-(1-methoxymethyl-2-phenyl-ethyl)-succinamide;
N-[4-(3-chloro-benzyl)-4-dimethylamino-cyclohexyl]-N'-(3,4-dichloro-benzyl)-succinamide;
N-[4-(3-chloro-benzyl)-4-dimethylamino-cyclohexyl]-N'-furan-2-ylmethyl-succinamide;
N-[4-dimethylamino-4-(4-methyl-benzyl)-cyclohexyl]-(1,2,3,4-tetrahydro-naphthalen-1-yl)-succinamide;
N-[4-(3-chloro-benzyl)-4-dimethylamino-cyclohexyl]-N'-(4-fluoro-benzyl)-succinamide;
N-[4-dimethylamino-4-(3-methyl-be nzyl)-cyclohexyl]-N'-indan-1-yl-succinamide;
N-[4-(3-chloro-benzyl)-4-dimethylamino-cyclohexyl]-4-(3,5-dimethyl-piperidin-1-yl )-4-oxo-butyramide;
N-[4-dimethylamino-4-(3-methyl-benzyl)-cyclohexyl]-N'-phenethyl-succinamide; N-[4-dimethylamino-4-(4-methyl-benzyl)-cyclohexyl]-N'-phenethyl-succinamide;
N-(2-benzylsulphanyl-ethyl)-N'-[4-(3-chloro-benzyl)-4-dimethylamino-cyclohexyl]-succinamide;
N-[4-(3-chloro-benzyl)-4-dimethylamino-cyclohexyl]-N'-(2,5-dichloro-benzyl)-succinamide;
4-[4-(3-chloro-benzoyl)-piperazin-1-yl]-N-[4-(4-chloro-benzyl)-4-dimethylamino-cyclohexyl]-4-oxo-butyramide;
N-[4-(4-chloro-benzyl)-4-dimethylamino-cyclohexyl]-N'-(1-phenyl-propyl)-succinamide;
N-(4-bromo-2-fluoro-benzyl)-N'-[4-dimethylamino-4-(3-methyl-benzyl)-cyclohexyl]-succinamide;
N-[4-(3-chloro-benzyl)-4-dimethylamino-cyclohexyl]-N'-methyl-N'-pyridin-3-ylmethyl-succinamide;
N-[4-dimethylamino-4-(4-methyl-benzyl)-cyclohexyl]-N'-(2-ethoxy-benzyl)-succinamide;
N-[4-dimethylamino-4-(3-methyl-benzyl)-cyclohhexyl]-N'-[2-(5-methoxy-1H-indol-3-yl)-ethyl]-succinamide;
N-(4-sec-butyl-phenyl)-N'-[4-(4-chloro-benzyl)-4-dimethylamino-cyclohexyl]-succinamide;
5-oxo-5-(4-phenyl-3,6-dihydro-2H-pyridin-1-yl)-valeric acid (4-benzyl-4-dimethylamino-cyclohexyl)-amide;
5-oxo-5-(4-phenyl-3,6-dihydro-2H-pyridin-1-yl)-valeric acid (4-benzyl-4-dimethylamino-cyclohexyl)-amide;
N-[4-(3-chloro-benzyl)-4-dimethylamino-cyclohexyl]-N'-[2-(3-fluoro-phenyl)-ethyl]-succinamide;
N-(3-bromo-benzyl)-N'-[4-(3-chloro-benzyl)-4-dimethylamino-cyclohexyl]-succinamide;
N-(4-bromo-2-fluoro-benzyl)-N'-[4-(3-chloro-benzyl)-4-dimethylamino-cyclohexyl]-succinamide;
N-[4-(3-chloro-benzyl)-4-dimethylamino-cyclohexyl]-N'-(1-phenyl-propyl)-succinamide;
N-[4-dimethylamino-4-(3-methyl-benzyl)-cyclohexyl]-N'-(4-fluoro-2-trifluoromethyl-benzyl)-succinamide;
N-[4-(3-chloro-benzyl)-4-dimethylamino-cyclohexyl]-N'-indan-2-yl-succinhmide;
N-[4-dimethylamino-4-(3-methyl-benzyl)-cyclohexyl]-4-oxo-4-(4-phenyl-3,6-dihydro-2H-pyridin-1-yl)-butyramide;
N-[4-(4-chloro-benzyl)-4-dimethylamino-cyclohexyl]-N'-[2-(2-fluoro-phenyl)-ethyl]-succinamide;
N-[4-dimethylamino-4-(4-methyl-benzyl)-cyclohexyl]-N'-[2-(2-fluoro-phenyl)-ethyl]-succinamide;
Glutaric acid-(4-benzyl-4-dimethylamino-cyclohexyl)-amide [2-(2-fluoro-phenyl)-ethyl]-amide;
N-[2-(2-chloro-phenyl)-ethyl]-N'-[4-dimethylamino-4-(4-methyl-benzyl)-cycloheXyl]-succinamide;
N-[4-(3-chloro-benzyl)-4-dimethylamino-cyclohexyl]-N'-(3,4-difluoro-benzyl)-succinamide;
N-benzyl-N-(2-cyano-ethyl)-N'-[4-dimethylamino-4-(4-methyl-benzyl)-cyclohexyl]-succinamide;
N-[4-(3-chloro-benzyl)-4-dimethylamino-cyclohexyl]-N'-(3-methyl-benzyl)-succinamide;
N-[4-(3-chloro-benzyl)-4-dimethylamino-cyclohexyl]-N'-(4-fluoro-3-trifluoromethyl-benzyl)-succinamide;
N-[4-(3-chloro-benzyl)-4-dimethylamino-cyclohexyl]-N'-[2-(2-chloro-phenyl)-ethyl]-succinamide;
N-[4-(3-chloro-benzyl)-4-dimethylamino-cyclohexyl]-N'-[2-(4-chloro-phenyl)-ethyl]-succinamide;
N-[4-(3-chloro-benzyl)-4-dimethylamino-cyclohexyl]-N'-[2-(2,4-dichloro-phenyl)-ethyl]-succinamide;
N-[4-(3-chloro-benzyl)-4-dimethylamino-cyclohexyl]-N'-indan-1-yl-succinamide;
N-[4-(4-chloro-benzyl)-4-dimethylamino-cyclohexyl]-N'-indan-1-yl-succinamide;
N-[2-(4-chloro-phenyl)-propyl]-N'-[4-dimethylamino-4-(3-methyl-benzyl)-cyclohexyl]-succinamide;
N-(3-bromo-benzyl)-N'-[4-(4-chloro-benzyl)-4-dimethylamino-cyclohexyl]-succinamide;
N-[4-(3-chloro-benzyl)-4-dimethylamino-cyclohexyl]-N'-(3-phenyl-propyl)-succinamide;
N-[4-dimethylamino-4-(4-methyl-benzyl)-cyclohexyl]-N'-(2-p-tolyl-ethyl)-succinamide;
N-[4-(3-chloro-benzyl)-4-dimethylamino-cyclohexyl]-N'-(2-thiophen-2-yl-ethyl)-succinamide;
Glutaric acid-(4-benzyl-4-dimethylamino-cyclohexyl)-amide [2-(4-chloro-phenyl)-propyl]-amide;
N-benzyl-N'-[4-(3-chloro-benzyl)-4-dimethylamino-cyclohexyl]-N-methyl-succinamide;
N-[4-(3-chloro-benzyl)-4-dimethylamino-cyclohexyl]-N'-[2-(3-chloro-phenyl)-ethyl]-succinamide;
Glutaric acid-(4-benzyl-4-dimethylamino-cyclohexyl)-amide [2-(2-ethoxy-phenyl)-ethyl]-amide;
Glutaric acid-(4-benzyl-4-dimethylamino-cyclohexyl)-amide phenethyl-amide;
Glutaric acid-(4-benzyl-4-dimethylamino-cyclohexyl)-amide [2-(3-chloro-phenyl)-ethyl]amide;
N-[4-(3-chloro-benzyl)-4-dimethylamino-cyclohexyl]-N'-[1-(3-methoxy-phenyl)-ethyl]-succinamide;

Glutaric acid-(4-benzyl-4-dimethylamino-cyclohexyl)-amide (1,3-dimethyl-butyl)-amide;
N-benzyl-N'-[4-dimethylamino-4-(3-methyl-benzyl)-cyclohexyl]-N-ethyl-succinamide;
N-(4-chloro-benzyl)-N'-[4-(3-chloro-benzyl)-4-dimethylamino-cyclohexyl]-succinamide;
N-[4-(3-chloro-benzyl)-4-dimethylamino-cyclohexyl]-N'-[2-(2-fluoro-phenyl)-ethyl]-succinamide;
N-[4-dimethylamino-4-(3-methyl-benzyl)-cyclohexyl]-N'-(2-fluoro-benzyl)-succinamide;
N-[2-(4-chloro-phenyl)-ethyl]-N'-[4-dimethylamino-4-(3-methyl-benzyl)-cyclohexyl]-succinamide;
N-[2-(2-chloro-phenyl)-ethyl]-N'-[4-dimethylamino-4-(3-methyl-benzyl)-cyclohexyl]-succinamide;
N-[2-(3-chloro-phenyl)-ethyl]-N'-[4-dimethylamino-4-(3-methyl-benzyl)-cyclohexyl]-succinamide;
N-benzyl-N'-[4-(3-chloro-benzyl)-4-dimethylamino-cyclohexyl]-N-(2-cyano-ethyl)-succinamide;
N-[4-(3-chloro-benzyl)-4-dimethylamino-cyclohexyl]-N'-(3-chloro-4-fluoro-benzyl)-succinamide;
N-[4-dimethylamino-4-(3-methyl-benzyl)-cyclohexyl]-N'-(2-trifluoromethyl-benzyl)-succinamide;
N-[2-(2,4-dichloro-phenyl)-ethyl]-N'-[4-dimethylamino-4-(3-methyl-benzyl)-cyclohexyl]-succinamide;
N-benzyl-N'-[4-(3-chloro-benzyl)-4-dimethylamino-cyclohexyl]-N-ethyl-succinamide;
N-[2-(4-chloro-phenyl)-ethyl]-N'-[4-dimethylamino-4-(4-methyl-benzyl)-cyclohexyl]-succinamide;
5-oxo-5-(4-o-tolyl-piperazin-1-yl)-valeric acid (4-benzyl-4-dimethylamino-cyclohexyl)-amide;
N-[4-(3-chloro-benzyl)-4-dimethylamino-cyclohexyl]-N'-[3-(methyl-phenyl-amino)-propyl]-succinamide;
N-[4-(3-chloro-benzyl)-4-dimethylamino-cyclohexyl]-4-[4-(5-chloro-2-methyl-phenyl)-piperazin-1-yl]-4-oxo-butyramide;
N-[4-dimethylamino-4-(3-methyl-benzyl)-cyclohexyl]-N'-[2-(2-ethoxy-phenyl)-ethyl]-succinamide;
4-[4-(4-chloro-benzoyl)-piperidin-1-yl]-N-[4-(3-chloro-benzyl)-4-dimethylamino-cyclohexyl]-4-oxo-butyramide;
N-[4-(3-chloro-benzyl)-4-dimethylamino-cyclohexyl]-N'-[2-(2-ethoxy-phenyl)-ethyl]-succinamide;
N-[2-(2,6-dichloro-phenyl)-ethyl]-N'-[4-dimethylamino-4-(3-methyl-benzyl)-cyclohexyl]-succinamide;
N-benzhydryl-N'-[4-(3-chloro-benzyl)-4-dimethylamino-cyclohexyl]-succinamide;
N-[4-(3-chloro-benzyl)-4-dimethylamino-cyclohexyl]-N'-cyclooctyl-succinamide;
N-[4-(3-chloro-benzyl)-4-dimethylamino-cyclohexyl]-N'-[2-(4-phenoxy-phenyl)-ethyl]-succinamide;
N-[4-dimethylamino-4-(3-methyl-benzyl)-cyclohexyl]-N'-(2,3-dimethyl-benzyl)-succinamide;
4-[4-(5-chloro-2-methyl-phenyl)-piperazin-1-yl]-N-[4-dimethylamino-4-(3-methyl-benzyl)-cyclohexyl]-4-oxo-butyramide;
4-[4-(4-chloro-benzoyl)-piperidin-1-yl]-N-[4-dimethylamino-4-(3-methyl-benzyl)-cyclohexyl]-4-oxo-butyramide;
N-[4-(3-chloro-benzyl)-4-dimethylamino-cyclohexyl]-N'-(1,2,3,4-tetrahydro-naphthalen-1-yl)-succinamide;
N-(2-chloro-benzyl)-N'-[4-dimethylamino-4-(3-methyl-benzyl)-cyclohexyl]-succinamide;
N-(2-chloro-benzyl)-N'-[4-(3-chloro-benzyl)-4-dimethylamino-cyclohexyl]-succinamide;
N-[4-(3-chloro-benzyl)-4-dimethylamino-cyclohexyl]-N'-(3-fluoro-5-trifluoromethyl-benzyl)-succinamide;
N-[4-(3-chloro-benzyl)-4-dimethylamino-cyclohexyl]-N'-(1-p-tolyl-ethyl)-succinamide;
N-[2-(2,6-dichloro-benzylsulphanyl)-ethyl]-N'-[4-dimethylamino-4-(4-methyl-benzyl)-cyclohexyl]-succinamide;
N-[4-(3-chloro-benzyl)-4-dimethylamino-cyclohexyl]-N'-[2-(2,6-dichloro-benzylsulphanyl)-ethyl]-succinamide;
N-[4-(3-chloro-benzyl)-4-dimethylamino-cyclohexyl]-N'-[2-(3-trifluoromethyl-phenyl)-ethyl]-succinamide;
N-[2-(3,4-dichloro-phenyl)-ethyl]-N'-[4-dimethylamino-4-(3-methyl-benzyl)-cyclohexyl]-succinamide;
N-[4-(3-chloro-benzyl)-4-dimethylamino-cyclohexyl]-4-[4-(2-fluoro-phenyl)-piperazin-1-yl]-4-oxo-butyramide;
5-[4-(2,4-dimethoxy-phenyl)-piperazin-1-yl]-5-oxo-valeric acid (4-benzyl-4-dimethylamino-cyclohexyl)-amide;
N-[4-(3-chloro-benzyl)-4-dimethylamino-cyclohexyl]-N'-(1-naphthalen-1-yl-ethyl)-succinamide;
N-[4-dimethylamino-4-(3-methyl-benzyl)-cyclohexyl]-N'-(1-naphthalen-1-yl-ethyl)-succinamide;
N-[4-(3-chloro-benzyl)-4-dimethylamino-cyclohexyl]-N'-(2-fluoro-benzyl)-N'-furan-2-ylmethyl-succinamide;
N-[4-dimethylamino-4-(3-methyl-benzyl)-cyclohexyl]-N'-(2-fluoro-benzyl)-N'-furan-2-ylmethyl-succinamide;
N-[4-(3-chloro-benzyl)-4-dimethylamino-cyclohexyl]-N'-(2,5-dimethoxy-benzyl)-N'-furan-2-ylmethyl-succinamide;
N-(4-azepan-1-yl-4-benzyl-cyclohexyl)-4-(2,3-dihydro-indol-1-yl)-4-oxo-butyramide;
4-(2,3-dihydro-indol-1-yl)-N-[4-dimethylamino-4-(3-fluoro-phenyl)-cyclohexyl]-4-oxo-butyramide;
N-(4-benzyl-4-morpholin-4-yl-cyclohexyl)-N'-(2-chloro-6-methyl-benzyl)-succinamide;
N-(4-benzyl-4-morpholin-4-yl-cyclohexyl)-N'-[2-(3-methoxy-phenyl)-ethyl]-succinamide;
N-(4-benzyl-4-morpholin-4-yl-cyclohexyl)-N'-(3-methyl-benzyl)-succinamide;
N-(4-benzyl-4-morpholin-4-yl-cyclohexyl)-N'-(4-bromo-2-fluoro-benzyl)-succinamide;
N-(4-benzyl-4-morpholin-4-yl-cyclohexyl)-N'-pyridin-4-ylmethyl-succinamide;
N-(4-benzyl-4-morpholin-4-yl-cyclohexyl)-N'-indan-1-yl-succinamide;
N-(4-benzyl-4-morpholin-4-yl-cyclohexyl)-N'-(2,4-dimethoxy-benzyl)-succinamide;
N-(4-benzyl-4-morpholin-4-yl-cyclohexyl)-N'-thiophen-2-ylmethyl-succinamide;
N-adamantan-1-ylmethyl-N'-(4-benzyl-4-morpholin-4-yl-cyclohexyl)-succinamide;
N-(4-benzyl-4-morpholin-4-yl-cyclohexyl)-N'-(2,5-difluoro-benzyl)-succinamide;
N-(4-benzyl-4-morpholin-4-yl-cyclohexyl)-N'-(4-tert-butyl-phenyl)-succinamide;
N-(4-benzyl-4-morpholin-4-yl-cyclohexyl)-N'-(3,5-bis-trifluoromethyl-benzyl)-succinamide;
N-(4-benzyl-4-morpholin-4-yl-cyclohexyl)-N'-[2-(2-ethoxy-phenyl)-ethyl]-succinamide;
N-(4-benzyl-4-morpholin-4-yl-cyclohexyl)-N'-(3-methoxy-propyl)-succinamide;
N-(4-benzyl-4-morpholin-4-yl-cyclohexyl)-N'-(2-morpholin-4-yl-ethyl)-succinamide;
N-(4-benzyl-4-morpholin-4-yl-cyclohexyl)-N'-(2,5-dichloro-benzyl)-succinamide;

N-(4-benzyl-4-morpholin-4-yl-cyclohexyl)-N'-[1-(2-ben-zyloxy-benzyl)-pyrrolidin-3-yl]-N'-methyl-succina-mide;
N-(4-benzyl-4-morpholin-4-yl-cyclohexyl)-4-oxo-4-(2-pyrrolidin-1-ylmethyl-pyrrolidin-1-yl)-butyramide;
N-(4-benzyl-4-morpholin-4-yl-cyclohexyl)-4-morpholin-4-yl-4-oxo-butyramide;
N-(4-benzyl-4-morpholin-4-yl-cyclohexyl)-N'-(3-dim-ethylamino-propyl)-N'-methyl-succinamide;
N-(4-benzyl-4-morpholin-4-yl-cyclohexyl)-N'-(2-phenyl-cyclopropyl)-succinamide;
N-(4-benzyl-4-morpholin-4-yl-cyclohexyl)-N'-naphtha-len-1-ylmethyl-succinamide;
N-(4-benzyl-4-morpholin-4-yl-cyclohexyl)-4-(4-methyl-[1,4]diazepan-1-yl)-4-oxo-butyramide;
N-(4-benzyl-4-morpholin-4-yl-cyclohexyl)-4-(4-hy-droxy-piperidin-1-yl)-4-oxo-butyramide;
N-(4-benzyl-4-morpholin-4-yl-cyclohexyl)-N'-[2-(7-me-thyl-1H-indol-3-yl)-ethyl]-succinamide;
N-(4-benzyl-4-morpholin-4-yl-cyclohexyl)-N'-[2-(5-methoxy-1H-indol-3-yl)-ethyl]-succinamide;
N-(4-benzyl-4-morpholin-4-yl-cyclohexyl)-4-oxo-4-(4-quinolin-2-ylmethyl-piperazin-1-yl)-butyramide;
N-(4-dimethylamino-4-thiophen-2-yl-cyclohexyl)-4-oxo-4-[4-(5-trifluoromethyl-pyridin-2-yl)-piperazin-1-yl]-butyramide;
Glutaric acid-(1-adamantan-1-yl-ethyl)-amide (4-dim-ethylamino-4-thiophen-2-yl-cyclohexyl)-amide;
N-[2-(2,6-dichloro-phenyl)-ethyl]-N'-(4-dimethylamino-4-thiophen-2-yl-cyclohexyl)-succinamide;
N-(4-dimethylamino-4-thiophen-2-yl-cyclohexyl)-N'-(1-methyl-3-phenyl-propyl)-succinamide;
N-benzyl-N'-(4-dimethylamino-4-thiophen-2-yl-cyclo-hexyl)-N-ethyl-succinamide;
N-[2-(4-bromo-phenyl)-ethyl]-N'-(4-dimethylamino-4-thiophen-2-yl-cyclohexyl)-succinamide;
4-[4-(4-chloro-benzoyl)-piperidin-1-yl]-N-(4-dimethy-lamino-4-thiophen-2-yl-cyclohexyl)-4-oxo-butyra-mide;
Glutaric acid-[1-(2,6-dichloro-benzyl)-pyrrolidin-3-yl]-amide (4-dimethylamino-4-thiophen-2-yl-cyclohexyl)-amide;
Glutaric acid-(4-dimethylamino-4-thiophen-2-yl-cyclo-hexyl)-amide (3-phenyl-propyl)-amide;
N-(4-dimethylamino-4-phenyl-cyclohexyl)-N'-pentyl-succinamide;
3-(4-chloro-phenyl)-2-[4-(4-dimethylamino-4-thiophen-2-yl-cyclohexylcarbamoyl)-butyrylamino]-propanoic acid ethylester;
Glutaric acid-(4-dimethylamino-4-thiophen-2-yl-cyclo-hexyl)-amide indan-1-ylamide;
N-adamantan-1-ylmethyl-N'-(4-dimethylamino-4-thiophen-2-yl-cyclohexyl)-succinamide;
5-(4-benzofuran-2-ylmethyl-piperazin-1-yl)-5-oxo-va-leric acid (4-dimethylamino-4-thiophen-2-yl-cyclo-hexyl)-amide;
4-[4-(4-tert-butyl-benzyl)-piperazin-1-yl]-N-(4-dimethy-lamino-4-phenyl-cyclohexyl)-4-oxo-butyramide;
Glutaric acid-(4-dimethylamino-4-thiophen-2-yl-cyclo-hexyl)-amide [2-(1H-indol-3-yl)-ethyl]-amide;
N-(4-dimethylamino-4-phenyl-cyclohexyl)-4-[4-hy-droxy-4-(3-trifluoromethyl-phenyl)-piperidin-1-yl]-4-oxo-butyramide;
5-(3,4-dihydro-1H-isoquinolin-2-yl)-5-oxo-valeric acid (4-dimethylamino-4-thiophen-2-yl-cyclohexyl)-amide;
4-(4-benzyl-piperidin-1-yl)-N-(4-dimethylamino-4-phe-nyl-cyclohexyl)-4-oxo-butyramide;
{[4-(4-dimethylamino-4-thiophen-2-yl-cyclohexylcar-bamoyl)-butyryl]-methyl-amino}-acetic acid benzy-lester;
N-benzyl-N'-(4-dimethylamino-4-phenyl-cyclohexyl)-N-phenethyl-succinamide;
Glutaric acid-(4-dimethylamino-4-thiophen-2-yl-cyclo-hexyl)-amide 3-trifluoromethoxy-benzylamide;
Glutaric acid-(4-dimethylamino-4-thiophen-2-yl-cyclo-hexyl)-amide ethyl-(2-methyl-allyl)-amide;
N,N-bis-(2-cyano-ethyl)-N'-(4-dimethylamino-4-thiophen-2-yl-cyclohexyl)-succinamide;
Glutaric acid-benzyl-methyl-amide (4-dimethylamino-4-thiophen-2-yl-cyclohexyl)-amide;
Glutaric acid-(2-benzyloxy-cyclopentyl)-amide (4-dim-ethylamino-4-thiophen-2-yl-cyclohexyl)-amide;
Glutaric acid-(4-dimethylamino-4-thiophen-2-yl-cyclo-hexyl)-amide 4-trifluoromethyl-benzylamide;
N-(4-dimethylamino-4-thiophen-2-yl-cyclohexyl)-N'-[2-(4-phenoxy-phenyl)-ethyl]-succinamide;
Glutaric acid-(4-dimethylamino-4-thiophen-2-yl-cyclo-hexyl)-amide (3,3-diphenyl-propyl)-amide;
4-(4-benzyl-piperidin-1-yl)-N-(4-dimethylamino-4-thiophen-2-yl-cyclohexyl)-4-oxo-butyramide;
N-(4-dimethylamino-4-thiophen-2-yl-cyclohexyl)-4-[4-hydroxy-4-(3-trifluoromethyl-phenyl)-piperidin-1-yl]-4-oxo-butyramide;
Glutaric acid-(4-dimethylamino-4-thiophen-2-yl-cyclo-hexyl)-amide 4-fluoro-2-trifluoromethyl-benzylamide;
N-(4-dimethylamino-4-thiophen-2-yl-cyclohexyl)-N'-pentyl-succinamide;
5-[4-(2-methoxy-naphthalen-1-ylmethyl)-piperazin-1-yl]-5-oxo-valeric acid (4-dimethylamino-4-thiophen-2-yl-cyclohexyl)-amide;
N-(4-dimethylamino-4-thiophen-2-yl-cyclohexyl)-N'-(2-ethoxy-benzyl)-N'-furan-2-ylmethyl-succinamide;
Glutaric acid-(4-dimethylamino-4-thiophen-2-yl-cyclo-hexyl)-amide (2-phenyl-cyclopropyl)-amide;
N-[2-(3,4-dichloro-phenyl)-ethyl]-N'-(4-dimethylamino-4-phenyl-cyclohexyl)-succinamide;
N-adamantan-1-ylmethyl-N'-(4-dimethylamino-4-phe-nyl-cyclohexyl)-succinamide;
5-[4-(4-fluoro-phenyl)-3,6-dihydro-2H-pyridin-1-yl]-5-oxo-valeric acid (4-dimethylamino-4-thiophen-2-yl-cy-clohexyl)-amide;
2-[4-(4-dimethylamino-4-thiophen-2-yl-cyclohexylcar-bamoyl)-butyrylamino]-4-methyl-valeric acid benzyl ester;
{4-[4-(4-dimethylamino-4-thiophen-2-yl-cyclohexylcar-bamoyl)-butyrylamino]-phenyl}-carbamic acid-tert-bu-tylester;
Glutaric acid-(4-dimethylamino-4-thiophen-2-yl-cyclo-hexyl)-amide [2-(3-methoxy-phenyl)-ethyl]-amide;
Glutaric acid-benzyl-ethyl-amide (4-dimethylamino-4-thiophen-2-yl-cyclohexyl)-amide;
Glutaric acid-3-chloro-benzylamide (4-dimethylamino-4-thiophen-2-yl-cyclohexyl)-amide;
Glutaric acid-(4-dimethylamino-4-thiophen-2-yl-cyclo-hexyl)-amide (4-methyl-cyclohexyl)-amide;
N-(4-dimethylamino-4-phenyl-cyclohexyl)-N'-[2-(1H-in-dol-3-yl)-ethyl]-N'-methyl-succinamide;
Glutaric acid-2,5-dichloro-benzylamide (4-dimethy-lamino-4-thiophen-2-yl-cyclohexyl)-amide;
Glutaric acid-(4-dimethylamino-4-thiophen-2-yl-cyclo-hexyl)-amide [2-(3-fluoro-phenyl)-ethyl]-amide;
N-(4-dimethylamino-4-phenyl-cyclohexyl)-N'-[2-(4-methoxy-phenoxy)-ethyl]-succinamide;

N-(4-dimethylamino-4-thiophen-2-yl-cyclohexyl)-N'-[2-(ethyl-m-tolyl-amino)-ethyl]-succinamide;
Glutaric acid-(4-benzyloxy-phenyl)-amide (4-dimethylamino-4-thiophen-2-yl-cyclohexyl)-amide;
Glutaric acid-(4-dimethylamino-4-thiophen-2-yl-cyclohexyl)-amide [2-(4-fluoro-phenyl)-ethyl]-amide;
Glutaric acid-[2-(4-bromo-phenyl)-ethyl]-amide (4-dimethylamino-4-thiophen-2-yl-cyclohexyl)-amide;
N-(4-dimethylamino-4-thiophen-2-yl-cyclohexyl)-N'-(4-phenoxy-phenyl)-succinamide;
N-(4-dimethylamino-4-phenyl-cyclohexyl)-N'-[2-(3-trifluoromethyl-phenyl)-ethyl]-succinamide;
Glutaric acid-[2-(4-chloro-phenyl)-propyl]-amide (4-dimethylamino-4-thiophen-2-yl-cyclohexyl)-amide;
N-(4-dimethylamino-4-thiophen-2-yl-cyclohexyl)-N'-[2-(1H-indol-3-yl)-ethyl]-N'-methyl-succinamide;
N-(4-dimethylamino-4-thiophen-2-yl-cyclohexyl)-N'-[2-(4-methoxy-phenoxy)-ethyl]-succinamide;
Glutaric acid-(4-dimethylamino-4-thiophen-2-yl-cyclohexyl)-amide (3-phenoxy-phenyl)-amide;
N-(4-dimethylamino-4-phenyl-cyclohexyl)-N'-[2-(ethyl-m-tolyl-amino)-ethyl]-succinamide;
Glutaric acid-[2-(5-bromo-2-methoxy-phenyl)-ethyl]-amide (4-dimethylamino-4-thiophen-2-yl-cyclohexyl)-amide;
N-(4-dimethylamino-4-thiophen-2-yl-cyclohexyl)-N'-[2-(3-trifluoromethyl-phenyl)-ethyl]-succinamide;
Glutaric acid-(4-dimethylamino-4-thiophen-2-yl-cyclohexyl)-amide (1-methyl-3-phenyl-propyl)-amide;
N-[2-(2,6-dichloro-benzylsulphanyl)-ethyl]-N'-(4-dimethylamino-4-thiophen-2-yl-cyclohexyl)-succinamide;
Glutaric acid-(4-dimethylamino-4-thiophen-2-yl-cyclohexyl)-amide (2,2-diphenyl-propyl)-amide;
N-(4-dimethylamino-4-thiophen-2-yl-cyclohexyl)-N'-[3-(methyl-phenyl-amino)-propyl]-succinamide;
N-(1-biphenyl-4-ylmethyl-pyrrolidin-3-yl)-N'-(4-dimethylamino-4-thiophen-2-yl-cyclohexyl)-N-methyl-succinamide;
Glutaric acid-[4-(cyano-phenyl-methyl)-phenyl]-amide (4-dimethylamino-4-thiophen-2-ylcyclohexyl)-amide;
Glutaric acid-(4-tert-butyl-cyclohexyl)-amide (4-dimethylamino-4-thiophen-2-yl-cyclohexyl)-amide;
Glutaric acid-(4-sec-butyl-phenyl)-amide (4-dimethylamino-4-thiophen-2-yl-cyclohexyl)-amide;
Glutaric acid-(4-butyl-phenyl)-amide (4-dimethylamino-4-thiophen-2-yl-cyclohexyl)-amide;
N-(2-benzylsulphanyl-ethyl)-N'-(4-dimethylamino-4-thiophen-2-yl-cyclohexyl)-succinamide;
N-(4-dimethylamino-4-thiophen-2-yl-cyclohexyl)-N'-(2-phenoxy-ethyl)-succinamide;
Glutaric acid-(4-dimethylamino-4-thiophen-2-yl-cyclohexyl)-amide (naphthalen-1-ylmethyp-amide;
Glutaric acid-3-bromo-benzylamide (4-dimethylamino-4-thiophen-2-yl-cyclohexyl)-amide;
N-(4-dimethylamino-4-thiophen-2-yl-cyclohexyl)-N'-(3-phenyl-propyl)-succinamide;
N-[2-(3-chloro-phenyl)-ethyl]-N'-(4-dimethylamino-4-phenyl-cyclohexyl)-succinamide;
2-[3-(4-dimethylamino-4-thiophen-2-yl-cyclohexylcarbamoyl)-propionylamino]-; propanoic acid benzylester;
N-[2-(2-chloro-phenyl)-ethyl]-N'-(4-dimethylamino-4-phenyl-cyclohexyl)-succinamide;
N-(4-dimethylamino-4-phenyl-cyclohexyl)-N'-[2-(3-fluoro-phenyl)-ethyl]-succinamide;
Glutaric acid-(4-dimethylamino-4-thiophen-2-yl-cyclohexyl)-amide (2-thiophen-2-yl-ethyl)-amide;
Glutaric acid-(4-dimethylamino-4-thiophen-2-yl-cyclohexyl)-amide [2-(4-phenoxy-phenyl)-ethyl]-amide;
N-[2-(4-chloro-phenyl)-ethyl]-N'-(4-dimethylamino-4-phenyl-cyclohexyl)-succinamide;
N-[2-(3-chloro-phenyl)-ethyl]-N'-(4-dimethylamino-4-thiophen-2-yl-cyclohexyl)-succinamide;
N-benzyl-N'-(4-dimethylamino-4-thiophen-2-yl-cyclohexyl)-N-ethyl-succinamide;
Glutaric acid-[1-(2,6-dichloro-benzyl)-pyrrolidin-3-yl]-amide (4-dimethylamino-4-thiophen-2-yl-cyclohexyl)-amide;
Glutaric acid-(4-dimethylamino-4-thiophen-2-yl-cyclohexyl)-amide (3-phenyl-propyl)-amide;
Glutaric acid-(4-dimethylamino-4-thiophen-2-yl-cyclohexyl)-amide [2-(1H-indol-3-yl)-ethyl]-amide;
5-(3,4-dihydro-1H-isoquinolin-2-yl)-5-oxo-valeric acid (4-dimethylamino-4-thiophen-2-yl-cyclohexyl)-amide;
{[4-(4-dimethylamino-4-thiophen-2-yl-cyclohexylcarbamoyl)-butyryl]-methyl-amino}-acetic acid benzylester;
N-(4-dimethylamino-4-thiophen-2-yl-cyclohexyl)-N'-[2-(4-phenoxy-phenyl)-ethyl]-succinamide;
Glutaric acid-(4-dimethylamino-4-thiophen-2-yl-cyclohexyl)-amide (2-phenyl-cyclopropyl)-amide;
N-[4-(3-chlorobenzyl)-4-dimethylaminocyclohexyl]-N'-furan-2-ylmethylsuccinic acid amide hydrochloride, non-polar diastereoisomer;
N-[4-(3-chlorobenzyl)-4-dimethylaminocyclohexyl]-N'-furan-2-ylmethylsuccinic acid amide hydrochloride, polar diastereoisomer;
Glutaric acid (4-benzyl-4-dimethylaminocyclohexyl) amide [2-(2-fluorophenyl)ethyl]amide hydrochloride, non-polar diastereoisomer;
Glutaric acid (4-benzyl-4-dimethylaminocyclohexyl) amide [2-(2-fluorophenyl)ethyl]amide hydrochloride, polar diastereoisomer;
N-[4-(3-chlorobenzyl)-4-dimethylaminocyclohexyl]-N'-[2-(4-chlorophenyl)ethyl]-succinic acid amide hydrochloride, non-polar diastereoisomer;
N-[4-(3-chlorobenzyl)-4-dimethylaminocyclohexyl]-N'-[2-(4-chlorophenyl)ethyl]-succinic acid amide hydrochloride, polar diastereoisomer; and
Glutaric acid (4-benzyl-4-dimethylaminocyclohexyl) amide [2-(4-chlorophenyl)ethyl]amide hydrochloride, non-polar diastereoisomer.

18. A process for preparing a cyclohexyl-1,4-diamine compound according to claim 1, comprising the steps of:
    linking a cyclohexane-1,4-diamine compound to a primary or secondary amine via an anhydride, open-chain dicarboxylic acid or an activated analog thereof.

19. The method of claim 18, wherein said activated analog is an acid halide.

20. A process for preparing a cyclohexyl-1,4-diamine compound according to claim 1, comprising the steps of:
    reacting one or more coupling agents to link an anhydride, open-chain dicarboxylic acid or an activated analog thereof with a primary or secondary amine and
    linking a substituted cyclohexane-1,4-diamine thereto.

21. The method of claim 20, wherein said activated analog is an acid halide.

22. A pharmaceutical formulation comprising at least one cyclohexyl-1,4-diamine compound according to claim 1 and one or more physiologically acceptable auxiliary substances.

23. A method of producing a pharmaceutical formulation comprising the steps of combining a pharmaceutically effective amount of a cyclohexyl-1,4-diamine compound according to claim 1 and one or more physiologically acceptable auxiliary substances.

24. A method of treating pain in a mammal, said method comprising administering to said mammal an effective amount of a compound according to claim 1.

25. The method of claim 24, wherein said pain is acute, neuropathic or chronic pain.

26. A method of treating a condition selected from the group consisting of anxiety, stress and stress-related syndromes, depression, epilepsy, withdrawal symptoms, alcohol abuse or dependency, drug abuse or dependency, medicine abuse or dependency, sexual dysfunction, hypotension, hypertension, tinnitus, pruritus, migraine, deficient intestinal motility, impaired nutrient absorption, anorexia, obesity, diarrhea, cachexia, urinary incontinence, or providing a muscle relaxant, nootropic, anti-convulsive or anaesthetic or for co-administration in treatment with an opioid analgesic or anaesthetic, for diuresis or anti-natriuresis, anxiolysis, for the treatment of withdrawal symptoms or for reducing opioid addiction potential, said method comprising administering to a subject in need thereof a pharmaceutically effective amount of a compound according to claim 1.

27. A cyclohexyl-1,4-diamine compound corresponding to formula I,

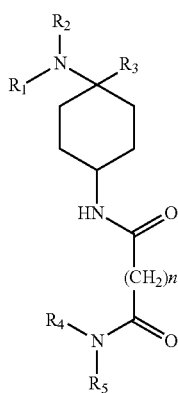

I wherein
n represents 1, 2, 3, 4 or 5
$R^1$ and $R^2$ independently of one another represent H; saturated or unsaturated, branched or unbranched, singly or multiply substituted or unsubstituted $C_{1-5}$ alkyl; singly or multiply substituted or unsubstituted $C_{3-8}$ cycloalkyl; or singly or multiply substituted or unsubstituted aryl, $C_{3-8}$ cycloalkyl or heteroaryl bound by $C_{1-3}$ alkyl;
or $R^1$ and $R^2$ together form a ring and represent $CH_2CH_2OCH_2CH_2$, $CH_2CH_2NR^{10}CH_2CH_2$ or $(CH2)_{3-6}$,
wherein $R^{10}$ represents H; saturated or unsaturated, branched or unbranched, singly or multiply substituted or unsubstituted $C_{1-5}$ alkyl singly or multiply substituted or unsubstituted $C_{3-8}$ cycloalkyl; singly or multiply substituted or unsubstituted aryl or heteroaryl; or singly or multiply substituted or unsubstituted aryl, $C_{3-8}$ cycloalkyl or heteroaryl bound by $C_{1-3}$ alkyl; substituted or unsubstituted C(O)phenyl, C(O)heteroaryl, C(O)$C_{1-5}$ alkyl;
$R^3$ represents saturated or unsaturated, branched or unbranched, singly or multiply substituted or unsubstituted $C_{1-5}$ alkyl; singly or multiply substituted or unsubstituted $C_{3-8}$ cycloalkyl; unsubstituted or singly or multiply substituted aryl or heteroaryl; unsubstituted or singly or multiply substituted aryl, heteroaryl or $C_{3-8}$ cycloalkyl bound by a $C_{1-3}$ alkyl group;
$R^4$ represents —$(CR^6R^7)_pR^8$,
wherein p represents 0, 1, 2, 3 or 4;
$R^6$ represents H or saturated or unsaturated, branched or unbranched, unsubstituted or singly or multiply substituted $C_{1-5}$ alkyl;
$R^7$ represents H, saturated or unsaturated, branched or unbranched, unsubstituted or singly or multiply substituted $C_{1-5}$ alkyl or COOR$^9$;
or $R^6$ and $R^7$ together form a ring and represent $(CH_2)_kCHR^8(CH_2)_m$, where k =1, 2, or 3 and m =1 or 2;
$R^8$ represents respectively saturated or unsaturated, branched or unbranched, unsubstituted or singly or multiply substituted $C_{1-6}$ alkyl; unsubstituted or singly or multiply substituted $C_{3-8}$ cycloalkyl, aryl or heteroaryl;
$R^9$ represents H or $C_{1-5}$ alkyl;
$R^5$ represents H or —$(CH_2)_lR^8$,
wherein l represents 1, 2 or 3
or $R^5$ and $R^4$ together form a ring and represent $CH_2CHR^{14}CHR^{14}CH_2$, $CH_2CH_2SCH_2CH_2$ $CH_2CH_2NR^{11}CH_2CH_2$, $(CR^{12}R^{13})_{3-6}$ or

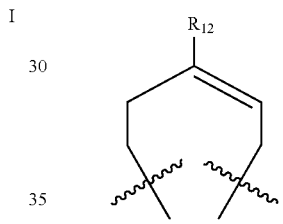

wherein $R^{11}$ represents H; saturated or unsaturated, branched or unbranched, singly or multiply substituted or unsubstituted $C_{1-5}$ alkyl; saturated or unsaturated, singly or multiply substituted or unsubstituted $C_{3-8}$ cycloalkyl; singly or multiply substituted or unsubstituted aryl or heteroaryl; or singly or multiply substituted or unsubstituted aryl, $C_{3-8}$ cycloalkyl or heteroaryl bound by $C_{1-3}$ alkyl;
$R^{12}$ represents H; saturated or unsaturated, branched or unbranched, singly or multiply substituted or unsubstituted $C_{1-5}$ alkyl; OH; unsubstituted or singly or multiply substituted C(O)phenyl; singly or multiply substituted or unsubstituted $C_{3-8}$ cycloalkyl; respectively singly or multiply substituted or unsubstituted aryl or heteroaryl; or singly or multiply substituted or unsubstituted aryl, $C_{3-8}$ cycloalkyl or heteroaryl bound by $C_{1-3}$ alkyl;
and $R^{13}$ represents H or OH or together with $R^{12}$ via the same C atom (spiro compound) or an adjacent C atom forms a five-membered or six-membered ring which may contain heteroatoms, be saturated or unsaturated, substituted or unsubstituted or be part of a polycyclic system;
$R^{14}$ represents respectively saturated or unsaturated, branched or unbranched, singly or multiply substituted or unsubstituted $C_{1-3}$ alkyl;
or an acid, base, or a physiologically acceptable salt thereof.

28. A cyclohexyl-1,4-diamine compound corresponding to formula I,

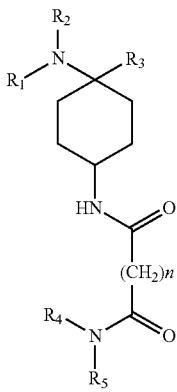

I wherein
n represents 1, 2, 3, 4 or 5
$R^1$ and $R^2$ independently of one another represent H; saturated or unsaturated, branched or unbranched, singly or multiply substituted or unsubstituted $C_{1-5}$ alkyl; singly or multiply substituted or unsubstituted $C_{3-8}$ cycloalkyl; or singly or multiply substituted or unsubstituted aryl, $C_{3-8}$ cycloalkyl or heteroaryl bound by $C_{1-3}$ alkyl;
or $R^1$ and $R^2$ together form a ring and represent $CH_2CH_2OCH_2CH_2$, $CH_2CH_2NR^{10}CH_2CH_2$ or $(CH2)_{3-6}$,
wherein $R^{10}$ represents H; saturated or unsaturated, branched or unbranched, singly or multiply substituted or unsubstituted $C_{1-5}$ alkyl singly or multiply substituted or unsubstituted $C_{3-8}$ cycloalkyl; singly or multiply substituted or unsubstituted aryl or heteroaryl; or singly or multiply substituted or unsubstituted aryl, $C_{3-8}$ cycloalkyl or heteroaryl bound by $C_{1-3}$ alkyl; substituted or unsubstituted C(O)phenyl, C(O)heteroaryl, $C(O)C_{1-5}$ alkyl;
$R^3$ represents saturated or unsaturated, branched or unbranched, singly or multiply substituted or unsubstituted $C_{1-5}$ alkyl; singly or multiply substituted or unsubstituted $C_{3-8}$ cycloalkyl; unsubstituted or singly or multiply substituted aryl or heteroaryl; unsubstituted or singly or multiply substituted aryl, heteroaryl or $C_{3-8}$ cycloalkyl bound by a $C_{1-3}$ alkyl group;
$R^4$ represents $—(CR^6R^7)_pR^8$,
wherein p represents 0, 1, 2, 3 or 4;
$R^6$ represents H or saturated or unsaturated, branched or unbranched, unsubstituted or singly or multiply substituted $C_{1-5}$ alkyl;
$R^7$ represents H, saturated or unsaturated, branched or unbranched, unsubstituted or singly or multiply substituted $C_{1-5}$ alkyl or $COOR^9$;
or $R^6$ and $R^7$ together form a ring and represent $(CH_2)_kCHR^8(CH_2)_m$, where k=1, 2, or 3 and m=1 or 2;
$R^8$ represents respectively saturated or unsaturated, branched or unbranched, unsubstituted or singly or multiply substituted $C_{1-6}$ alkyl; unsubstituted or singly or multiply substituted $C_{3-8}$ cycloalkyl, aryl or heteroaryl;
$R^9$ represents H or $C_{1-5}$ alkyl;
$R^5$ represents H or $—(CH_2)_lR^8$,
wherein l represents 1, 2 or 3
or $R^5$ and $R^4$ together form a ring and represent $CH_2CHR^{14}OCHR^{14}CH_2$, $CH_2CH_2SCH_2CH_2$, $CH_2CH_2NR^{11}CH_2CH_2$, $(CR^{12}R^{13})_{3-6}$ or

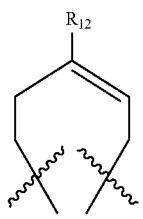

wherein $R^{11}$ represents H; saturated or unsaturated, branched or unbranched, singly or multiply substituted or unsubstituted $C_{1-5}$ alkyl; saturated or unsaturated, singly or multiply substituted or unsubstituted $C_{3-8}$ cycloalkyl; singly or multiply substituted or unsubstituted aryl or heteroaryl; or singly or multiply substituted or unsubstituted aryl, $C_{3-8}$ cycloalkyl or heteroaryl bound by $C_{1-3}$ alkyl;
$R^{12}$ represents H; saturated or unsaturated, branched or unbranched, singly or multiply substituted or unsubstituted $C_{1-5}$ alkyl; OH; unsubstituted or singly or multiply substituted C(O)phenyl; singly or multiply substituted or unsubstituted $C_{3-8}$ cycloalkyl; respectively singly or multiply substituted or unsubstituted aryl or heteroaryl; or singly or multiply substituted or unsubstituted aryl, $C_{3-8}$ cycloalkyl or heteroaryl bound by $C_{1-3}$ alkyl;
$R^{13}$ represents H or OH or together with $R^{12}$ via the same C atom or an adjacent C atom forms a five-membered or six-membered ring which may contain heteroatoms, be saturated or unsaturated, substituted or unsubstituted or be part of a polycyclic system; and
$R^{14}$ represents respectively saturated or unsaturated, branched or unbranched, singly or multiply substituted or unsubstituted $C_{1-3}$ alkyl;
or an acid, base, or a physiologically acceptable salt thereof.

* * * * *